(12) United States Patent
Hager et al.

(10) Patent No.: US 9,855,270 B2
(45) Date of Patent: *Jan. 2, 2018

(54) METHODS AND COMPOSITIONS FOR MODULATING ESTROGEN RECEPTOR MUTANTS

(71) Applicant: Genentech, Inc., South San Francisco, CA (US)

(72) Inventors: Jeffrey J. Hager, San Diego, CA (US); James D. Joseph, San Diego, CA (US); Jing Qian, San Diego, CA (US); Nicholas D. Smith, San Diego, CA (US); Edna Chow Maneval, San Diego, CA (US); Debasish F. Roychowdhury, San Diego, CA (US); Lori Friedman, San Carlos, CA (US); Deepak Sampath, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/645,578

(22) Filed: Mar. 12, 2015

(65) Prior Publication Data

US 2015/0258099 A1    Sep. 17, 2015

Related U.S. Application Data

(60) Provisional application No. 61/952,728, filed on Mar. 13, 2014, provisional application No. 61/981,708, filed on Apr. 18, 2014.

(51) Int. Cl.
| | | |
|---|---|---|
| A61K 31/5375 | (2006.01) | |
| A61K 31/416 | (2006.01) | |
| A61K 31/4245 | (2006.01) | |
| A61K 31/428 | (2006.01) | |
| A61K 31/437 | (2006.01) | |
| A61K 31/4025 | (2006.01) | |
| A61K 31/397 | (2006.01) | |
| C12Q 1/68 | (2006.01) | |

(52) U.S. Cl.
CPC ........ A61K 31/5375 (2013.01); A61K 31/397 (2013.01); A61K 31/4025 (2013.01); A61K 31/416 (2013.01); A61K 31/428 (2013.01); A61K 31/4245 (2013.01); A61K 31/437 (2013.01); C12Q 1/6886 (2013.01); C12Q 2600/156 (2013.01)

(58) Field of Classification Search
CPC ............... A61K 31/416; A61K 31/397; A61K 31/4025; A61K 31/4245; A61K 31/428; A61K 31/437; A61K 31/5375; C12Q 1/6886; C12Q 2600/156
See application file for complete search history.

(56) References Cited

U.S. PATENT DOCUMENTS

| | | |
|---|---|---|
| 8,299,112 B2 | 10/2012 | Smith et al. |
| 8,455,534 B2 | 6/2013 | Smith et al. |
| 8,703,810 B2 | 4/2014 | Kahraman et al. |
| 9,078,871 B2 | 7/2015 | Kahraman et al. |
| 9,187,460 B2 | 11/2015 | Smith et al. |
| 2003/0207380 A1 | 11/2003 | Saito et al. |
| 2012/0071535 A1 | 3/2012 | Smith et al. |
| 2013/0231333 A1 | 9/2013 | Smith et al. |
| 2015/0105403 A1 | 4/2015 | Smith et al. |

FOREIGN PATENT DOCUMENTS

| | | | |
|---|---|---|---|
| WO | 2015/082990 A1 | 6/2011 | |
| WO | 2011/156518 A2 | 12/2011 | |
| WO | 2012/037410 A2 | 3/2012 | |
| WO | 2012/037411 A2 | 3/2012 | |
| WO | 2013/056178 | 4/2013 | |
| WO | WO 2013056178 A2 * | 4/2013 | ........... C12Q 1/6886 |
| WO | 2013/090829 | 6/2013 | |
| WO | 2013/090836 A1 | 6/2013 | |
| WO | 2013/142266 A1 | 9/2013 | |
| WO | 2014/151899 A1 | 9/2014 | |
| WO | 2014/205136 A1 | 12/2014 | |
| WO | 2014/205138 A1 | 12/2014 | |
| WO | 2015/136016 A2 | 9/2015 | |

OTHER PUBLICATIONS

Martinez-Campa et. al., Hormonal Carcinogenesis IV, Proceedings of the International Symposium, 4th, Jun. 21-25, 2003, Springer Science & Business Media, pp. 391-397.*
Quaynor et. al., The New England Journal of Medicine, Jul. 2013, Massachusetts Medical Society, vol. 369, pp. 164-171.*
Puzianowska-Kuznicka, Clinica Chimica Acta, 2012, Elsevier, vol. 413, pp. 81-87.*
Chabner et. al., Nature Reviews Cancer, 2005, Nature Publishing Group, vol. 5, pp. 65-72.*
Leaf, Fortune, 2004, Time Inc., pp. 1-28.*
Ferrari, BoneKEy-Osteovision, 2006, International Bone and Mineral Society, vol. 3(12), pp. 11-29.*
Groheux et al., "Estrogen Receptor-Positive/Human Epidermal Growth Factor Receptor 2-Negative Breast Tumors" Cancer 119(11):1960-68 ( 2013).
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 ( 2015).

(Continued)

*Primary Examiner* — Sarah Pihonak
(74) *Attorney, Agent, or Firm* — Kevin M. Clark

(57) ABSTRACT

Described herein are methods and compositions for treating an ER-related disease condition characterized by a mutation in the ESR1 gene by administering an estrogen receptor modulator. Also described herein are methods of treating hormone resistant-estrogen receptor (ER) positive breast cancers characterized by a mutation in the ESR1 gene by administering an estrogen receptor modulator.

35 Claims, 6 Drawing Sheets

(56) References Cited

OTHER PUBLICATIONS

ISR for PCT/EP2015/055120, WO 2015/136017.
Lips et al., "Neoadjuvant chemotherapy in ER+ HER2—breast cancer:response prediction based on immunohistochemical and molecular characteristics" Breast Cancer Res Treat 131:827-36 (Apr. 2011).
Peterson et al., "Quantitative Imaging of Estrogen Receptor Expression in Breast Cancer with PET and 18F-Fluoroestradiol" Jour. of Nuclear Med. 49(3):367-74 ( 2008).
Dan R Robinson et al., "Activating ESR1 mutations in hormone-resistant metastatic breast cancer" Nature Genetics 45(12):1446-1451 (Nov. 3, 2013).
Govek et al., "Optimization of an indazole series of selective estrogen receptor degraders: Tumor regression in a tamoxifen-resistant breast cancer xenograft" Bioorg Med Chem Lett. 25(22):5163-7 ( 2015).
Y. Arao et al., "Estrogen Receptor L543A,L544A Mutation Changes Antagonists to Agonists, Correlating with the Ligand Binding Domain Dimerization Associated with DNA Binding Activity" Journal of Biological Chemistry 288(29):21105-21116 (Jul. 19, 2013).

\* cited by examiner

Pre-treatment      ARN-810 – one month 600 mg/day

METHODS AND COMPOSITIONS FOR MODULATING ESTROGEN RECEPTOR MUTANTS

CROSS REFERENCE TO RELATED APPLICATIONS

This non-provisional application filed under 37 CFR §1.53(b), claims the benefit under 35 USC §119(e) of U.S. Provisional Application Ser. No. 61/952,728 filed on 13 Mar. 2014 and U.S. Provisional Application Ser. No. 61/981,708 filed on 18 Apr. 2014, which are incorporated by reference in entirety.

SEQUENCE LISTING

The instant application contains a Sequence Listing, which has been submitted as a computer readable text file in ASCII format via EFS-Web and is hereby incorporated in its entirety by reference herein. The text file, created date of Mar. 13, 2014, is named 45202-739-101seqlist.txt and is 8 KB in size.

FIELD OF THE INVENTION

Described herein are methods of treating hormone resistant-estrogen receptor (ER) positive breast cancers characterized by a mutation in the ER gene in one or more tumor cells in women by administering an estrogen receptor modulator.

BACKGROUND OF THE INVENTION

Breast cancer is the most common form of cancer and the leading cause of cancer death in women worldwide. Approximately 80% of all breast cancers express and are dependent on the estrogen receptor (ER) for tumor growth and progression. The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β. Estrogens and estrogen receptors are implicated in a number of diseases or conditions, such as breast cancer, ovarian cancer, colon cancer, lung cancer, prostate cancer, endometrial cancer, uterine cancer, as well as others diseases or conditions.

Most breast cancer patients are treated with agents that either block estrogen synthesis (e.g., aromatase inhibitors; AIs) or antagonize the effects of estradiol via competitive ER binding (e.g., tamoxifen) (Puhalla S, et al Mol Oncol 2012; 6(2):222-236). Despite the well documented therapeutic utility of these agents in various stages of disease, many ER+ breast cancers recur and patients eventually succumb. Recently, next generation whole genome and targeted sequencing has identified ESR1 (estrogen receptor alpha gene) mutations in up to 20% of tumors from patients with advanced breast cancer who have progressed on endocrine therapies, largely aromatase inhibitors (Li S, et al. Cell Rep (2013); 4(6): 1116-1130; Merenbakh-Lamin K, et al. Cancer Res (2013); 73(23): 6856-6864; Robinson D R, et al. Nat Genet (2013); 45(12): 1446-1451; Toy W, et al. Nat Genet (2013); 45(12): 1439-1445; Jeselsohn R, et al. Clin Cancer Res (2014); 20: 1757-1767). These ligand-binding domain (LBD) mutations confer high basal activity of the apo-receptor rendering them ligand-independent and thus active in the setting of low estradiol. There is a tremendous need for therapies that target ER signaling with robust activity in the setting of progressive disease post AI or tamoxifen treatment including the subset of patients harboring ESR1 mutant tumors.

ARN-810 (GDC-0810, Seragon Pharmaceuticals, Genentech Inc.) is a potent small molecule, nonsteroidal, selective ER modulator that antagonizes the effects of estrogens and induces ER degradation via proteasome. ARN-810 is in clinical trials as an orally-delivered therapy to treat advanced metastatic ER-α positive (ER+) breast cancer.

Non-steroidal, Selective Estrogen Receptor Degraders (SERD) have been described (WO 2011/156518; U.S. Pat. No. 8,703,810; WO 2012/037411; WO 2012/037410; U.S. Pat. Nos. 8,299,112; 8,455,534; WO 2013/090829; WO 2013/142266; WO 2014/151899; WO 2013/090836; WO 2014/025138; WO 2014/205136).

SUMMARY OF THE INVENTION

Described herein, in certain embodiments, are methods for treating a hormone resistant-estrogen receptor (ER) positive breast cancer in a patient characterized as having a mutation in the ESR1 gene, comprising administering an estrogen receptor modulator (ERM). In some embodiments, the estrogen receptor modulator is a Selective Estrogen Receptor Degrader (SERD). In some embodiments, the estrogen receptor modulator is a selective estrogen receptor modulator (SERM). In some embodiments, the estrogen receptor modulator is a compound having the structure of Formula (A), (B), (C) or (D). In some embodiments, the compound having the structure of Formula (A) is a compound having the structure of Formula (A-1). In some embodiments, the compound having the structure of Formula (C) is a compound having the structure of Formula (C-1). In some embodiments, the compound having the structure of Formula (D) is a compound having the structure of Formula (D-1), (D-2), (D-3), (D-4), (D-5), or (D-6). In some embodiments, the mutation in the ESR1 gene results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C, In some embodiments, the patient has two or more mutations in the ESR1 gene.

Described herein in certain embodiments are methods for treating an ER-related disease or condition comprising administering an estrogen receptor modulator (ERM) compound of Formulas (A), (B), (C), or (D) to a patient having a mutation in the ESR1 gene.

The compound of Formula (A) has the structure:

Formula (A)

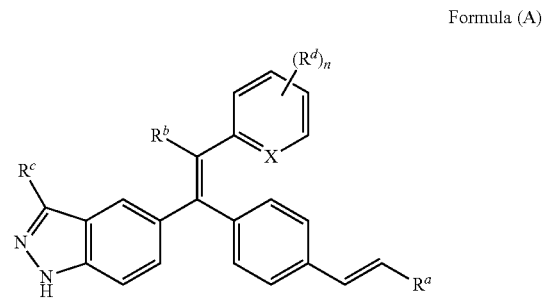

where, $R^a$ is —CO$_2$H or a 5-membered heterocycle selected from the group consisting of

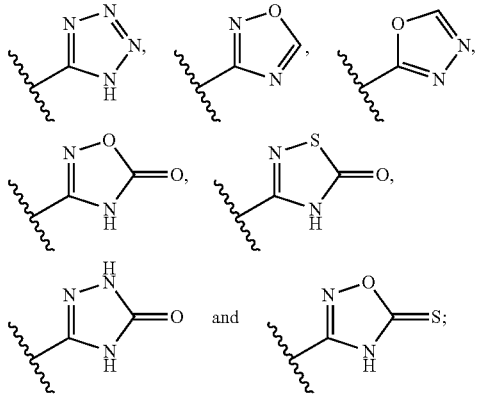

$R^b$ is C$_1$-C$_6$alkyl or C$_3$-C$_6$cycloalkyl;

$R^c$ is H or F;

each $R^d$ is independently selected from H, halogen, —CN, —OR$^e$, —NHR$^e$, —NR$^e$R$^f$, —SR$^e$, —S(=O)R$^f$, —S(=O)$_2$R$^f$, C$_1$-C$_6$alkyl, and C$_1$-C$_6$fluoroalkyl;

each $R^e$ is independently selected from H, —C(=O)R$^f$, —C(=O)OR$^f$, —C(=O)NHR$^f$, C$_1$-C$_6$ alkyl, C$_1$-C$_6$fluoroalkyl, C$_3$-C$_6$cycloalkyl, substituted or unsubstituted monocyclic C$_2$-C$_6$ heterocycloalkyl, substituted or unsubstituted phenyl, and substituted or unsubstituted monocyclic heteroaryl;

each $R^f$ is independently selected from C$_1$-C$_6$ alkyl, C$_1$-C$_6$ fluoroalkyl, C$_3$-C$_6$ cycloalkyl, substituted or unsubstituted monocyclic C$_2$-C$_6$ heterocycloalkyl, substituted or unsubstituted phenyl, and substituted or unsubstituted monocyclic heteroaryl;

X is CH or N; and n is 0, 1, or 2, or a pharmaceutically acceptable salt, or solvate thereof.

In some embodiments, the estrogen receptor modulator is a compound of Formula (A-1) having the structure:

Formula (A-1)

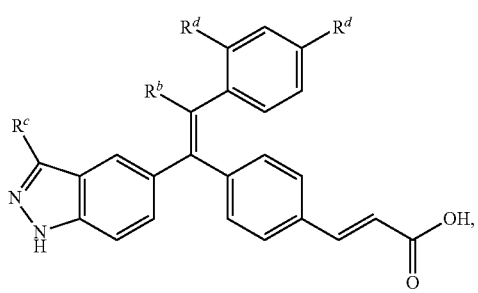

or a pharmaceutically acceptable salt, or solvate thereof.

In some embodiments, the estrogen receptor modulator is selected from among compound 1-1, 1-2, 1-3, 1-4, 1-5, 1-6, 1-7, 1-8, 1-9, 1-10, 1-11, and 1-12.

In some embodiments, the estrogen receptor modulator is 1-3.

The compound of Formula (B) has the structure:

Formula (B)

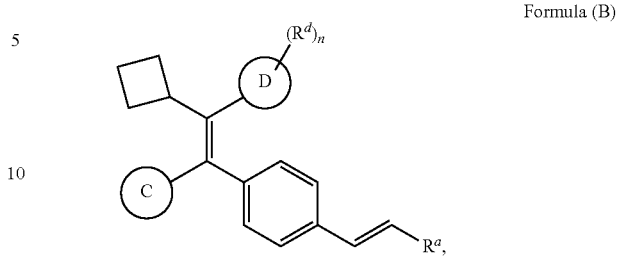

where, $R^a$ is —CO$_2$H or a 5-membered heterocycle selected from the group consisting of

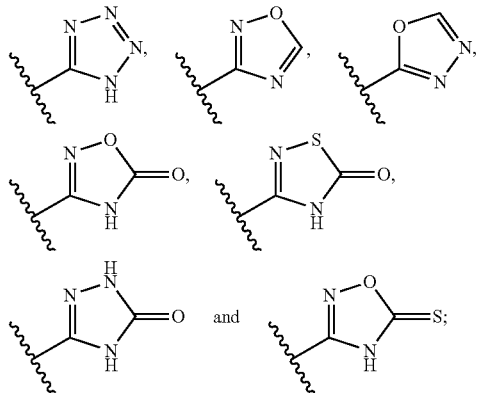

ring C is

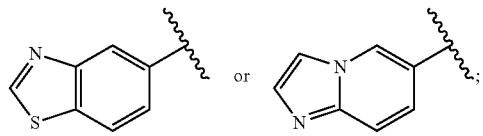 [SMILES: *c1ccc2scnc2c1 ; *c1ccc2nccn2c1]

ring D is phenyl or thienyl;

each $R^d$ is independently selected from H, halogen, —CN, —OR$^e$, —NHR$^e$, —NR$^e$R$^f$, —SR$^e$, —S(=O)R$^f$, —S(=O)$_2$R$^f$, C$_1$-C$_6$ alkyl, and C$_1$-C$_6$fluoroalkyl;

each $R^e$ is independently selected from H, —C(=O)R$^f$, —C(=O)OR$^f$, —C(=O)NHR$^f$, C$_1$-C$_6$ alkyl, C$_1$-C$_6$fluoroalkyl, C$_3$-C$_6$ cycloalkyl, substituted or unsubstituted monocyclic C$_2$-C$_6$ heterocycloalkyl, substituted or unsubstituted phenyl, and substituted or unsubstituted monocyclic heteroaryl;

each $R^f$ is independently selected from C$_1$-C$_6$ alkyl, C$_1$-C$_6$fluoroalkyl, C$_3$-C$_6$ cycloalkyl, substituted or unsubstituted monocyclic C$_2$-C$_6$heterocycloalkyl, substituted or unsubstituted phenyl, and substituted or unsubstituted monocyclic heteroaryl;

n is 0, 1, or 2, or a pharmaceutically acceptable salt, or solvate thereof

In some embodiments, the estrogen receptor modulator is selected from among compound 2-1, 2-2, 2-3, 2-4, and 2-5.

The compound of Formula (C) has the structure:

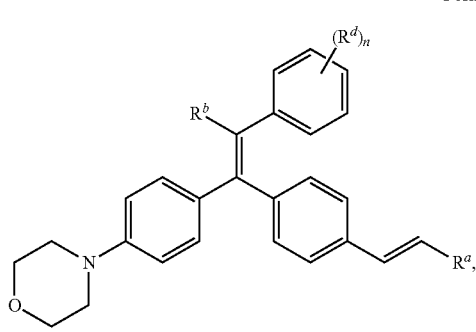

Formula (C)

where, $R^a$ is —$CO_2H$ or a 5-membered heterocycle selected from the group consisting of

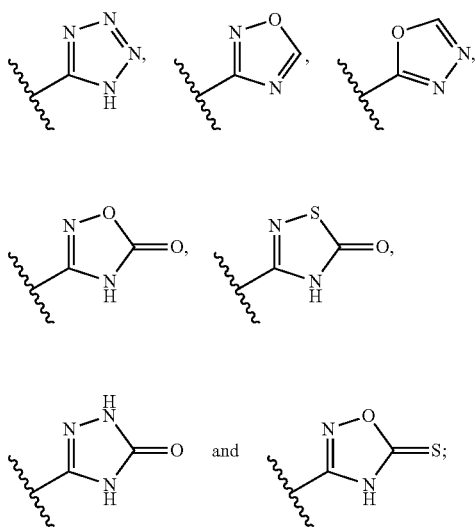

$R^b$ is $C_1$-$C_6$alkyl or $C_3$-$C_6$cycloalkyl;

each $R^d$ is independently selected from H, halogen, —CN, —$OR^e$, —$NHR^e$, —$NR^eR^f$, —$SR^e$, —$S(=O)R^f$, —$S(=O)_2R^f$, $C_1$-$C_6$alkyl, and $C_1$-$C_6$ fluoroalkyl;

each $R^e$ is independently selected from H, —$C(=O)R^f$, —$C(=O)OR^f$, —$C(=O)NHR^f$, $C_1$-$C_6$ alkyl, $C_1$-$C_6$fluoroalkyl, $C_3$-$C_6$ cycloalkyl, substituted or unsubstituted monocyclic $C_2$-$C_6$heterocycloalkyl, substituted or unsubstituted phenyl, and substituted or unsubstituted monocyclic heteroaryl;

each $R^f$ is independently selected from $C_1$-$C_6$ alkyl, $C_1$-$C_6$ fluoroalkyl, $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl; and n is 0, 1, or 2, or a pharmaceutically acceptable salt, or solvate thereof.

In some embodiments, the estrogen receptor modulator is a compound of Formula (C-1) having the structure:

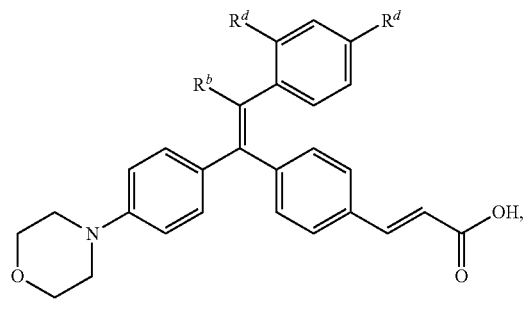

Formula (C-1)

or a pharmaceutically acceptable salt, or solvate thereof.

In some embodiments, the estrogen receptor modulator is compound 3-1, 3-2, 3-3, 3-4.

The compound of Formula (D) has the structure:

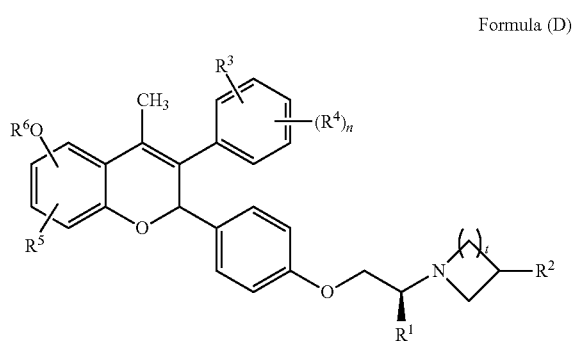

Formula (D)

where, $R^1$ is H, $C_1$-$C_4$ alkyl, or $C_1$-$C_4$ fluoroalkyl;

$R^2$ is H, F, $C_1$-$C_4$ alkyl or $C_1$-$C_4$ fluoroalkyl; $R^3$ is H, halogen, —CN, —$OR^6$, —$NHR^6$, —$NR^6R^7$, —$SR^6$, —$S(=O)R^7$, —$S(=O)_2R^7$, $C_1$-$C_4$alkyl, or $C_1$-$C_4$ fluoroalkyl;

each $R^4$ is independently selected from H, halogen, —CN, —OH, $C_1$-$C_6$ alkyl, $C_1$-$C_4$ fluoroalkyl, $C_1$-$C_4$fluoroalkoxy, and $C_1$-$C_4$alkoxy; each $R^5$ is H, F, Cl, —OH, —$CH_3$, —$CF_3$, or —$OCH_3$;

each $R^6$ is independently selected from H, —$C(=O)R^7$, —$C(=O)OR^7$, —$C(=O)NHR^7$, $C_1$-$C_6$alkyl, $C_1$-$C_6$ fluoroalkyl, $C_3$-$C_6$ cycloalkyl, substituted or unsubstituted $C_2$-$C_6$ heterocycloalkyl, substituted or unsubstituted phenyl, and substituted or unsubstituted monocyclic heteroaryl; each $R^7$ is independently selected from $C_1$-$C_6$ alkyl, $C_1$-$C_6$ fluoroalkyl, substituted or unsubstituted $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;

n is 0, 1, or 2; and t is 1 or 2, or a pharmaceutically acceptable salt, or solvate thereof.

In some embodiments, the estrogen receptor modulator is a compound of Formula (D-1) having the structure:

Formula (D-1)

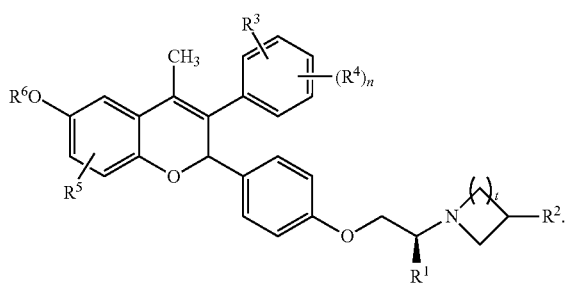

In some embodiments, the estrogen receptor modulator is a compound of Formula (D-2) having the structure:

Formula (D-2)

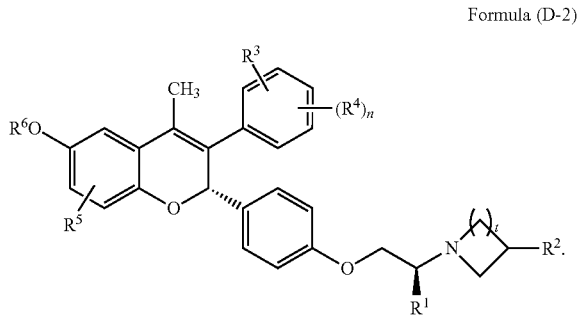

In some embodiments, the estrogen receptor modulator is a compound of Formula (D-3) having the structure:

Formula (D-3)

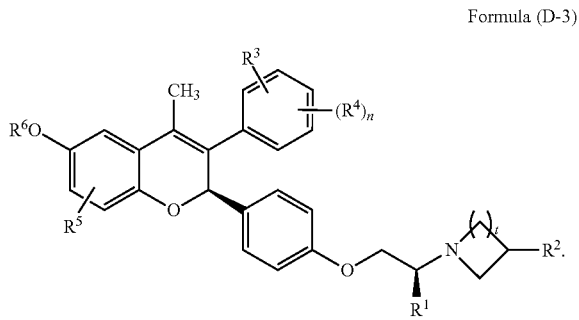

In some embodiments, the estrogen receptor modulator is a compound of Formula (D-4) having the structure:

Formula (D-4)

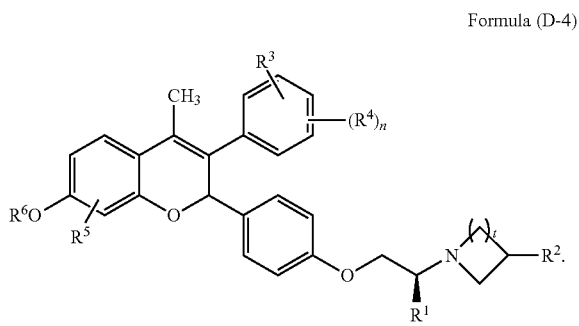

In some embodiments, the estrogen receptor modulator is selected from among compound 4-1, 4-2, 4-3, 4-4, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44 and 4-45.

In some embodiments, the estrogen receptor modulator is 4-23.

In some embodiments, the ER-related disease or condition is cancer. In some embodiments, the cancer is a breast cancer. In some embodiments, the breast cancer is a metastatic breast cancer. In some embodiments, the breast cancer is a hormone resistant breast cancer. In some embodiments, the breast cancer is an estrogen receptor positive breast cancer. In some embodiments, the breast cancer is a HER2 positive breast cancer. In some embodiments, the breast cancer is a HER2 negative breast cancer. In some embodiments, the breast cancer is resistant to treatment with an aromatase inhibitor. In some embodiments, the mutation in the ESR1 gene is a somatic mutation. In some embodiments, the patient expresses a wild-type ER and a mutant ER. In some embodiments, the patient expresses a homodimer of two mutant ER-α polypeptides. In some embodiments, the patient expresses a heterodimer of one wild-type ER-α polypeptide and one mutant ER-α polypeptide or a heterodimer of one wild-type ER-β polypeptide and one mutant ER-α polypeptide. In some embodiments, the patient has a tumor. In some embodiments, a plurality of cells of the tumor express the mutant ER. In some embodiments, the patient is pre-menopausal or post-menopausal. In some embodiments, the patient has failed one or more anti-cancer therapies. In some embodiments, the patient has received a chemotherapeutic agent, a biological therapy, a cancer vaccine, an angiogenesis inhibitor, hormone therapy, radiation therapy, surgery, or any combination thereof. In some embodiments, the biological therapy is a peptide, a cytokine, an antibody, a therapeutic virus, a therapeutic bacterium, gene therapy, siRNA, adoptive T-cell transfer, or any combination thereof. In some embodiments, the patient has received an aromatase inhibitor, a selective estrogen receptor modulator (SERM), a selective estrogen degrader (SERD), a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof. In some embodiments, the patient has received fulvestrant, tamoxifen, anastrozole, letrozole, exemestane, GDC0032, goserelin, leuprolide, raloxifene, toremifene, megestrol acetate, bazedoxifene, or any combination thereof. In some embodiments, the patient has received an anthracycline, a taxane, a platinum agent, an epothilone, or a nucleoside analog. In some embodiments, the patient has received cisplatin, carboplatin, capecitabine, cyclophosphamide, docetaxel, doxorubicin, epirubicin, eribulin, fluorouracil, gemcitabine, ixabepilone, mitoxantrone, methotrexate, paclitaxel, pamidronate, vinorelbine, or any combination thereof. In some embodiments, the patient has received pertuzumab, trastuzumab, lapatinib, everolimus, bevacizumab, temsirolimus, or any combination thereof. In some embodiments, the ESR1 mutation results in a substitution, insertion or deletion of one or more amino acids in the ER polypeptide. In some embodiments, the ESR1 mutation results in an amino acid substitution in the N-terminal domain, the DNA binding domain, the hinge region or the ligand binding domain of the estrogen receptor. In some embodiments, the ESR1 mutation results in an amino acid substitution in the ligand binding domain of the estrogen receptor. In some embodiments, the amino acid substitution is at amino acid position 6, 118, 269, 311, 341, 350, 380, 392, 394, 433, 463, 503, 534, 535, 536, 537, 538 and 555 of SEQ ID NO:2. In some embodiments, the amino acid substitution is selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the amino acid substitution is selected from among Y537N, Y537C, Y537S, and D538G. In some embodiments, the methods further comprise administration of one or more therapeutic agents for the treatment of the ER-related disease or condition. In some embodiments, the methods further comprise administration of an additional anti-cancer agent. In some embodiments, the methods further comprise administration of an aromatase inhibitor.

Described herein, in certain embodiments, are methods for selecting a patient having an ER-related disease or condition for treatment with a compound of Formula (A), (B), (C), or (D) comprising 1) detecting a mutation in the ESR1 gene in a sample comprising nucleic acid from the patient; and 2) selecting the patient for treatment with the compound if the patient has the ESR1 mutation.

In some embodiments, the nucleic acid is RNA or DNA. In some embodiments, the DNA is genomic DNA. In some embodiments, the method further comprises isolating mRNA from the nucleic acid sample. In some embodiments, the method further comprises amplifying a nucleic molecule comprising the mutation from the nucleic acid sample. In some embodiments, amplification is by polymerase chain reaction (PCR) or digital PCR. In some embodiments, PCR amplification comprises using a pair of oligonucleotide primers that flank the region comprising the mutation. In some embodiments, the methods comprise contacting the nucleic acid with a sequence specific nucleic acid probe, wherein the sequence specific nucleic acid probe that binds to the nucleic acid having the mutation and does not bind to the wild-type nucleic acid. In some embodiments, the sample comprises nucleic acid from one or more tumor cells. In some embodiments, the tumor cell is taken from a tumor biopsy sample, a blood sample, a serum sample, a lymph sample, or a bone marrow aspirate. In some embodiments, the tumor cell is a circulating tumor cell. In some embodiments, the sample comprises circulating tumor DNA (ctDNA).

Described herein, in certain embodiments, are kits comprising one or more reagents for the detection of a mutation in ESR1 and a compound of Formula (A), (B), (C), or (D). In some embodiments, the kits comprise one or more primers or probes for the detection of a mutation in ESR1. In some embodiments, the ESR1 mutation results in a substitution, insertion or deletion of one or more amino acids in the ER polypeptide. In some embodiments, the ESR1 mutation results in an amino acid substitution the N-terminal domain, the DNA binding domain, the hinge region or the ligand binding domain of the estrogen receptor. In some embodiments, the ESR1 mutation results in an amino acid substitution in the ligand binding domain of the estrogen receptor. In some embodiments, the amino acid substitution is at amino acid position 6, 118, 269, 311, 341, 350, 380, 392, 394, 433, 463, 503, 534, 535, 536, 537, 538 and 555 of SEQ ID NO:2. In some embodiments, the amino acid substitution is selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the amino acid substitution is selected from among Y537N, Y537C, Y537S, and D538G.

In some embodiments, the estrogen receptor modulator of Formula (A), (B), (C), (D) is administered orally to a patient. In some embodiments, the estrogen receptor modulator of Formula (A), (B), (C), (D) is administered daily. In some embodiments, the estrogen receptor modulator of Formula (A), (B), (C), (D) is administered on a continuous daily dosing schedule.

In some embodiments, the estrogen receptor modulator of Formula (A), (B), (C), (D) is administered at about 5 mg per day to about 1000 mg per day. In some embodiments, the therapeutically effective amount of an estrogen receptor modulator of Formula (A), (B), (C), (D) is about 10 mg per day to about 100 mg per day.

In some embodiments, the estrogen receptor modulator of Formula (A), (B), (C), (D) is administered once a day or multiple times a day. In some embodiments, the estrogen receptor modulator of Formula (A), (B), (C), (D) is administered once a day, twice a day, three times a day, or four times a day.

Other objects, features and advantages of the methods, uses and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Breast cancer is the most common form of cancer and the leading cause of cancer death in women worldwide. Approximately 80% of all breast cancers express and are dependent on the estrogen receptor (ER) for tumor growth and progression. Other cancers also are thought to be dependent on ER-α signaling for growth and survival, such as, for example, ovarian and endometrial cancers.

Estrogen receptor alpha (ER-α) and estrogen receptor beta (ER-β) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are unstable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S118) appears to control the transcriptional activity of ER in the presence of antagonists such as tamoxifen, which plays an important role in the treatment of breast cancer. While full agonists appear to arrest ER in certain conformations, weak agonists tend to maintain ER in equilibrium between different conformations, allowing cell-dependent differences in co-regulator repertoires to modulate the activity of ER in a cell-dependent manner (Tamrazi et al., *Mol. Endocrinol.* 17: 2593-2602, 2003). Interactions of ER with DNA are dynamic and are regulated by processes including, but are not limited to, the degradation of ER by the proteasome (Reid et al., *Mol Cell* 11: 695-707, 2003). The degradation of ER with ligands provides an attractive treatment strategy for disease or conditions that are estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc.

Modulation of estrogen activity and/or synthesis is the mainstay of therapeutic approaches in women with ER-positive (ER+) breast cancer. The ER-α antagonist tamoxifen has been used to treat early and advanced ER-α positive breast cancer in both pre- and post-menopausal women. Fulvestrant (FASLODEX™, Astra Zeneca) a steroid-based ER antagonist is used to treat breast cancer in women which has progressed despite therapy with tamoxifen. Steroidal and non-steroidal aromatase inhibitors are also used to treat cancers in humans. In some embodiments, the steroidal and non-steroidal aromatase inhibitors (e.g., anastrozole, letrozole and exemestane) block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracyclines, platins, taxanes. In some cases, ER positive breast cancers that harbor genetic amplification of the ERB-B/HER2 tyrosine kinase receptor are treated with the monoclonal antibody trastuzumab (HERCEPTIN™, Genentech Inc.) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as other therapies, are thought to remain dependent on ER-α for growth and survival. Thus, there is a need for new ER-α targeting agents that have activity in the setting of metastatic disease and acquired resistance.

Despite becoming refractory to aromatase inhibitors or tamoxifen, growth and survival of resistant tumor cells remain dependent on ER signaling; therefore, patients with ER+ breast cancer can still respond to second/third line hormonal treatment after progression on prior hormonal therapy. In some embodiments, in the endocrine resistant state, ER can signal in a ligand-independent manner. In some embodiments, an agent with a dual mechanism of action such as ER antagonism plus degradation has the potential to target both ligand-dependent and independent ER signaling and, consequently, improve treatment outcomes in late stage ER+ breast cancer.

Genomic analyses of tumor samples from hormone-resistant breast cancer patients have revealed mutations in the estrogen receptor alpha gene, ESR1, which contribute to hormone resistance in ER+ breast cancers. In certain instances, such mutations result in ligand-independent activation of the estrogen receptor. As described herein, particular ER modulator compounds are effective in inhibiting ER signaling in the ER mutant setting. Accordingly, such ER modulator compounds are useful for treating ER+ breast cancer patients having a mutant ER.

In certain instances, the ER mutation is a somatic mutation in the ESR1 gene. In some embodiments, the somatic mutation occurs in a cancer cell (e.g., a breast cancer cell) during the course of cancer treatment. In some embodiments, the patient has both a wild-type ESR1 gene and a mutant ESR1 gene (i.e., heterozygous). In some embodiments, a cancer cell undergoes somatic mutation to produce a mutant ESR1 gene. In some embodiments, the mutant cancer cell replicates to produce a plurality of mutant cancer cells, (e.g., an expanded population of cancer cells having the mutant ESR1 gene due to somatic mutation). In some embodiments, the patient expresses a wild-type ER-α and a mutant ER-α (i.e., heterogeneous expression). In some embodiments, the mutant ER-α comprises two mutant ER-α polypeptides (i.e., a homodimer). In some embodiments, the mutant ER-α comprises a wild-type ER-α polypeptide and a mutant ER-α. (i.e., a heterodimer). In some embodiments, the somatic mutation confers resistance of a cancer cell to a cancer treatment. In some embodiments, the somatic mutation in a plurality of cancer cells confers resistance of a patient to a cancer treatment. In some embodiments, the mutation confers resistance to hormone based therapies for treatment of a cancer (e.g., a breast cancer). In some embodiments, the cancer is an ER+ breast cancer.

In some embodiments, the ER mutation is a germline mutation in the ESR1 gene that is inherited. In some embodiments, the mutation increases the risk of developing breast cancer. In some embodiments, the germline mutation confers resistance of a cancer cell to a cancer treatment. In some embodiments, the germline mutation in a plurality of cancer cells (e.g., a breast cancer cells) confers resistance of a patient to a cancer treatment. In some embodiments, the germline mutation confers resistance to hormone based therapies for treatment of a cancer (e.g., a breast cancer). In some embodiments, the cancer is an ER+ breast cancer.

In one aspect, described herein are compounds that are estrogen receptor modulators for the treatment of patients having one or more mutations in the ESR1 gene. In some embodiments, the patient has one or more mutations in the ESR1 gene in one or more cancer cells, or a plurality of cancer cells. In some embodiments, the ER modulator compounds are selective estrogen receptor degraders (SERDs), which target ER-α for degradation. In some embodiments, the ER modulator compounds are selective estrogen receptor modulators (SERMs) having tissue specific ER properties.

In some embodiments, in cell-based assays the compounds described herein result in a reduction in steady state ER-α levels (e.g., ER degradation) and are useful in the treatment of estrogen sensitive diseases or conditions and/or diseases or conditions that have developed resistance to anti-hormonal therapies. In some embodiments, ER modulator compounds disclosed herein minimize levels of the estrogen receptor in the nucleus. In some embodiments, the ER modulator compound competes with estrogens for binding to the estrogen receptor. In some embodiments, the ER modulator compound is a non-steroidal ERα antagonist that competes with estrogens for binding to the estrogen receptor. In some embodiments, the ER modulator compound fully antagonizes the response of wild-type ER-α to estrogens. In some embodiments, the ER modulator compound fully antagonizes the response of mutant ER-α to estrogens. In some embodiments, the mutant ER-α exhibits increased basal activity compared to a wild-type ER-α. In some embodiments, the mutant ER-α exhibits ligand independent activity (e.g., constitutive activity). In some embodiments, the mutant ER-α exhibits constitutive activity in the absence of estradiol. In some embodiments, the ER modulator inhibits the ligand independent activity (e.g., constitutive activity) of a mutant ER-α. In some embodiments, the ER modulator induces a conformational change in a mutant ER-α. In some embodiments, the ER modulator induces a conformational change in a mutant ER-α that inhibits the activity of the mutant ER-α. In some embodiments, the ER modulator induces proteasomal degradation of wild-type ER-α in breast cancer cells. In some embodiments, the ER modulator induces proteasomal degradation of mutant ER-α in breast cancer cells. In some embodiments, the ER modulator inhibits a mutant ER-α in breast cancer cells independent of proteasomal degradation. In some embodiments, the ER modulator compound fully antagonizes the response of ER-α to estrogens and induces proteasomal degradation of wild-type ER-α in breast cancer cells. In some embodiments, the ER modulator compound fully antagonizes the response of a mutant ER-α to estrogens and induces proteasomal degradation of the mutant ER-α in breast cancer cells. In some embodiments, the ER modulator compound fully antagonizes the response of a mutant ER-α to estrogens and does not induce proteasomal degradation of the mutant ER-α in breast cancer cells. In some embodiments, the ER modulator compound inhibits the proliferation of breast cancer cells expressing a mutant ER-α. In some embodiments, the ER modulator compound displays good oral bioavailability.

The ER modulator compounds disclosed herein are useful in the treatment of hormone resistant ER-positive breast cancer characterized by one or more mutations in the ESR1 gene, either alone or in combination with other agent agents that modulate other critical pathways in breast cancer, including but not limited to those that inhibit IGF1R, EGFR, Erb-B2, Erb-B3, the PI3K/AKT/mTOR pathway, HSP90, PARP, cyclin dependent kinase (i.e. CDK 4/6), VEGF receptor or histone deacetylases. In some embodiments, the ER modulator compounds disclosed herein are useful in the treatment of hormone resistant ER-positive breast cancer characterized by one or more mutations in the ESR1 gene, either alone or in combination with other agents used to treat breast cancer, including but not limited to, aromatase inhibitors, anthracycline, platins, nitrogen mustard, alkylating agents, taxanes, nucleoside analogs, a phosphoinositide 3-kinase (PI3K)/mTOR pathway inhibitor, CDK 4/6 inhibitors, HER-2 inhibitors, EGFR inhibitors, PD-1 inhibitors, poly ADP-ribose polymerase (PARP) inhibitors, histone deacetylase (HDAC) inhibitors, HSP90 inhibitors, VEGFR inhibitors, AKT inhibitors, and chemotherapy. Illustrative agents used to treat breast cancer, include, but are not limited to, fulvestrant, tamoxifen, anastrozole, letrozole, exemestane, GDC-0032, GDC-0068, goserelin, leuprolide, raloxifene, toremifene, megestrol acetate, bazedoxifene, cisplatin, carboplatin, capecitabine, cyclophosphamide, docetaxel, doxorubicin, epirubicin, eribulin, filgrastim, fluorouracil, gemcitabine, ixabepilone, LEE011, LY2835219, mitoxantrone, methotrexate, paclitaxel, pamidronate, vinorelbine, pegfilgrastim, pertuzumab, trastuzumab, lapatinib, everolimus, bevacizumab, temsirolimus, and combinations thereof, as well as others described herein. Additional non-limiting exemplary agents for the treatment of breast cancer are provided elsewhere herein.

DEFINITIONS

Figure 1:
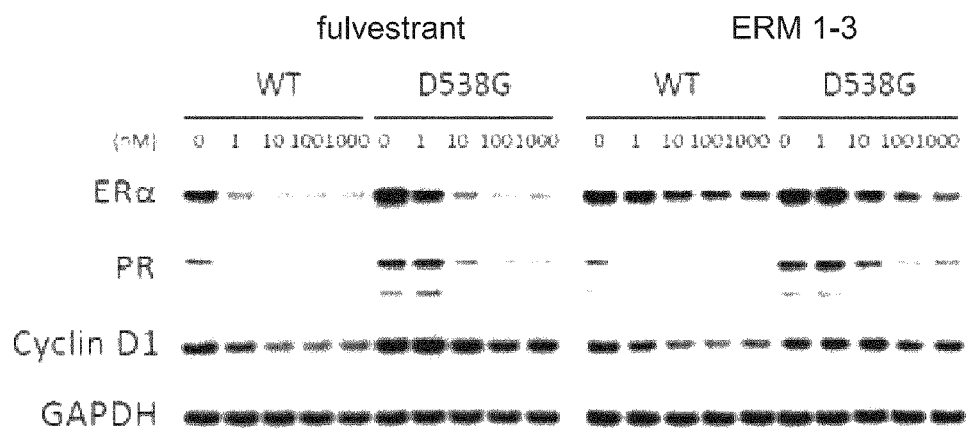
FIGS. 1 and 2 show ERα degradation assay in MCF7 inducibly expressing WT and mutant ERα in the absence of E2 (ethinyl estradiol). Cells were treated with increasing doses of fulvestrant (FIG. 1) for 24 hr in the estrogen-depleted medium containing 100 ng/ml Dox (doxorubicin). Mutant ERα degradation was observed with estrogen receptor modulator (ERM) 1-3 from Table 1 (FIG. 1) and ERM 4-23 (FIG. 2), but not tamoxifen (FIG. 2). Functional output is evident by the PR and cyclin D1 levels.

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 5 μg" means "about 5 μg" and also "5 μg." Generally, the term "about" includes an amount that would be expected to be within experimental error.

As used herein, an "estrogen receptor polypeptide" or "ER polypeptide" refers to any estrogen receptor protein or polypeptide, including, but not limited to, a recombinantly produced protein, a synthetically produced protein, a native estrogen receptor protein, and an estrogen receptor protein extracted from cells or tissues. An ER polypeptide includes related polypeptides from different species including, but not limited to animals of human and non-human origin. ER polypeptides of non-human origin include, but are not limited to, non-human primate (e.g. chimpanzee and ape), murine (e.g., mouse and rat), canine (dog), feline (cat), leporine (rabbit), avian (bird), bovine (cow), ovine (sheep), porcine (pig), equine (horse), piscine (fish), ranine (frog) and other mammalian or non-mammalian ER polypeptides. Exemplary ER polypeptides include, for example, SEQ ID NO:2. An ER polypeptide includes wild-type ER, allelic variant isoforms, somatic mutations including those found in tumors, synthetic molecules from nucleic acids, protein isolated from human tissue and cells, and modified forms thereof. The ER polypeptides provided herein can be further modified by modification of the primary amino acid sequence, by deletion, addition, or substitution of one or more amino acids. As used herein, ER proteins include monomeric and dimeric forms of ER polypeptides, including dimeric forms of ER-α and ER-13 polypeptides (e.g., ER-α (αα) or ER-β (ββ) homodimers or ERαβ (αβ) heterodimers).

As used herein, a "mutant estrogen receptor" or "mutant ER" refers to any estrogen receptor protein or polypeptide that is modified by modification of the primary amino acid sequence, by deletion, addition, or substitution of one or more amino acids compared to a wild-type ER. In some embodiments, a mutant ER comprises a heterodimer of a mutant ER polypeptide and a wild-type polypeptide. In some embodiments, a mutant estrogen receptor (ER) comprises a homodimer of two mutant ER polypeptides.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. As used herein, an estrogen receptor (ER) modulator is a molecule that interacts with an estrogen receptor (e.g., ER-α). In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues. In some embodiments, a SERM displays ER degradation properties. In some embodiments, a SERM displays ER degradation properties in some tissues and no ER degradation properties in other tissues. In some embodiments, a SERM displays ER degradation and ER antagonist properties. In some embodiments, a SERM displays ER degradation and ER antagonist properties in some tissues and ER degradation but no ER agonist activity in other tissues. In some embodiments, a SERM displays ER degradation and ER antagonist properties in some tissues and ER degradation and ER antagonist properties but no ER degradation properties in other tissues. In some embodiments, a SERM displays ER degradation and ER antagonist properties in breast tissues, ovarian tissues, endometrial tissues, and/or cervical tissues but minimal or no ER degradation and/or ER antagonist properties in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90%, at least 95%, at least 96%, at least 97%, at least 98%, or at least 99%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that would not occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases. In some embodiments, the cancer is a carcinoma (e.g., an adenocarcinoma) or a sarcoma.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The term "breast cancer" as used herein refers to histologically or cytologically confirmed cancer of the breast. In some embodiments, the breast cancer is a carcinoma. In some embodiments, the breast cancer is an adenocarcinoma. In some embodiments, the breast cancer is a sarcoma.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer is also referred to as stage IV breast cancer.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, treatment includes extending progression-free survival. In some embodiments, treatment includes reducing the relative risk of disease progression compared to other treatment options. In some embodiments, other treatment options include but are not limited to hormonal treatments (e.g., anti-estrogen therapy, such as tamoxifen and/or fulvestrant or aromatase therapy).

The term "progression-free survival" is the amount of time during and after the treatment of a disease, such as cancer, that a patient lives with the disease but it does not get worse. In a clinical trial, measuring progression-free survival is one way to see how well a treatment works.

The term "metastasis-free survival" or "MFS" refers to the percentage of subjects in a study who have survived without cancer spread for a defined period of time or death. MFS is usually reported as time from the beginning of treatment in the study. MFS is reported for an individual or a study population. In some embodiments, the increase in the metastasis-free survival is about 1 month, about 2 months, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (A), (B), (C) or (D), and a co-agent, are both administered to a patient simultaneously in the form of a single entity or dosage. The term "non-fixed combination" means that the active ingredients, e.g. a compound of Formula (A), (B), (C) or (D), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutically acceptable" as used herein, refers to a material, (e.g., a carrier or diluent), which does not abrogate the biological activity or properties of an ER inhibitor compound described herein, and is relatively non-toxic (i.e., the material is administered to an individual without causing undesirable biological effects or interacting in a deleterious manner with any of the components of the composition in which it is contained).

As used herein, a "control" refers to a sample that is substantially identical to the test sample, except that it is not treated with a test parameter, or, if it is a plasma sample, it can be from a normal volunteer not affected with the condition of interest. A control also can be an internal control.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject can be any animal, including mammals (e.g., a human or non-human animal, e.g., chimpanzees, apes, monkeys, cattle, horses, sheep, goats, swine, rabbits, dogs, cats, rats, mice, guinea pigs, and the like) and non-mammals. In one embodiment of the methods and compositions provided herein, the mammal is a human.

The term "continuous daily dosing schedule" refers to the administration of an estrogen receptor modulator, or a pharmaceutically acceptable salt thereof, daily without any drug holidays. In some embodiments, a continuous daily dosing schedule comprises administration of an estrogen receptor modulator, or a pharmaceutically acceptable salt thereof, every day at roughly the same time each day.

An "alkyl" group refers to an aliphatic hydrocarbon group. The alkyl moiety may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, and the like. In some embodiments, 1 or more hydrogen atoms of an alkyl are replaced with 1 or more deuterium atoms.

An "alkoxy" group refers to a (alkyl)O— group, where alkyl is as defined herein. The term "aromatic" refers to a planar ring having a delocalized π-electron system containing 4n+2π electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. In one aspect, an aryl is a phenyl or a naphthalenyl. In one aspect, an aryl is a phenyl. In one aspect, an aryl is a $C_6$-$C_{10}$aryl. In some embodiments, 1 or more hydrogen atoms of an aryl are replaced with 1 or more deuterium atoms The term "cycloalkyl" refers to a cyclic aliphatic hydrocarbon radical. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. In one aspect, a cycloalkyl is a $C_3$-$C_6$cycloalkyl.

The term "halo" or, alternatively, "halogen" or "halide" means fluoro (F), chloro (Cl), bromo (Br) or iodo (I). In some embodiments, halogen is F or Cl. In some embodiments, halogen is F.

The term "fluoroalkyl" refers to an alkyl in which one or more hydrogen atoms are replaced by a fluorine atom. In one aspect, a fluoralkyl is a $C_1$-$C_6$ fluoroalkyl. In some embodiments, a fluoroalkyl is a monofluoroalkyl, wherein one hydrogen atom of the alkyl is replaced by a fluorine atom. In some embodiments, a fluoroalkyl is a difluoroalkyl, wherein two hydrogen atoms of the alkyl are replaced by a fluorine atom. In some embodiments, a fluoroalkyl is a trifluoroalkyl, wherein three hydrogen atom of the alkyl are replaced by a fluorine atom. In some embodiments, a fluoroalkyl is a monofluoroalkyl, difluoroalkyl, or trifluoroalkyl. In some embodiments, a monofluoroalkyl is —$CH_2F$, —$CHF_2$, —$CF_3$, —$CHFCH_3$, —$CH_2CH_2F$, —$CH_2CHF_2$, —$CH_2CF_3$, —$CH_2CH_2CF_3$, —$CH_2CH_2CH_2CF_3$, —$CHCH_3CF_3$, —$CH(CF_3)_2$, or —$CF(CH_3)_2$.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached (or C-linked) or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems.

The terms "heteroaryl" refers to an aryl group that includes one or more ring heteroatoms selected from nitrogen, oxygen and sulfur. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, monocyclic heteroaryl is a 5-membered or 6-membered heteroaryl. A "heterocycloalkyl" or "heteroalicyclic" group refers to a cycloalkyl group wherein at least one of the carbon atoms of the cycloalkyl is replaced with nitrogen (unsubstituted or substituted, e.g. —NH—, —$NR^e$—), oxygen (—O—), or sulfur (e.g. —S—, —S(=O)— or —S(=O)$_2$—). The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

Exemplary Estrogen Receptor Mutants for Diagnosis and Treatment

In some embodiments, the diagnostic methods provided herein comprise detecting one or more mutations in the ESR1 gene. In some embodiments, the methods provided herein comprise treating a patient having one or more mutations in the ESR1. Exemplary ESR1 mutations for diagnosis and treatment include, but are not limited to, nucleotide insertions, deletions or substitutions. In some embodiments, the mutation is a nucleotide substitution that results in the substitution of an amino acid in the encoded ER polypeptide (i.e., a missense mutation). In some embodiments, the mutation is a nucleotide insertion that results in an insertion of an amino acid and/or substitution of one or more amino acids in the encoded ER polypeptide. In some embodiments, the mutation is a nucleotide deletion that results in a deletion of an amino acid and/or substitution of one or more amino acids in the encoded ER polypeptide. In some embodiments, the mutation is a genomic translocation that results in a hybrid ER polypeptide where one or more domains of the ER polypeptide are fused to another protein or a portion thereof. In some embodiments, the mutation is a nucleotide insertion, deletion, or substitution that results in a truncated ER polypeptide (i.e., a nonsense mutation). In some embodiments, the ESR1 mutation results in increases in the activity of the encoded mutant ER-α polypeptide. In some embodiments, the mutation confers ligand-independent activation of the encoded mutant ER-α polypeptide. In some embodiments, the mutation results in a constitutively-active mutant ER-α polypeptide. In some embodiments, the mutant ER-α exhibits constitutive activity in the absence of estradiol. In some embodiments, the ESR1 mutation increases the expression of the ESR1 gene product (i.e., increases the expression of the wild-type ER-α polypeptide).

In some embodiments, the mutation results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, the mutation results in an ER polypeptide having an amino acid substitution at a position selected from among amino acids positions 380, 463, 534, 535, 536, 537, and 538 of SEQ ID NO:2. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene.

In some embodiments, the ESR1 mutation includes a missense mutation in the ESR1 gene that causes an amino acid substitution at position 6 of SEQ ID NO:2. In some embodiments, the amino acid substitution is a H6Y substitution. In some embodiments, the missense mutation is a C16T substitution in the codon encoding H6 according to the nucleotide sequence of SEQ ID NO:1 (e.g., CAC to TAC).

In some embodiments, the ESR1 mutation includes a missense mutation in the ESR1 gene that causes an amino acid substitution at position 118 of SEQ ID NO:2. In some embodiments, the amino acid substitution is a S118P substitution. In some embodiments, the missense mutation is a T352C substitution in the codon encoding S118 according to the nucleotide sequence of SEQ ID NO:1 (e.g., TCG to CCG).

In some embodiments, the ESR1 mutation includes a missense mutation in the ESR1 gene that causes an amino acid substitution at position 269 of SEQ ID NO:2. In some embodiments, the amino acid substitution is a R269C substitution. In some embodiments, the missense mutation is a C805T substitution in the codon encoding S269 according to the nucleotide sequence of SEQ ID NO:1 (e.g., CGC to TGC).

In some embodiments, the ESR1 mutation includes a missense mutation in the ESR1 gene that causes an amino acid substitution at position 311 of SEQ ID NO:2. In some embodiments, the amino acid substitution is a T311M substitution. In some embodiments, the missense mutation is a C932T substitution according to the nucleotide sequence of SEQ ID NO:1.

In some embodiments, the ESR1 mutation includes a missense mutation in the ESR1 gene that causes an amino acid substitution at position 341 of SEQ ID NO:2. In some embodiments, the amino acid substitution is a S341L substitution. In some embodiments, the missense mutation is a C1022T substitution according to the nucleotide sequence of SEQ ID NO:1.

In some embodiments, the ESR1 mutation includes a missense mutation in the ESR1 gene that causes an amino acid insertion between amino acids G344 and L345 of SEQ ID NO:2. In some embodiments, the amino acid insertion is C amino acid. In some embodiments, the missense mutation an insertion of nucleotides GCT between nucleotides 1032 and 1033 of SEQ ID NO:1.

In some embodiments, the ESR1 mutation includes a missense mutation in the ESR1 gene that causes an amino acid substitution at position 350 of SEQ ID NO:2. In some embodiments, the amino acid substitution is a A350E substitution. In some embodiments, the missense mutation is a C1049A substitution according to the nucleotide sequence of SEQ ID NO:1.

In some embodiments, the ESR1 mutation includes a missense mutation in the ESR1 gene that causes an amino acid substitution at position 380 of SEQ ID NO:2. In some embodiments, the amino acid substitution is a E380Q substitution. In some embodiments, the missense mutation is a G1138C substitution in the codon encoding E380 according to the nucleotide sequence of SEQ ID NO: 1 (e.g., GAA to CAA).

In some embodiments, the ESR1 mutation includes a missense mutation in the ESR1 gene that causes an amino acid substitution at position 392 of SEQ ID NO:2. In some embodiments, the amino acid substitution is a V392I substitution. In some embodiments, the missense mutation is a G1174A substitution in the codon encoding V392 according to the nucleotide sequence of SEQ ID NO:1 (e.g., GTC to ATC).

In some embodiments, the ESR1 mutation includes a missense mutation in the ESR1 gene that causes an amino acid substitution at position 394 of SEQ ID NO:2. In some embodiments, the amino acid substitution is a R394H substitution. In some embodiments, the missense mutation is a G1181A substitution according to the nucleotide sequence of SEQ ID NO:1.

In some embodiments, the ESR1 mutation includes a missense mutation in the ESR1 gene that causes a truncated protein that ends at position 413 of SEQ ID NO:2. In some embodiments, the amino acid truncation is a Q414* mutation, due to a mutation in the nucleotide sequence that introduces a stop codon. In some embodiments, the mutation is a C1240T substitution according to the nucleotide sequence of SEQ ID NO:1.

In some embodiments, the ESR1 mutation includes a missense mutation in the ESR1 gene that causes an amino acid substitution at position 433 of SEQ ID NO:2. In some embodiments, the amino acid substitution is a S433P substitution. In some embodiments, the missense mutation is a T1297C substitution according to the nucleotide sequence of SEQ ID NO:1.

In some embodiments, the ESR1 mutation includes a missense mutation in the ESR1 gene that causes an amino acid substitution at position 463 of SEQ ID NO:2. In some embodiments, the amino acid substitution is a S463P substitution. In some embodiments, the missense mutation is a T1387C substitution in the codon encoding 5463 according to the nucleotide sequence of SEQ ID NO:1 (e.g., TCC to CCC).

In some embodiments, the ESR1 mutation includes a missense mutation in the ESR1 gene that causes an amino acid substitution at position 503 of SEQ ID NO:2. In some embodiments, the amino acid substitution is a R503W substitution. In some embodiments, the missense mutation is a C1507T substitution according to the nucleotide sequence of SEQ ID NO:1.

In some embodiments, the ESR1 mutation includes a missense mutation in the ESR1 gene that causes an amino acid substitution at position 534 of SEQ ID NO:2. In some embodiments, the amino acid substitution is a V534E substitution. In some embodiments, the missense mutation is a T1601A substitution in the codon encoding V534 according to the nucleotide sequence of SEQ ID NO:1 (e.g., GTG to GAG).

In some embodiments, the ESR1 mutation includes a missense mutation in the ESR1 gene that causes an amino acid substitution at position 535 of SEQ ID NO:2. In some embodiments, the amino acid substitution is a P535H substitution. In some embodiments, the missense mutation is a C1604A substitution in the codon encoding P535 according to the nucleotide sequence of SEQ ID NO:1 (e.g., CCC to CAC).

In some embodiments, the ESR1 mutation includes a missense mutation in the ESR1 gene that causes an amino acid substitution at position 536 of SEQ ID NO:2. In some embodiments, the amino acid substitution is a L536R substitution. In some embodiments, the amino acid substitution is a L536P substitution. In some embodiments, the amino acid substitution is a L536Q substitution. In some embodiments, the missense mutation is a T1607A substitution and a C1608A substitution in the codon encoding L536 according to the nucleotide sequence of SEQ ID NO:1 (e.g., CTC to CAA).

In some embodiments, the ESR1 mutation includes a missense mutation in the ESR1 gene that causes an amino acid substitution at position 537 of SEQ ID NO:2. In some embodiments, the amino acid substitution is a Y537N substitution. In some embodiments, the amino acid substitution is a Y537C substitution. In some embodiments, the amino acid substitution is a Y537S substitution. In some embodiments, the missense mutation is a T1609A substitution according to the nucleotide sequence of SEQ ID NO:1. In some embodiments, the missense mutation is a A1610G substitution according to the nucleotide sequence of SEQ ID NO:1.

In some embodiments, the ESR1 mutation includes a missense mutation in the ESR1 gene that causes an amino acid substitution at position 538 of SEQ ID NO:2. In some embodiments, the amino acid substitution is a D538G substitution. In some embodiments, the missense mutation is a A1613G substitution according to the nucleotide sequence of SEQ ID NO:1.

In some embodiments, the ESR1 mutation includes a missense mutation in the ESR1 gene that causes an amino acid substitution at position 555 of SEQ ID NO:2. In some embodiments, the amino acid substitution is a R555C substitution. In some embodiments, the missense mutation is a C1663T substitution in the codon encoding R555 according to the nucleotide sequence of SEQ ID NO:1 (e.g., CGT to TGT).

In some embodiments, the ESR1 mutation is a deletion in the ligand binding domain of the ESR1 gene. In some embodiments, the ESR1 mutation is an in frame deletion of 3 or more nucleotides. In some embodiments, the mutation is an in frame deletion of 3 or more nucleotides in one or more ESR1 exons. In some embodiments, the mutation is an in frame deletion of 3 or more nucleotides in an exon 8, 9, 10, 11, or 12 of the ESR1 gene. In some embodiments, the ESR1 mutation is a 6 nucleotide deletion of nucleotides 1046-1051 (TGGCAG) according to SEQ ID NO:1, which results in the deletion of amino acids 349-351 (LAD) and an insertion of H at amino acid position 349 of an ER polypeptide of SEQ ID NO:2.

In some embodiments, the missense mutation in the ESR1 gene results in an amino acid substitution selected from one or more of: a histidine to tyrosine substitution at position 6 (H6Y); a serine to proline substitution at position 118 (S118P); an arginine to cysteine substitution at position 269 (R269C); a threonine to methionine substitution at position 311 (T311M); a serine to leucine substitution at position 341 (S341L); an alanine to glutamate substitution at position 350 (A350E); a glutamic acid to glutamine substitution at position 380 (E380Q); a valine to isoleucine substitution at position 392 (V392I); an arginine to histidine substitution at position 394 (R394H); a glutamine substitution at position 414, e.g., an insertion to a stop codon (Q414*); a serine to proline substitution at position 433 (S433P); a serine to proline substitution at position 463 (S463P); an arginine to tryptophan substitution at position 503 (R503W); a valine to glutamic acid substitution at position 534 (V534E); a proline to histidine substitution at position 535 (P535H); a leucine to arginine substitution at position 536 (L536R); a leucine to proline substitution at position 536 (L536P); a leucine to glutamine substitution at position 536 (L536Q); a tyrosine to asparagine substitution at position 537 (Y537N); a tyrosine to cysteine substitution at position 537 (Y537C); a tyrosine to serine substitution at position 537 (Y537S); an aspartate to glycine substitution at position 538 (D538G); and an arginine to cysteine substitution at position 555 (R555C), of SEQ ID NO:2.

In some embodiments, the ESR1 mutation is a genomic translocation between the ESR1 gene and the yes activated protein 1 (YAP1) gene that results in a ER-YAP1 fusion protein.

In some embodiments, the ESR1 gene comprises two or more mutations. In some embodiments, the ESR1 gene comprises two or more mutations in the hinge domain and/or the ligand binding domain.

Estrogen Receptor Modulator Compounds

Provided herein are estrogen receptor modulator (ERM) compounds for treatment of a subject having a mutation in the ESR1 gene. In some embodiments, estrogen receptor modulator compound is a compound of Formula (A), (B), (C), or (D) including pharmaceutically acceptable salts, solvates, N-oxides, metabolites and prodrugs thereof.

In one aspect, the estrogen receptor modulator compound for use in the methods and compositions described herein is a compound of Formula (A), or a pharmaceutically acceptable salt, or solvate thereof:

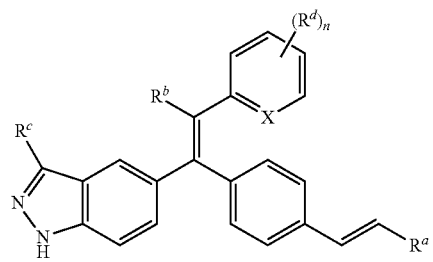

Formula (A)

wherein, $R^a$ is —CO$_2$H or a 5-membered heterocycle selected from the group consisting of

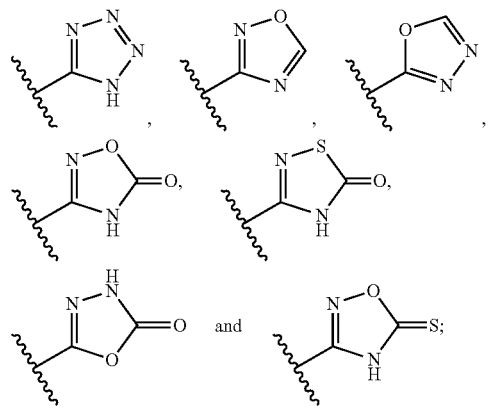

$R^b$ is $C_1$-$C_6$ alkyl or $C_3$-$C_6$ cycloalkyl;

$R^c$ is H or F;

each $R^d$ is independently selected from H, halogen, —CN, —OR$^e$, —NHR$^e$, —NR$^e$R$^f$, —SR$^e$, —S(=O)R$^f$, —S(=O)$_2$R$^f$, $C_1$-$C_6$alkyl, and $C_1$-$C_6$fluoroalkyl;

each $R^e$ is independently selected from H, —C(=O)R$^f$, —C(=O)OR$^f$, —C(=O)NHR$^f$, $C_1$-$C_6$ alkyl, $C_1$-$C_6$fluoroalkyl, $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;

each $R^f$ is independently selected from $C_1$-$C_6$ alkyl, $C_1$-$C_6$ fluoroalkyl, $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;

X is CH or N;

n is 0, 1, or 2.

In some embodiments, $R^a$ is —CO$_2$H. In some embodiments, $R^a$ is a 5-membered heterocycle selected from the group consisting of

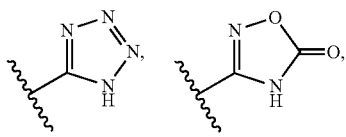

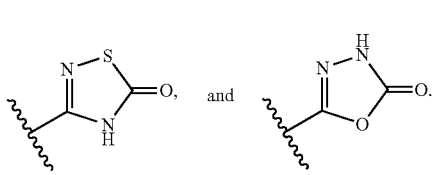

and

In some embodiments, $R^c$ is H. In some embodiments, $R^c$ is F.

In some embodiments, $R^b$ is —CH$_3$, —CH$_2$CH$_3$, cyclopropyl, or cyclobutyl. In some embodiments, $R^b$ is —CH$_2$CH$_3$. In some embodiments, $R^b$ is cyclobutyl.

In some embodiments X is CH. In some embodiments X is N.

In some embodiments, n is 1 or 2. In some embodiments, n is 1. In some embodiments, n is 2. In some embodiments, n is 0.

In some embodiments, each $R^d$ is independently selected from H, F, Cl, —CN, —OH, —OCH$_3$, —OCH$_2$CH$_3$, —S(=O)$_2$CH$_3$, —CH$_3$, —CH$_2$H$_3$, and —CF$_3$. In some embodiments, each $R^d$ is independently selected from H, F, Cl, —CN, —OH, —OCH$_3$, —OCH$_2$CH$_3$, —CH$_3$, —CH$_2$H$_3$, and —CF$_3$.

In some embodiments, the estrogen receptor modulator compound of Formula (A) has the following structure of Formula (A-1), or a pharmaceutically acceptable salt, or solvate thereof:

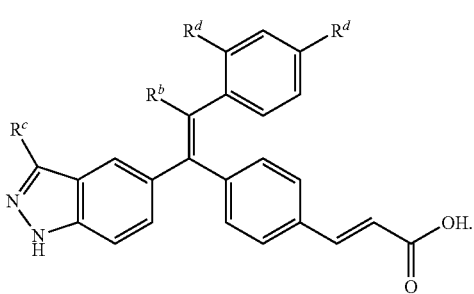

Formula (A-1)

In some embodiments, the estrogen receptor modulator compound of Formula (A) is a compound described in Table 1, or a pharmaceutically acceptable salt, or solvate thereof:

TABLE 1

| ERM Compound No. | Name | Structure |
|---|---|---|
| 1-1 | (E)-3-(4-((E)-2-(2,4-dichlorophenyl)-1-(1H-indazol-5-yl)but-1-en-1-yl)phenyl)acrylic acid | 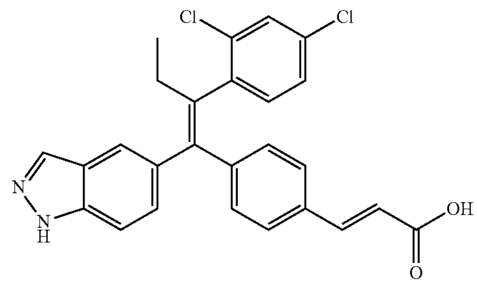 |
| 1-2 | (E)-3-(4-((E)-2-(2,4-difluorophenyl)-1-(1H-indazol-5-yl)but-1-en-1-yl)phenyl)acrylic acid | 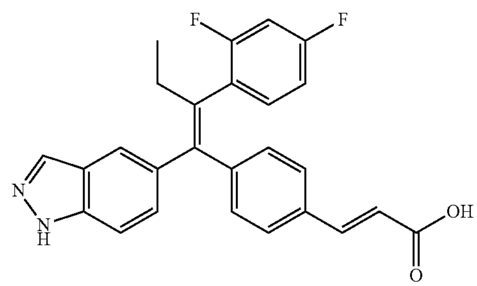 [SMILES: CC/C(=C(/c1ccc(/C=C/C(=O)O)cc1)c1ccc2[nH]ncc2c1)c1ccc(F)cc1F] |
| 1-3 | (E)-3-(4-((E)-2-(2-chloro-4-fluorophenyl)-1-(1H-indazol-5-yl)but-1-en-1-yl)phenyl)acrylic acid | 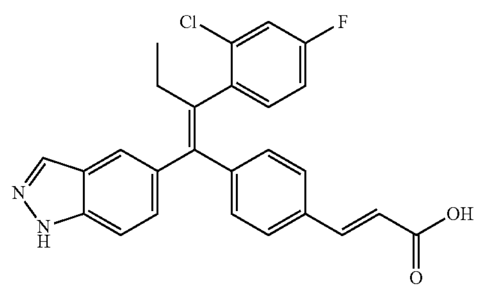 [SMILES: CC/C(=C(/c1ccc(/C=C/C(=O)O)cc1)c1ccc2[nH]ncc2c1)c1ccc(F)cc1Cl] |
| 1-4 | (E)-3-(4-((E)-2-(2-chloro-4-fluorophenyl)-1-(3-fluoro-1H-indazol-5-yl)but-1-en-1-yl)phenyl)acrylic acid | 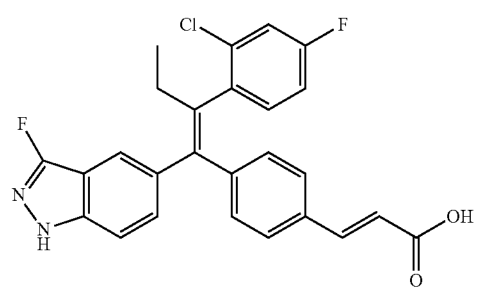 [SMILES: CC/C(=C(/c1ccc(/C=C/C(=O)O)cc1)c1ccc2[nH]nc(F)c2c1)c1ccc(F)cc1Cl] |
| 1-5 | (E)-3-(4-((E)-2-(2-chloro-4-fluorophenyl)-2-cyclobutyl-1-(1H-indazol-5-yl)vinyl)phenyl)acrylic acid | 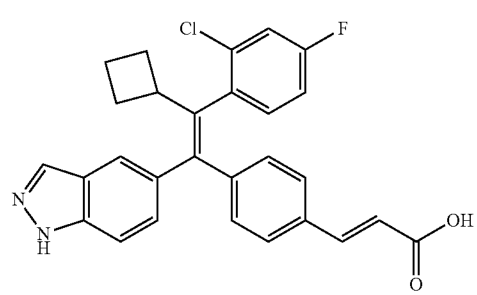 [SMILES: O=C(O)/C=C/c1ccc(/C(=C(\c2ccc(F)cc2Cl)C2CCC2)c2ccc3[nH]ncc3c2)cc1] |

TABLE 1-continued

| ERM Compound No. | Name | Structure |
|---|---|---|
| 1-6 | (E)-3-(4-((E)-2-(2-chloro-4-fluorophenyl)-2-cyclobutyl-1-(3-fluoro-1H-indazol-5-yl)vinyl)phenyl)acrylic acid | 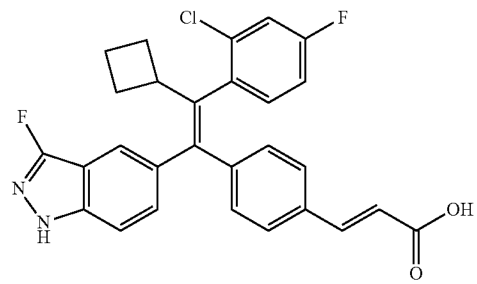 [SMILES: O=C(O)/C=C/c1ccc(/C(=C(\c2ccc(F)cc2Cl)C2CCC2)c2ccc3[nH]nc(F)c3c2)cc1] |
| 1-7 | (E)-3-(4-((E)-2-(4-chloro-2-cyanophenyl)-2-cyclobutyl-1-(3-fluoro-1H-indazol-5-yl)vinyl)phenyl)acrylic acid | 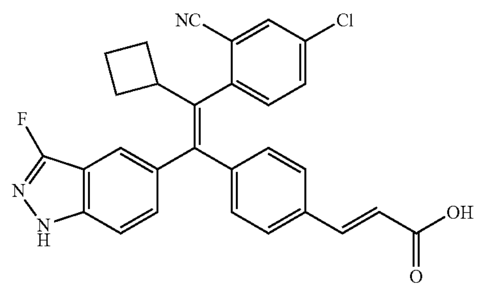 [SMILES: N#Cc1cc(Cl)ccc1/C(=C(\c1ccc(/C=C/C(=O)O)cc1)c1ccc2[nH]nc(F)c2c1)C1CCC1] |
| 1-8 | (E)-3-(4-((E)-2-(2-chloro-4-methoxyphenyl)-2-cyclobutyl-1-(3-fluoro-1H-indazol-5-yl)vinyl)phenyl)acrylic acid | 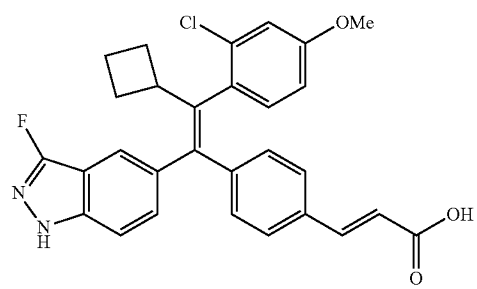 [SMILES: COc1ccc(/C(=C(\c2ccc(/C=C/C(=O)O)cc2)c2ccc3[nH]nc(F)c3c2)C2CCC2)c(Cl)c1] |
| 1-9 | (E)-3-(4-((E)-2-(3-chloro-5-(trifluoromethyl)pyridin-2-yl)-2-cyclobutyl-1-(3-fluoro-1H-indazol-5-yl)vinyl)phenyl)acrylic acid | 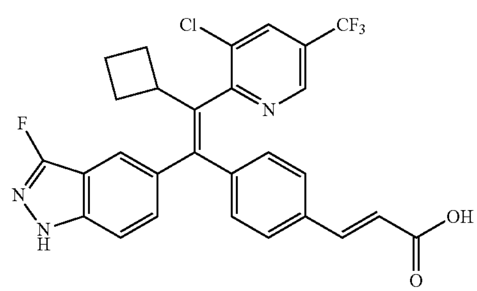 [SMILES: O=C(O)/C=C/c1ccc(/C(=C(\c2ncc(C(F)(F)F)cc2Cl)C2CCC2)c2ccc3[nH]nc(F)c3c2)cc1] |
| 1-10 | (E)-3-(4-((E)-2-(2-cyano-4-(trifluoromethyl)phenyl)-2-cyclobutyl-1-(3-fluoro-1H-indazol-5-yl)vinyl)phenyl)acrylic acid | 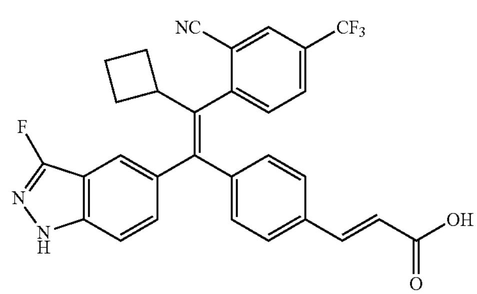 [SMILES: N#Cc1cc(C(F)(F)F)ccc1/C(=C(\c1ccc(/C=C/C(=O)O)cc1)c1ccc2[nH]nc(F)c2c1)C1CCC1] |

TABLE 1-continued

| ERM Compound No. | Name | Structure |
|---|---|---|
| 1-11 | (E)-3-(4-((E)-2-(2-chloro-4-cyanophenyl)-2-cyclobutyl-1-(3-fluoro-1H-indazol-5-yl)vinyl)phenyl)acrylic acid | 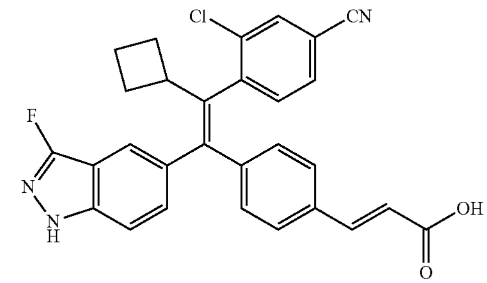 [SMILES: N#Cc1ccc(/C(=C(\c2ccc(/C=C/C(=O)O)cc2)c2ccc3[nH]nc(F)c3c2)C2CCC2)c(Cl)c1] |
| 1-12 | 3-((E)-4-((E)-2-(2-chloro-4-methoxyphenyl)-2-cyclobutyl-1-(3-fluoro-1H-indazol-5-yl)vinyl)styryl)-1,2,4-oxadiazol-5(4H)-one | 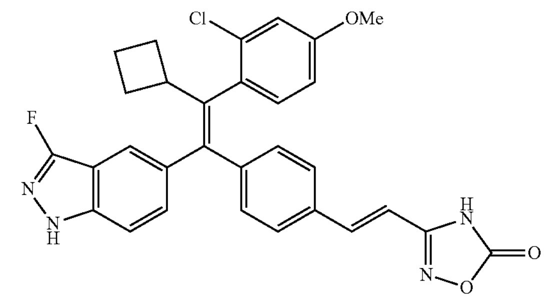 [SMILES: COc1ccc(/C(=C(\c2ccc(/C=C/c3noc(=O)[nH]3)cc2)c2ccc3[nH]nc(F)c3c2)C2CCC2)c(Cl)c1] |

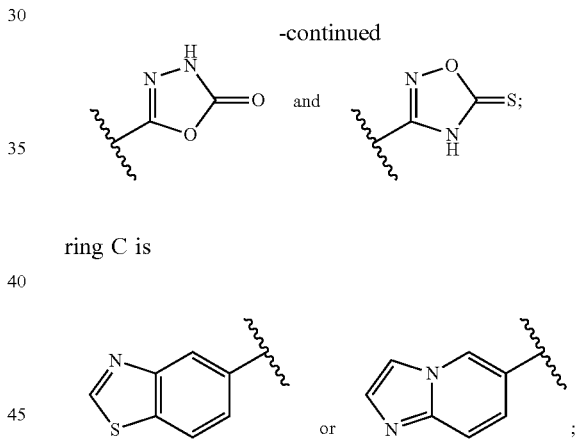

In another aspect, the estrogen receptor modulator compound for use in the methods and compositions described herein is a compound of Formula (B) or a pharmaceutically acceptable salt, or solvate thereof:

Formula (B)

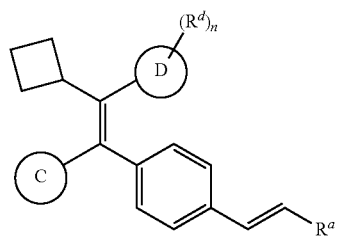

wherein, $R^a$ is —CO$_2$H or a 5-membered heterocycle selected from the group consisting of

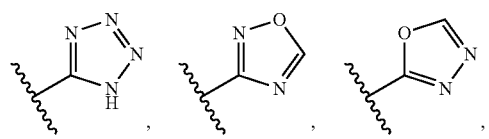

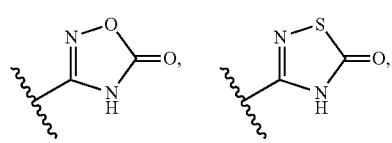

and ring C is ring D is phenyl or thienyl;

each $R^d$ is independently selected from H, halogen, —CN, —OR$^e$, —NHR$^e$, —NR$^e$R$^f$, —SR$^e$, —S(=O)R$^f$, —S(=O)$_2$R$^f$, C$_1$-C$_6$alkyl, and C$_1$-C$_6$fluoroalkyl;

each $R^e$ is independently selected from H, —C(=O)R$^f$, —C(=O)OR$^f$, —C(=O)NHR$^f$, C$_1$-C$_6$ alkyl, C$_1$-C$_6$ fluoroalkyl, C$_3$-C$_6$ cycloalkyl, substituted or unsubstituted monocyclic C$_2$-C$_6$heterocycloalkyl, substituted or unsubstituted phenyl, and substituted or unsubstituted monocyclic heteroaryl;

each $R^f$ is independently selected from C$_1$-C$_6$ alkyl, C$_1$-C$_6$ fluoroalkyl, C$_3$-C$_6$ cycloalkyl, substituted or unsubstituted monocyclic C$_2$-C$_6$ heterocycloalkyl, substituted or unsubstituted phenyl, and substituted or unsubstituted monocyclic heteroaryl;

n is 0, 1, or 2.

In some embodiments, ring C is

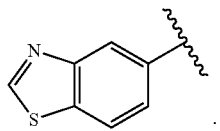 [SMILES: *c1ccc2scnc2c1]

In some embodiments, ring C is

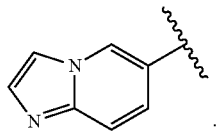 [SMILES: *c1ccc2nccn2c1]

In some embodiments,

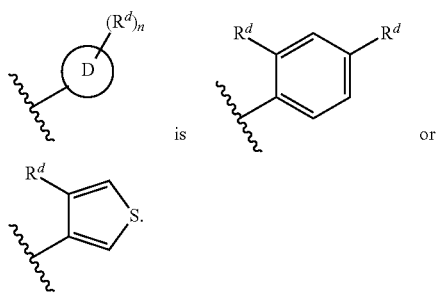

In some embodiments,

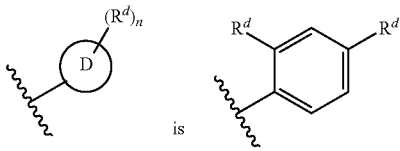

is

In some embodiments,

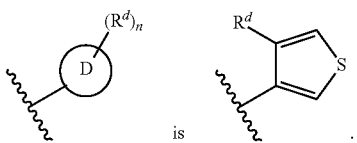

is .

In some embodiments, $R^a$ is —CO$_2$H.
In some embodiments, n is 1 or 2.
In some embodiments, n is 1.
In some embodiments, n is 2. In some embodiments, n is 0.

In some embodiments, each $R^d$ is independently selected from H, F, Cl, —CN, —OH, —OCH$_3$, —OCH$_2$CH$_3$, —S(=O)$_2$CH$_3$, —CH$_3$, —CH$_2$H$_3$, and —CF$_3$.

In some embodiments, each $R^d$ is independently selected from H, F, Cl, —CN, —OH, —OCH$_3$, —OCH$_2$CH$_3$, —CH$_3$, —CH$_2$H$_3$, and —CF$_3$.

In some embodiments, the estrogen receptor modulator compound of Formula (B) is a compound described in Table 2, or a pharmaceutically acceptable salt, or solvate thereof:

TABLE 2

| ERM Compound No. | Name | Structure |
|---|---|---|
| 2-1 | (E)-3-(4-((E)-1-(benzo[d]thiazol-5-yl)-2-(2-chloro-4-methoxyphenyl)-2-cyclobutylvinyl)phenyl)acrylic acid | 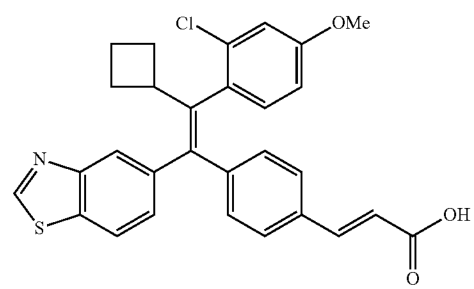 [SMILES: COc1ccc(/C(=C(\c2ccc(/C=C/C(=O)O)cc2)c2ccc3scnc3c2)C2CCC2)c(Cl)c1] |
| 2-2 | (E)-3-(4-((E)-1-(benzo[d]thiazol-5-yl)-2-cyclobutyl-2-(4-methylthiophen-3-yl)vinyl)phenyl)acrylic acid | 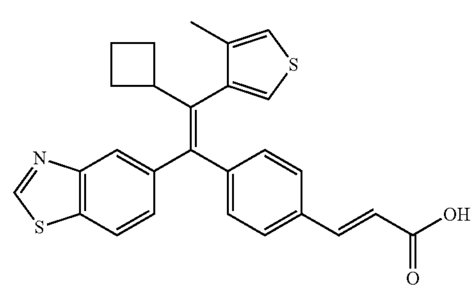 [SMILES: Cc1cscc1/C(=C(\c1ccc(/C=C/C(=O)O)cc1)c1ccc2scnc2c1)C1CCC1] |

TABLE 2-continued

| ERM Compound No. | Name | Structure |
|---|---|---|
| 2-3 | (E)-3-(4-((E)-1-(benzo[d]thiazol-5-yl)-2-(2-cyano-4-methoxyphenyl)-2-cyclobutylvinyl)phenyl)acrylic acid | 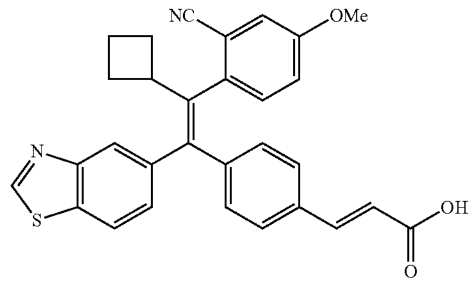 |
| 2-4 | (E)-3-(4-((E)-1-(benzo[d]thiazol-5-yl)-2-(2-cyano-4-(trifluoromethyl)phenyl)-2-cyclobutylvinyl)phenyl)acrylic acid | 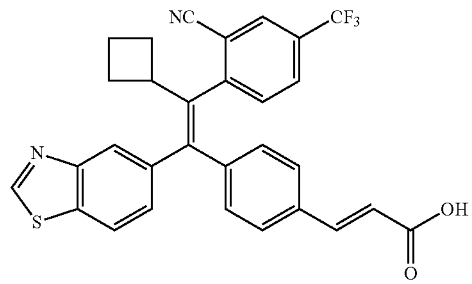 [SMILES: N#Cc1cc(C(F)(F)F)ccc1/C(=C(\c1ccc(/C=C/C(=O)O)cc1)c1ccc2scnc2c1)C1CCC1] |
| 2-5 | (E)-3-(4-((E)-2-(2-chloro-4-methoxyphenyl)-2-cyclobutyl-1-(imidazo[1,2-a]pyridin-6-yl)vinyl)phenyl)acrylic acid | 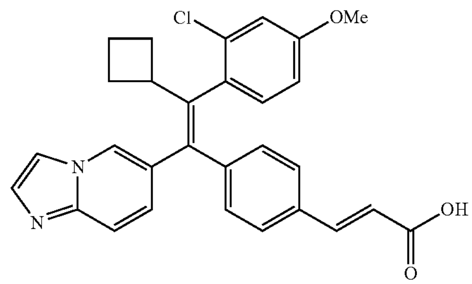 [SMILES: COc1ccc(/C(=C(\c2ccc(/C=C/C(=O)O)cc2)c2ccc3nccn3c2)C2CCC2)c(Cl)c1] |

In yet another aspect, the estrogen receptor modulator compound for use in the methods and compositions described herein is a compound of Formula (C) or a pharmaceutically acceptable salt, or solvate thereof:

Formula (C)

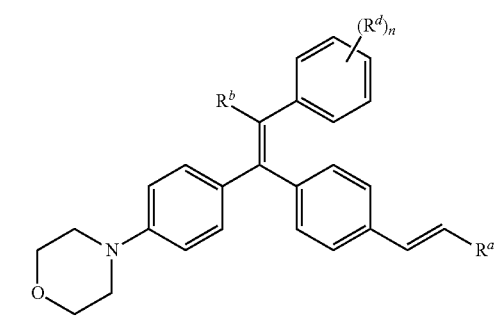

wherein, $R^a$ is —CO$_2$H or a 5-membered heterocycle selected from the group consisting of

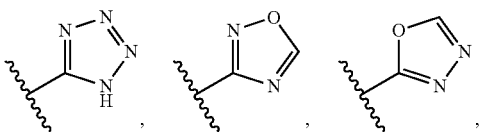

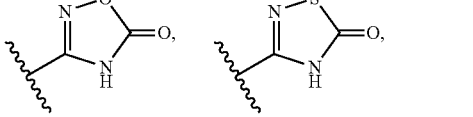

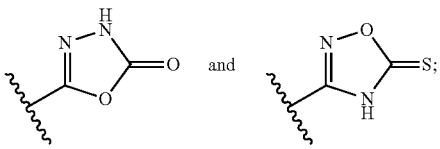

$R^b$ is $C_1$-$C_6$ alkyl or $C_3$-$C_6$ cycloalkyl;

each $R^d$ is independently selected from H, halogen, —CN, —OR$^e$, —NHR$^e$, —NR$^e$R$^f$, —SR$^e$, —S(=O)R$^f$, —S(=O)$_2$R$^f$, $C_1$-$C_6$alkyl, and $C_1$-$C_6$fluoroalkyl;

each $R^e$ is independently selected from H, —C(=O)R$^f$, —C(=O)OR$^f$, —C(=O)NHR$^f$, $C_1$-$C_6$ alkyl, $C_1$-$C_6$ fluoroalkyl, $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;

each $R^f$ is independently selected from $C_1$-$C_6$alkyl, $C_1$-$C_6$ fluoroalkyl, $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;

n is 0, 1, or 2.

In some embodiments, $R^a$ is —$CO_2H$.

In some embodiments, $R^b$ is —$CH_3$, —$CH_2CH_3$, cyclopropyl, or cyclobutyl.

In some embodiments, $R^b$ is —$CH_2CH_3$.

In some embodiments, $R^b$ is cyclobutyl.

In some embodiments, n is 1 or 2. In some embodiments, n is 1. In some embodiments, n is 2. In some embodiments, n is 0.

In some embodiments, each $R^d$ is independently selected from H, F, Cl, —CN, —OH, —$OCH_3$, —$OCH_2CH_3$, —$S(=O)_2CH_3$, —$CH_3$, —$CH_2H_3$, and —$CF_3$.

In some embodiments, each $R^d$ is independently selected from H, F, Cl, —CN, —OH, —$OCH_3$, —$OCH_2CH_3$, —$CH_3$, —$CH_2H_3$, and —$CF_3$.

In some embodiments, the estrogen receptor modulator compound of Formula (C) has the structure of Formula (C-1), or a pharmaceutically acceptable salt, or solvate thereof:

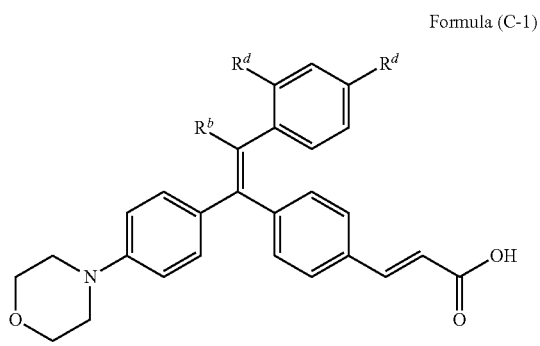

Formula (C-1)

In some embodiments, the estrogen receptor modulator compound of Formula (C) is a compound described in Table 3, or a pharmaceutically acceptable salt, or solvate thereof:

TABLE 3

| ERM Compound No. | Name | Structure |
|---|---|---|
| 3-1 | (E)-3-(4-((E)-2-(2-Chloro-4-fluorophenyl)-2-cyclobutyl-1-(4-morpholinophenyl)vinyl)phenyl) acrylic acid | 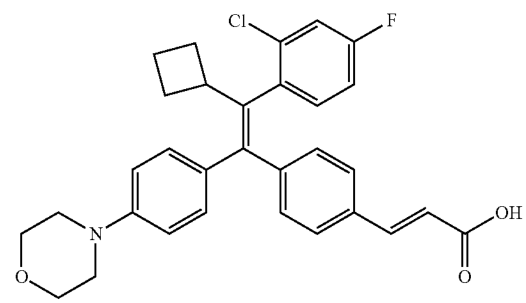 [SMILES: O=C(O)/C=C/c1ccc(/C(=C(\c2ccc(F)cc2Cl)C2CCC2)c2ccc(N3CCOCC3)cc2)cc1] |
| 3-2 | (E)-3-(4-((E)-2-(2-chloro-4-methoxyphenyl)-2-cyclobutyl-1-(4-morpholinophenyl)vinyl)phenyl) acrylic acid | 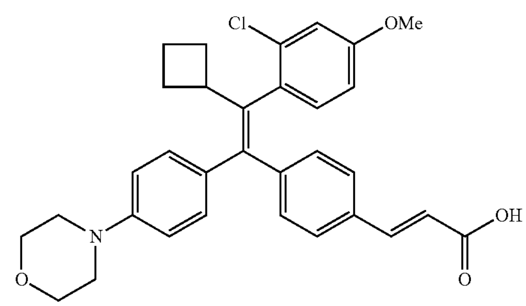 [SMILES: COc1ccc(/C(=C(\c2ccc(/C=C/C(=O)O)cc2)c2ccc(N3CCOCC3)cc2)C2CCC2)c(Cl)c1] |
| 3-3 | (E)-3-(4-((E)-2-(2-Chloro-4-(trifluoromethyl)phenyl)-2-cyclobutyl-1-(4-morpholinophenyl)vinyl)phenyl) acrylic acid | 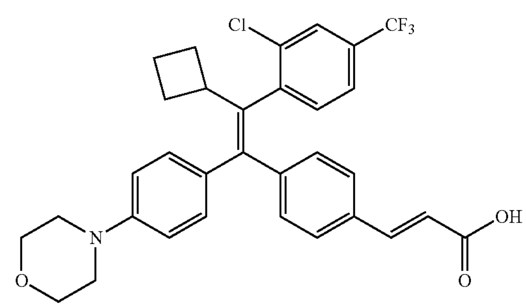 |

TABLE 3-continued

| ERM Compound No. | Name | Structure |
|---|---|---|
| 3-4 | (E)-3-(4-((E)-2-(2-Chloro-4-cyanophenyl)-2-cyclobutyl-1-(4-morpholinophenyl)vinyl)phenyl)acrylic acid | 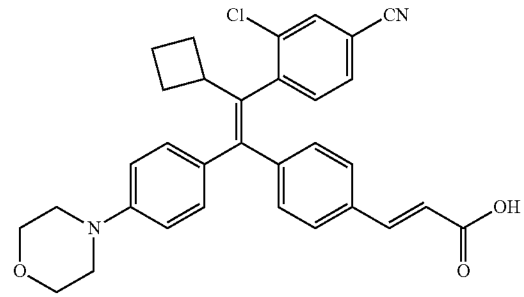 [SMILES: N#Cc1ccc(/C(=C(\c2ccc(/C=C/C(=O)O)cc2)c2ccc(N3CCOCC3)cc2)C2CCC2)c(Cl)c1] |

In another aspect, the estrogen receptor modulator compound for use in the methods and compositions described herein is a compound of Formula (D) or a pharmaceutically acceptable salt, or solvate thereof:

Formula (D)

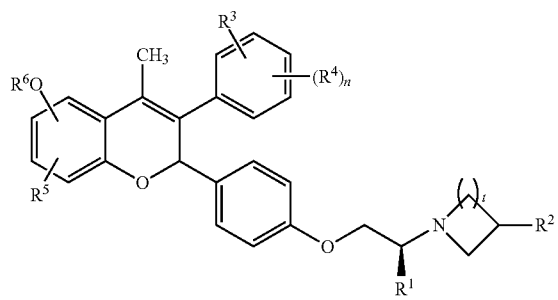

wherein,
$R^1$ is H, $C_1$-$C_4$ alkyl, or $C_1$-$C_4$ fluoroalkyl;
$R^2$ is H, F, $C_1$-$C_4$ alkyl or $C_1$-$C_4$ fluoroalkyl;
$R^3$ is H, halogen, —CN, —$OR^6$, —$NHR^6$, —$NR^6R^7$, —$SR^6$, —S(=O)$R^7$, —S(=O)$_2R^7$, $C_1$-$C_4$alkyl, or $C_1$-$C_4$fluoroalkyl;
each $R^4$ is independently selected from H, halogen, —CN, —OH, $C_1$-$C_6$alkyl, $C_1$-$C_4$ fluoroalkyl, $C_1$-$C_4$fluoroalkoxy, and $C_1$-$C_4$alkoxy;
each $R^5$ is H, F, Cl, —OH, —$CH_3$, —$CF_3$, or —$OCH_3$;
each $R^6$ is independently selected from H, —C(=O)$R^7$, —C(=O)$OR^7$, —C(=O)$NHR^7$, $C_1$-$C_6$ alkyl, $C_1$-$C_6$ fluoroalkyl, $C_3$-$C_6$ cycloalkyl, substituted or unsubstituted $C_2$-$C_6$ heterocycloalkyl, substituted or unsubstituted phenyl, and substituted or unsubstituted monocyclic heteroaryl;
each $R^7$ is independently selected from $C_1$-$C_6$ alkyl, $C_1$-$C_6$ fluoroalkyl, substituted or unsubstituted $C_3$-$C_6$ cycloalkyl, substituted or unsubstituted monocyclic $C_2$-$C_6$ heterocycloalkyl, substituted or unsubstituted phenyl, and substituted or unsubstituted monocyclic heteroaryl;
n is 0, 1, or 2; and
t is 1 or 2.
In some embodiments, $R^1$ is H, —$CH_3$, —$CH_2F$, —$CHF_2$, or —$CF_3$.
In some embodiments, each $R^2$ is independently F, —$CH_3$, —$CH_2CH_3$, —$CH_2F$, —$CHF_2$, —$CF_3$, —$CHFCH_3$, —$CH_2CH_2F$, —$CH_2CHF_2$, —$CH_2CF_3$, —$CH_2CH_2CF_3$, —$CH_2CH_2CH_2CF_3$, —$CHCH_3CF_3$, —$CH(CF_3)_2$, or —CF ($CH_3)_2$. In some embodiments, each $R^2$ is independently F, —$CH_3$, —$CH_2F$, —$CHF_2$, or —$CF_3$. In some embodiments, each $R^2$ is independently —$CH_3$, —$CH_2F$, —$CHF_2$, or —$CF_3$. In some embodiments, each $R^2$ is independently —$CH_2F$. In some embodiments, each $R^2$ is independently —$CH_3$.
In some embodiments, t is 1. In some embodiments, t is 2.
In some embodiments, $R^3$ is —$OR^6$. In some embodiments, $R^3$ is —OH.
In some embodiments, each $R^4$ is independently selected from H, F, Cl, —OH, —$CH_3$, —$CF_3$, or —$OCH_3$.
In some embodiments, each $R^5$ is independently selected from H and F.
In some embodiments, each $R^6$ is independently selected from H, —C(=O)$R^7$, —C(=O)$OR^7$, —C(=O)$NHR^7$, $C_1$-$C_6$ alkyl, $C_1$-$C_6$ fluoroalkyl, and substituted or unsubstituted phenyl. In some embodiments, each $R^6$ is H.
In some embodiments, each $R^7$ is independently selected from $C_1$-$C_6$ alkyl, $C_1$-$C_6$ fluoroalkyl, and substituted or unsubstituted phenyl.
In some embodiments,

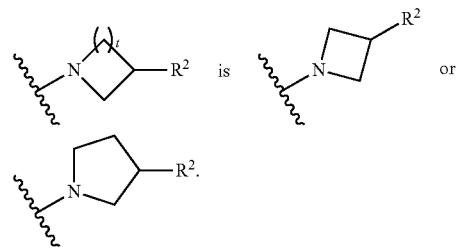

In some embodiments,

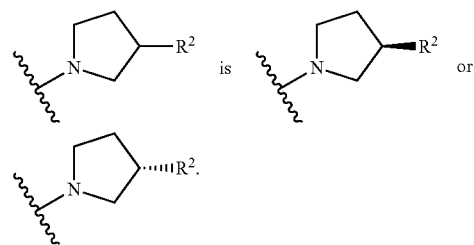

In some embodiments,
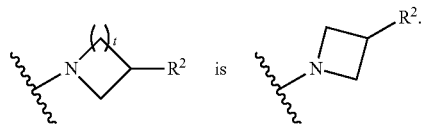 is
In some embodiments,
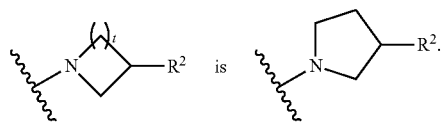 is
In some embodiments,
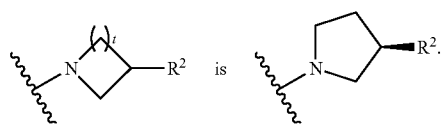 is
In some embodiments,
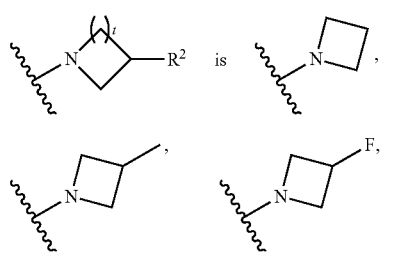 is
In some embodiments,
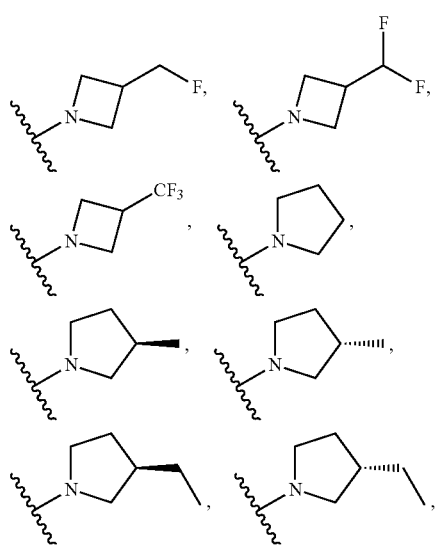
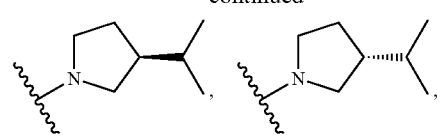,
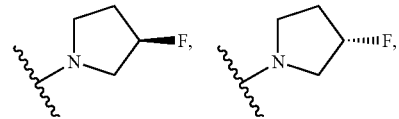,
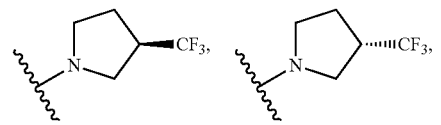,
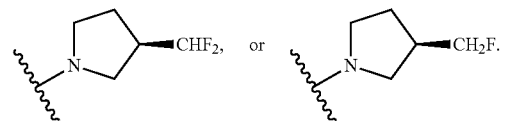.
In some embodiments,
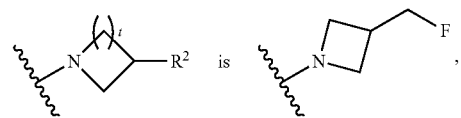 is
In some embodiments,
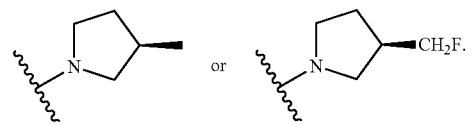 is
In some embodiments,
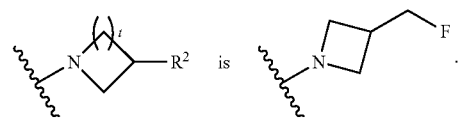 is
In some embodiments,
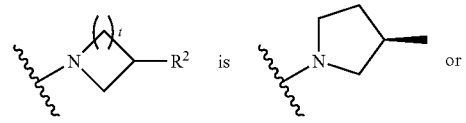 is
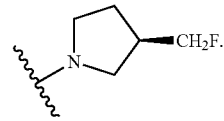

In some embodiments,

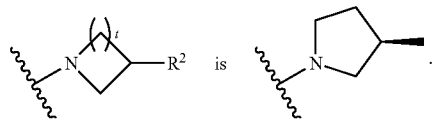

In some embodiments,

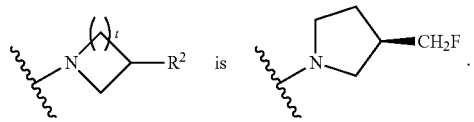

In some embodiments, the estrogen receptor modulator compound of Formula (D) has the following structure of Formula (D-1), or a pharmaceutically acceptable salt, or solvate thereof:

Formula (D-1)

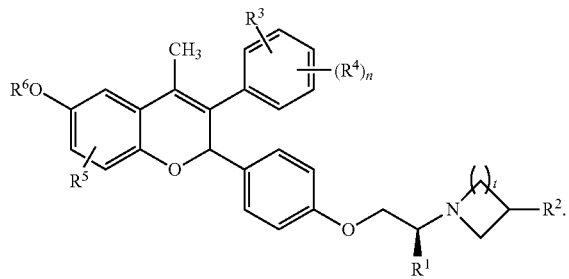

In some embodiments, the estrogen receptor modulator compound of Formula (D) has the following structure of Formula (D-2), or a pharmaceutically acceptable salt, or solvate thereof:

Formula (D-2)

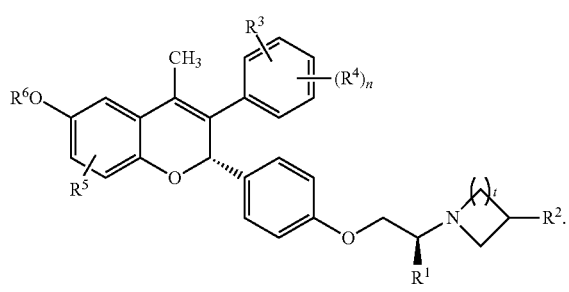

In some embodiments, the estrogen receptor modulator compound of Formula (D) has the following structure of Formula (D-3), or a pharmaceutically acceptable salt, or solvate thereof:

Formula (D-3)

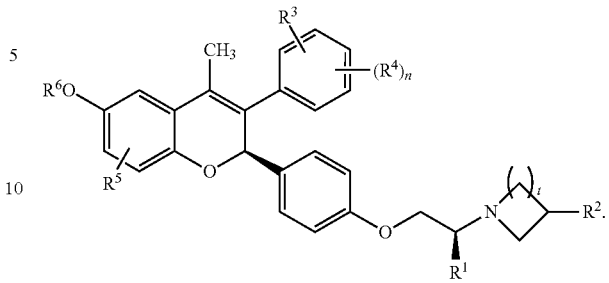

In some embodiments, the estrogen receptor modulator compound of Formula (D) has the following structure of Formula (D-4), or a pharmaceutically acceptable salt, or solvate thereof:

Formula (D-4)

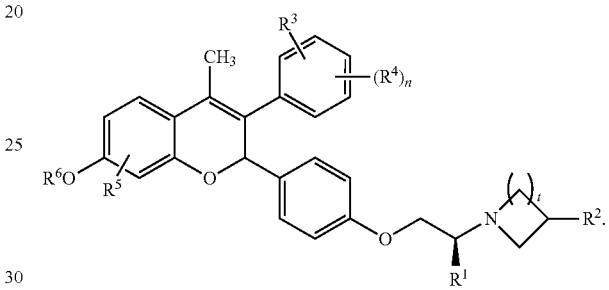

In some embodiments, the estrogen receptor modulator compound of Formula (D) has the following structure of Formula (D-5), or a pharmaceutically acceptable salt, or solvate thereof:

Formula (D-5)

In some embodiments, the estrogen receptor modulator compound of Formula (D) has the following structure of Formula (D-6), or a pharmaceutically acceptable salt, or solvate thereof:

Formula (D-6)

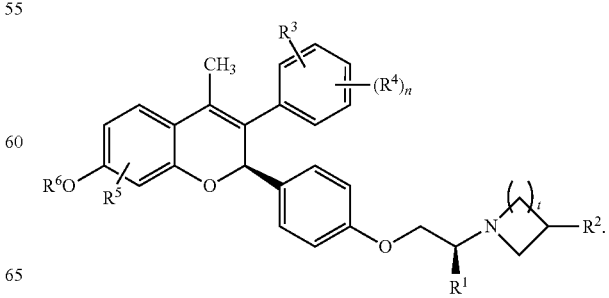

In some embodiments,

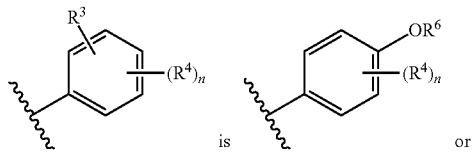

is or

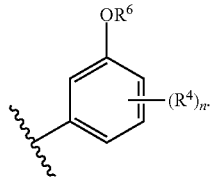

In some embodiments, the estrogen receptor modulator compound of Formula (D) is a compound described in Table 4, or a pharmaceutically acceptable salt, or solvate thereof:

TABLE 4

| ERM Compound No. | Name | Structure |
|---|---|---|
| 4-1 | 3-(3-hydroxyphenyl)-4-methyl-2-(4-(2-((R)-3-methylpyrrolidin-1-yl)ethoxy)phenyl)-2H-chromen-6-ol | 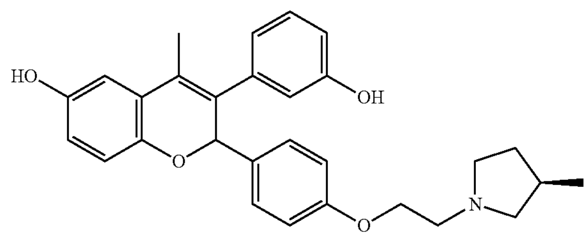 [SMILES: CC1=C(c2cccc(O)c2)C(c2ccc(OCCN3CC[C@@H](C)C3)cc2)Oc2ccc(O)cc21] |
| 4-2 | (S)-3-(3-hydroxyphenyl)-4-methyl-2-(4-(2-((R)-3-methylpyrrolidin-1-yl)ethoxy)phenyl)-2H-chromen-6-ol | 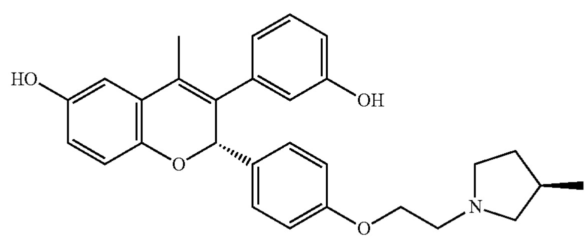 [SMILES: CC1=C(c2cccc(O)c2)[C@H](c2ccc(OCCN3CC[C@@H](C)C3)cc2)Oc2ccc(O)cc21] |
| 4-3 | (R)-3-(3-hydroxyphenyl)-4-methyl-2-(4-(2-((R)-3-methylpyrrolidin-1-yl)ethoxy)phenyl)-2H-chromen-6-ol | 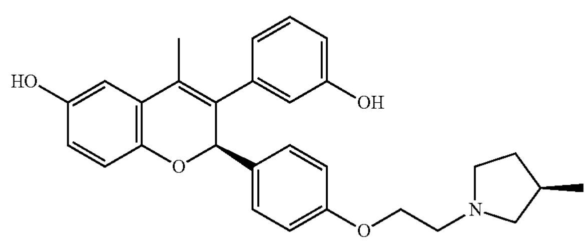 [SMILES: CC1=C(c2cccc(O)c2)[C@@H](c2ccc(OCCN3CC[C@@H](C)C3)cc2)Oc2ccc(O)cc21] |
| 4-4 | 3-(3-hydroxyphenyl)-4-methyl-2-(4-((S)-2-(pyrrolidin-1-yl)propoxy)phenyl)-2H-chromen-6-ol | 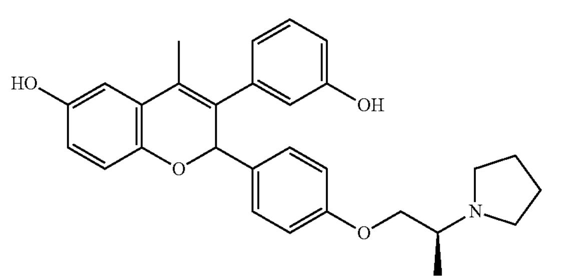 [SMILES: CC1=C(c2cccc(O)c2)C(c2ccc(OC[C@H](C)N3CCCC3)cc2)Oc2ccc(O)cc21] |

TABLE 4-continued

| ERM Compound No. | Name | Structure |
|---|---|---|
| 4-5 | (S)-3-(3-hydroxyphenyl)-4-methyl-2-(4-((S)-2-(pyrrolidin-1-yl)propoxy)phenyl)-2H-chromen-6-ol | 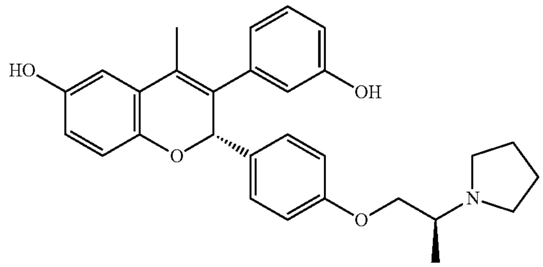 [SMILES: CC1=C(c2cccc(O)c2)[C@H](c2ccc(OC[C@H](C)N3CCCC3)cc2)Oc2ccc(O)cc21] |
| 4-6 | (R)-3-(3-hydroxyphenyl)-4-methyl-2-(4-((S)-2-(pyrrolidin-1-yl)propoxy)phenyl)-2H-chromen-6-ol | 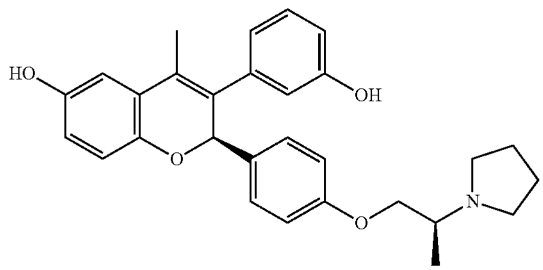 [SMILES: CC1=C(c2cccc(O)c2)[C@@H](c2ccc(OC[C@H](C)N3CCCC3)cc2)Oc2ccc(O)cc21] |
| 4-7 | 3-(3-hydroxyphenyl)-4-methyl-2-(4-((S)-2-((R)-3-methylpyrrolidin-1-yl)propoxy)phenyl)-2H-chromen-7-ol | 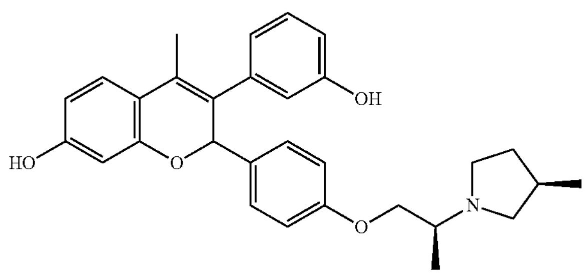 [SMILES: CC1=C(c2cccc(O)c2)C(c2ccc(OC[C@H](C)N3CC[C@@H](C)C3)cc2)Oc2cc(O)ccc21] |
| 4-8 | (S)-3-(3-hydroxyphenyl)-4-methyl-2-(4-((S)-2-((R)-3-methylpyrrolidin-1-yl)propoxy)phenyl)-2H-chromen-7-ol | 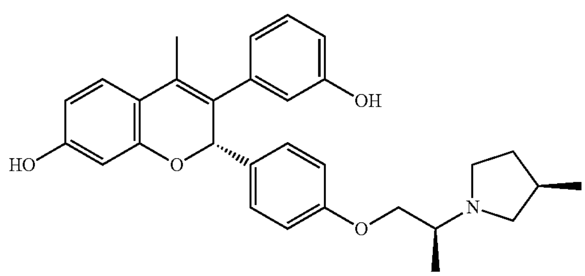 [SMILES: CC1=C(c2cccc(O)c2)[C@H](c2ccc(OC[C@H](C)N3CC[C@@H](C)C3)cc2)Oc2cc(O)ccc21] |
| 4-9 | (R)-3-(3-hydroxyphenyl)-4-methyl-2-(4-((S)-2-((R)-3-methylpyrrolidin-1-yl)propoxy)phenyl)-2H-chromen-7-ol | 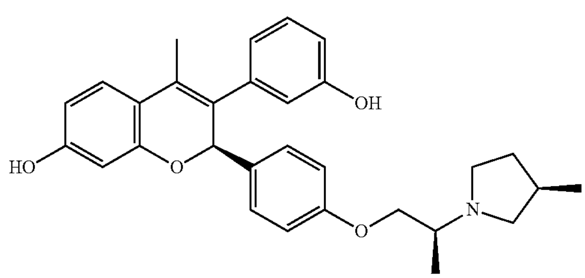 [SMILES: CC1=C(c2cccc(O)c2)[C@@H](c2ccc(OC[C@H](C)N3CC[C@@H](C)C3)cc2)Oc2cc(O)ccc21] |

TABLE 4-continued

| ERM Compound No. | Name | Structure |
|---|---|---|
| 4-10 | 3-(4-hydroxyphenyl)-4-methyl-2-(4-((S)-2-((R)-3-methylpyrrolidin-1-yl)propoxy)phenyl)-2H-chromen-6-ol | 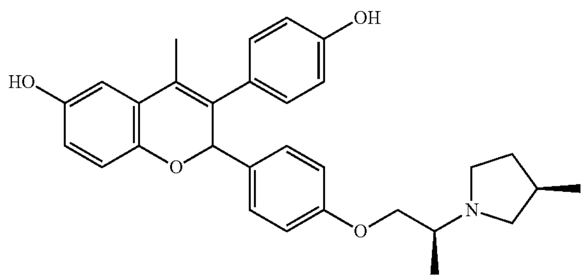 [SMILES: CC1=C(c2ccc(O)cc2)C(c2ccc(OC[C@H](C)N3CC[C@@H](C)C3)cc2)Oc2ccc(O)cc21] |
| 4-11 | (S)-3-(4-hydroxyphenyl)-4-methyl-2-(4-((S)-2-((R)-3-methylpyrrolidin-1-yl)propoxy)phenyl)-2H-chromen-6-ol | 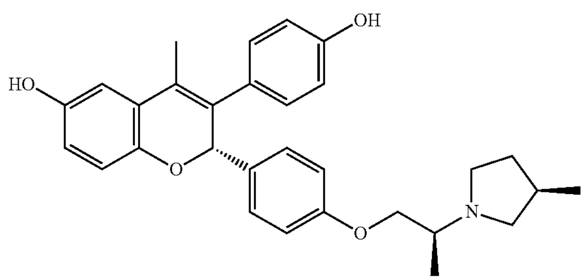 [SMILES: CC1=C(c2ccc(O)cc2)[C@H](c2ccc(OC[C@H](C)N3CC[C@@H](C)C3)cc2)Oc2ccc(O)cc21] |
| 4-12 | (R)-3-(4-hydroxyphenyl)-4-methyl-2-(4-((S)-2-((R)-3-methylpyrrolidin-1-yl)propoxy)phenyl)-2H-chromen-6-ol | 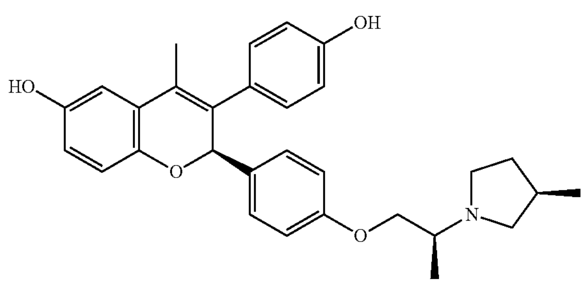 [SMILES: CC1=C(c2ccc(O)cc2)[C@@H](c2ccc(OC[C@H](C)N3CC[C@@H](C)C3)cc2)Oc2ccc(O)cc21] |
| 4-13 | 3-(3-hydroxyphenyl)-4-methyl-2-(4-((S)-2-((R)-3-methylpyrrolidin-1-yl)propoxy)phenyl)-2H-chromen-6-ol | 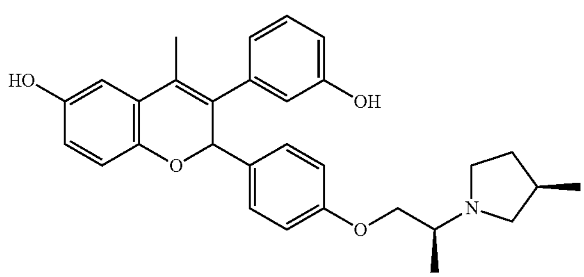 [SMILES: CC1=C(c2cccc(O)c2)[C@H](c2ccc(OC[C@H](C)N3CC[C@@H](C)C3)cc2)Oc2ccc(O)cc21] |
| 4-14 | (S)-3-(3-hydroxyphenyl)-4-methyl-2-(4-((S)-2-((R)-3-methylpyrrolidin-1-yl)propoxy)phenyl)-2H-chromen-6-ol | 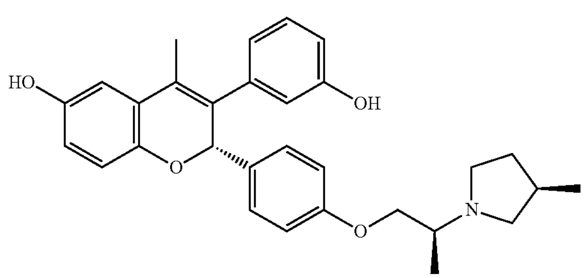 |

TABLE 4-continued

| ERM Compound No. | Name | Structure |
|---|---|---|
| 4-15 | (R)-3-(3-hydroxyphenyl)-4-methyl-2-(4-((S)-2-((R)-3-methylpyrrolidin-1-yl)propoxy)phenyl)-2H-chromen-6-ol | 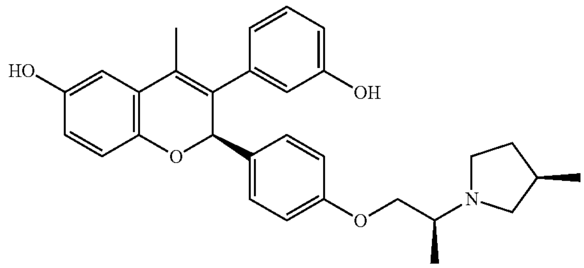 [SMILES: CC1=C(c2cccc(O)c2)[C@@H](c2ccc(OC[C@H](C)N3CC[C@@H](C)C3)cc2)Oc2ccc(O)cc21] |
| 4-16 | 2-(4-((S)-2-((R)-3-(fluoromethyl)pyrrolidin-1-yl)propoxy)phenyl)-3-(3-hydroxyphenyl)-4-methyl-2H-chromen-6-ol | 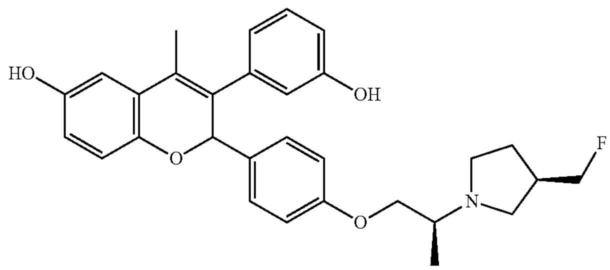 [SMILES: CC1=C(c2cccc(O)c2)C(c2ccc(OC[C@H](C)N3CC[C@@H](CF)C3)cc2)Oc2ccc(O)cc21] |
| 4-17 | (S)-2-(4-((S)-2(R)-3-(fluoromethyl)pyrrolidin-1-yl)propoxy)phenyl)-3-(3-hydroxyphenyl)-4-methyl-2H-chromen-6-ol | 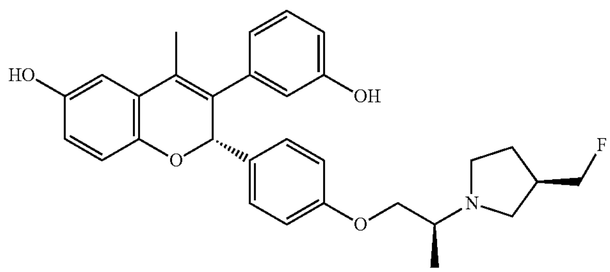 |
| 4-18 | (R)-2-(4-((S)-2-((R)-3-(fluoromethyl)pyrrolidin-1-yl)propoxy)phenyl)-3-(3-hydroxyphenyl)-4-methyl-2H-chromen-6-ol | 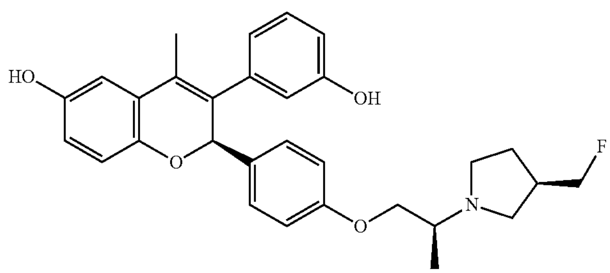 [SMILES: CC1=C(c2cccc(O)c2)[C@@H](c2ccc(OC[C@H](C)N3CC[C@@H](CF)C3)cc2)Oc2ccc(O)cc21] |
| 4-19 | 2-(4-(2-((R)-3-(fluoromethyl)pyrrolidin-1-yl)ethoxy)phenyl)-3-(3-hydroxyphenyl)-4-methyl-2H-chromen-6-ol | 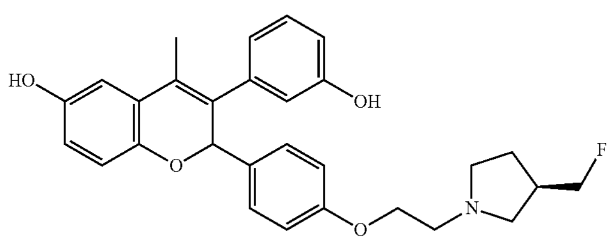 [SMILES: CC1=C(c2cccc(O)c2)C(c2ccc(OCCN3CC[C@@H](CF)C3)cc2)Oc2ccc(O)cc21] |
| 4-20 | (S)-2-(4-(2-((R)-3-(fluoromethyl)pyrrolidin-1-yl)ethoxy)phenyl)-3-(3-hydroxyphenyl)-4-methyl-2H-chromen-6-ol | 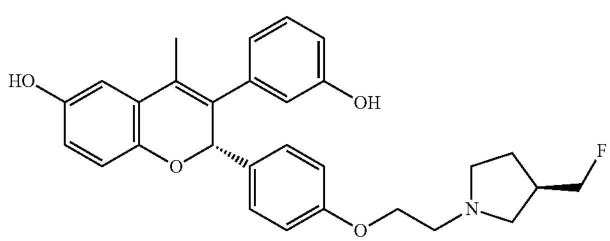 [SMILES: CC1=C(c2cccc(O)c2)[C@H](c2ccc(OCCN3CC[C@@H](CF)C3)cc2)Oc2ccc(O)cc21] |

TABLE 4-continued

| ERM Compound No. | Name |
|---|---|
| 4-21 | (R)-2-(4-(2-((R)-3-(fluoromethyl)pyrrolidin-1-yl)ethoxy)phenyl)-3-(3-hydroxyphenyl)-4-methyl-2H-chromen-6-ol |
| 4-22 | 2-(4-(2-(3-(fluoromethyl)azetidin-1-yl)ethoxy)phenyl)-3-(3-hydroxyphenyl)-4-methyl-2H-chromen-6-ol |
| 4-23 | (S)-2-(4-(2-(3-(fluoromethyl)azetidin-1-yl)ethoxy)phenyl)-3-(3-hydroxyphenyl)-4-methyl-2H-chromen-6-ol |
| 4-24 | (R)-2-(4-(2-(3-(fluoromethyl)azetidin-1-yl)ethoxy)phenyl)-3-(3-hydroxyphenyl)-4-methyl-2H-chromen-6-ol |
| 4-25 | 2-(4-(2-((R)-3-(fluoromethyl)pyrrolidin-1-yl)ethoxy)phenyl)-3-(4-fluorophenyl)-4-methyl-2H-chromen-6-ol |
| 4-26 | (S)-2-(4-(2-((R)-3-(fluoromethyl)pyrrolidin-1-yl)ethoxy)phenyl)-3-(4-fluorophenyl)-4-methyl-2H-chromen-6-ol |

TABLE 4-continued

| ERM Compound No. | Name | Structure |
|---|---|---|
| 4-27 | (R)-2-(4-(2-((R)-3-(fluoromethyl)pyrrolidin-1-yl)ethoxy)phenyl)-3-(4-fluorophenyl)-4-methyl-2H-chromen-6-ol | 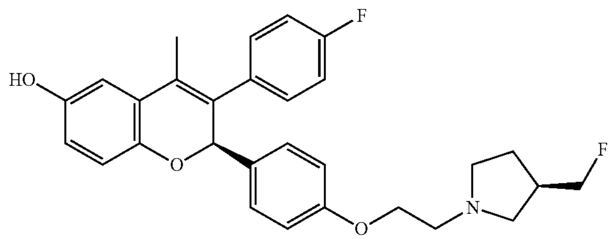 [SMILES: CC1=C(c2ccc(F)cc2)[C@@H](c2ccc(OCCN3CC[C@@H](CF)C3)cc2)Oc2ccc(O)cc21] |
| 4-28 | 2-(4-((S)-2-((R)-3-(fluoromethyl)pyrrolidin-1-yl)propoxy)phenyl)-3-(4-fluorophenyl)-4-methyl-2H-chromen-6-ol | 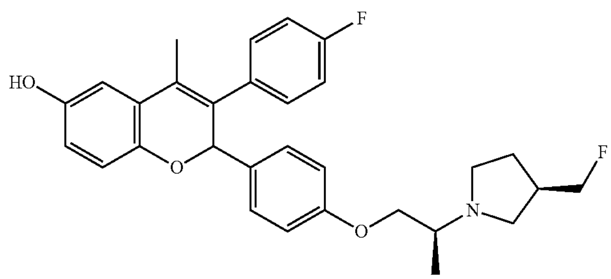 [SMILES: CC1=C(c2ccc(F)cc2)C(c2ccc(OC[C@H](C)N3CC[C@@H](CF)C3)cc2)Oc2ccc(O)cc21] |
| 4-29 | (S)-2-(4-((S)-2-((R)-3-(fluoromethyl)pyrrolidin-1-yl)propoxy)phenyl)-3-(4-fluorophenyl)-4-methyl-2H-chromen-6-ol | 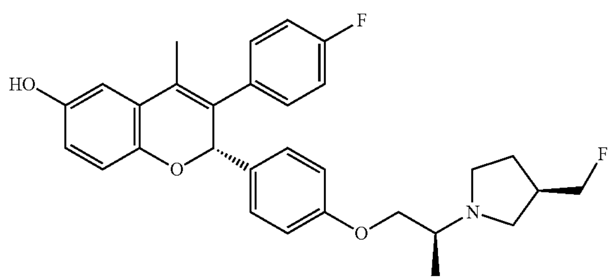 |
| 4-30 | (R)-2-(4-((S)-2-((R)-3-(fluoromethyl)pyrrolidin-1-yl)propoxy)phenyl)-3-(4-fluorophenyl)-4-methyl-2H-chromen-6-ol | 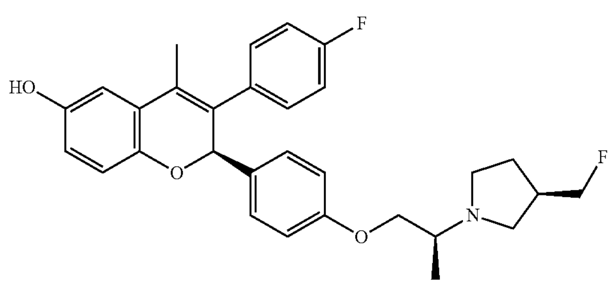 [SMILES: CC1=C(c2ccc(F)cc2)[C@@H](c2ccc(OC[C@H](C)N3CC[C@@H](CF)C3)cc2)Oc2ccc(O)cc21] |
| 4-31 | 2-(4-(2-(3-(difluoromethyl)azetidin-1-yl)ethoxy)phenyl)-3-(3-hydroxyphenyl)-4-methyl-2H-chromen-6-ol | 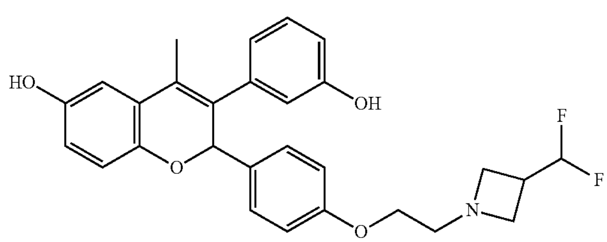 [SMILES: CC1=C(c2cccc(O)c2)C(c2ccc(OCCN3CC(C(F)F)C3)cc2)Oc2ccc(O)cc21] |
| 4-32 | (S)-2-(4-(2-(3-(difluoromethyl)azetidin-1-yl)ethoxy)phenyl)-3-(3-hydroxyphenyl)-4-methyl-2H-chromen-6-ol | 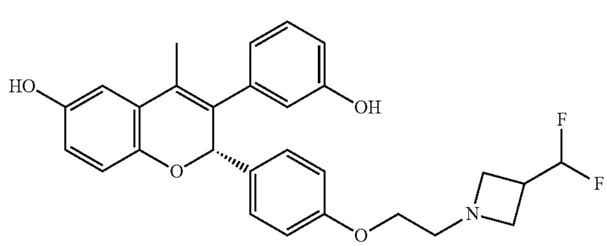 [SMILES: CC1=C(c2cccc(O)c2)[C@H](c2ccc(OCCN3CC(C(F)F)C3)cc2)Oc2ccc(O)cc21] |

TABLE 4-continued

| ERM Compound No. | Name |
|---|---|
| 4-33 | (R)-2-(4-(2-(3-(difluoromethyl)azetidin-1-yl)ethoxy)phenyl)-3-(3-hydroxyphenyl)-4-methyl-2H-chromen-6-ol |
| 4-34 | 2-(4-(2-((R)-3-(fluoromethyl)pyrrolidin-1-yl)ethoxy)phenyl)-4-methyl-3-phenyl-2H-chromen-6-ol |
| 4-35 | (S)-2-(4-(2-((R)-3-(fluoromethyl)pyrrolidin-1-yl)ethoxy)phenyl)-4-methyl-3-phenyl-2H-chromen-6-ol |
| 4-36 | (R)-2-(4-(2-((R)-3-(fluoromethyl)pyrrolidin-1-yl)ethoxy)phenyl)-4-methyl-3-phenyl-2H-chromen-6-ol |
| 4-37 | 3-(4-chlorophenyl)-2-(4-(2-(3-(fluoromethyl)azetidin-1-yl)ethoxy)phenyl)-4-methyl-2H-chromen-6-ol |
| 4-38 | (S)-3-(4-chlorophenyl)-2-(4-(2-(3-(fluoromethyl)azetidin-1-yl)ethoxy)phenyl)-4-methyl-2H-chromen-6-ol |

TABLE 4-continued

| ERM Compound No. | Name | Structure |
|---|---|---|
| 4-39 | (R)-3-(4-chlorophenyl)-2-(4-(2-(3-(fluoromethyl)azetidin-1-yl)ethoxy)phenyl)-4-methyl-2H-chromen-6-ol | 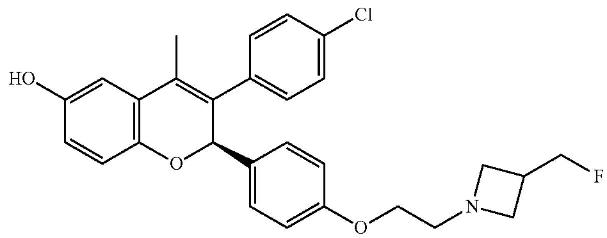 [SMILES: CC1=C(c2ccc(Cl)cc2)[C@@H](c2ccc(OCCN3CC(CF)C3)cc2)Oc2ccc(O)cc21] |
| 4-40 | 4-(2-(4-(2-(3-(fluoromethyl)azetidin-1-yl)ethoxy)phenyl)-6-hydroxy-4-methyl-2H-chromen-3-yl)benzonitrile | 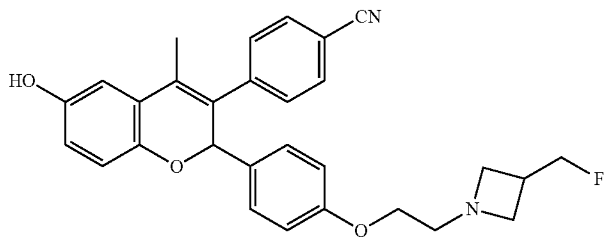 [SMILES: CC1=C(c2ccc(C#N)cc2)C(c2ccc(OCCN3CC(CF)C3)cc2)Oc2ccc(O)cc21] |
| 4-41 | (S)-4-(2-(4-(2-(3-(fluoromethyl)azetidin-1-yl)ethoxy)phenyl)-6-hydroxy-4-methyl-2H-chromen-3-yl)benzonitrile | 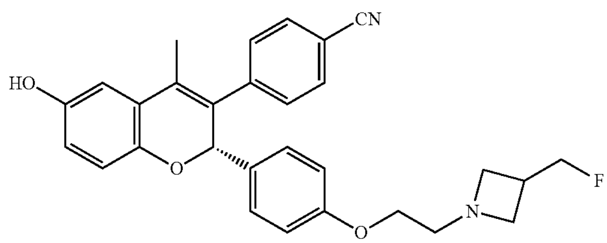 |
| 4-42 | (R)-4-(2-(4-(2-(3-(fluoromethyl)azetidin-1-yl)ethoxy)phenyl)-6-hydroxy-4-methyl-2H-chromen-3-yl)benzonitrile | 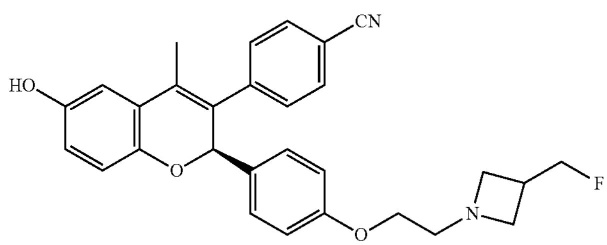 [SMILES: CC1=C(c2ccc(C#N)cc2)[C@@H](c2ccc(OCCN3CC(CF)C3)cc2)Oc2ccc(O)cc21] |
| 4-43 | 2-(4-(2-(3-(fluoromethyl)azetidin-1-yl)ethoxy)phenyl)-3-(4-fluorophenyl)-4-methyl-2H-chromen-6-ol | 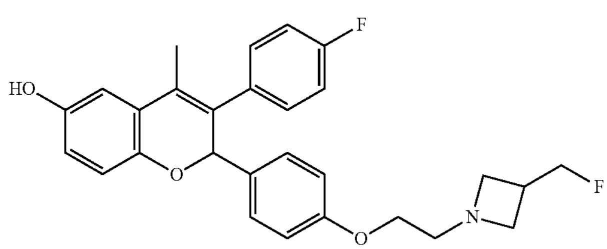 |
| 4-44 | (S)-2-(4-(2-(3-(fluoromethyl)azetidin-1-yl)ethoxy)phenyl)-3-(4-fluorophenyl)-4-methyl-2H-chromen-6-ol | 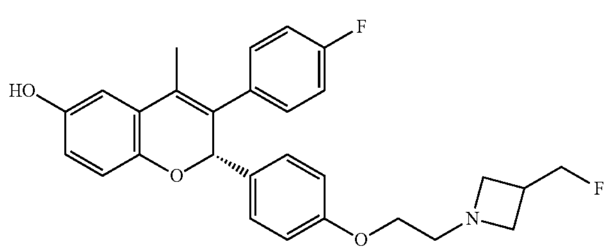 [SMILES: CC1=C(c2ccc(F)cc2)[C@H](c2ccc(OCCN3CC(CF)C3)cc2)Oc2ccc(O)cc21] |

TABLE 4-continued

| ERM Compound No. | Name | Structure |
|---|---|---|
| 4-45 | (R)-2-(4-(2-(3-(fluoromethyl)azetidin-1-yl)ethoxy)phenyl)-3-(4-fluorophenyl)-4-methyl-2H-chromen-6-ol | 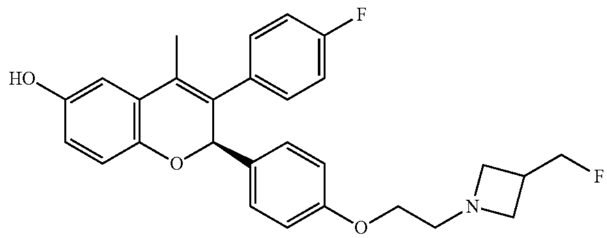 [SMILES: CC1=C(c2ccc(F)cc2)[C@@H](c2ccc(OCCN3CC(CF)C3)cc2)Oc2ccc(O)cc21] |

Further Forms of the Estrogen Receptor Modulator Compounds

In some embodiments, estrogen receptor modulator compounds described are used as pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

In some embodiments, estrogen receptor modulator compounds described herein may include one or more stereocenters. It is understood that where a stereocenter exists, such a stereocenter may be drawn out in the R configuration or the S configuration. Unless a specific configuration of a stereocenter is drawn out, then the compounds described herein are meant to include all such possible stereochemical configurations (i.e. racemic form, R configuration, S configuration).

In some embodiments, a compound of Formula (A), (B), (C) or (D), or a pharmaceutically acceptable salt, or N-oxide thereof, decreases the activity of a mutant ER. In some embodiments, a compound of Formula (A), (B), (C) or (D), or a pharmaceutically acceptable salt, or N-oxide thereof, decreases the activity of a wild-type ER. In some embodiments, a compound of Formula (A), (B), (C) or (D), or a pharmaceutically acceptable salt, or N-oxide thereof, decreases the activity of a mutant ER-α having one wild-type ER-α polypeptide and one mutant ER-α polypeptide (i.e., a heterodimer). In some embodiments, a compound of Formula (A), (B), (C) or (D), or a pharmaceutically acceptable salt, or N-oxide thereof, decreases the activity of a mutant ER-α having two mutant ER-α polypeptides (i.e., a homodimer). In some embodiments, a compound of Formula (A), (B), (C) or (D), or a pharmaceutically acceptable salt, or N-oxide thereof, decreases the activity of a mutant ER-α in a cell that expresses both a wild-type and mutant ER-α (i.e., heterogeneous expression). In some embodiments, a compound of Formula (A), (B), (C) or (D), or a pharmaceutically acceptable salt, or N-oxide thereof, decreases the activity of a wild-type ER-α in a cell that expresses both a wild-type and mutant ER. In some embodiments, a compound of Formula (A), (B), (C) or (D), or a pharmaceutically acceptable salt, or N-oxide thereof, decreases the activity of a mutant ER-α in a cell that expresses only mutant ER-α (i.e., homogeneous expression). In some embodiments, a compound of Formula (A), (B), (C) or (D), or a pharmaceutically acceptable salt, or N-oxide thereof, decreases the activity of an ER having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, a compound of Formula (A), (B), (C) or (D), or a pharmaceutically acceptable salt, or N-oxide thereof, decreases the activity of an ER having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C.

In some embodiments, a compound of Formula (A), (B), (C) or (D), or a pharmaceutically acceptable salt, or N-oxide thereof, antagonizes a mutant ER. In some embodiments, a compound of Formula (A), (B), (C) or (D), or a pharmaceutically acceptable salt, or N-oxide thereof, antagonizes a wild-type ER. In some embodiments, a compound of Formula (A), (B), (C) or (D), or a pharmaceutically acceptable salt, or N-oxide thereof, antagonizes a mutant ER-α having one wild-type ER-α polypeptide and one mutant ER-α polypeptide (i.e., a heterodimer). In some embodiments, a compound of Formula (A), (B), (C) or (D), or a pharmaceutically acceptable salt, or N-oxide thereof, antagonizes a mutant ER-α having two mutant ER-α polypeptides (i.e., a homodimer). In some embodiments, a compound of Formula (A), (B), (C) or (D), or a pharmaceutically acceptable salt, or N-oxide thereof, antagonizes a mutant ER-α in a cell that expresses both a wild-type and mutant ER-α (i.e., heterogeneous expression). In some embodiments, a compound of Formula (A), (B), (C) or (D), or a pharmaceutically acceptable salt, or N-oxide thereof, antagonizes a wild-type ER-α in a cell that expresses both a wild-type and mutant ER. In some embodiments, a compound of Formula (A), (B), (C) or (D), or a pharmaceutically acceptable salt, or N-oxide thereof, antagonizes a mutant ER-α in a cell that expresses only mutant ER-α (i.e., homogeneous expression). In some embodiments, a compound of Formula (A), (B), (C) or (D), or a pharmaceutically acceptable salt, or N-oxide thereof, antagonizes an ER having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, a compound of Formula (A), (B), (C) or (D), or a pharmaceutically acceptable salt, or N-oxide thereof, antagonizes an ER having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C.

In some embodiments, a compound of Formula (A), (B), (C) or (D), or a pharmaceutically acceptable salt, or N-oxide thereof, lowers the cellular concentration of a mutant ER. In some embodiments, a compound of Formula (A), (B), (C) or (D), or a pharmaceutically acceptable salt, or N-oxide thereof, lowers the cellular concentration of a wild-type ER. In some embodiments, a compound of Formula (A), (B), (C) or (D), or a pharmaceutically acceptable salt, or N-oxide thereof, lowers the cellular concentration of a mutant ER-α having one wild-type ER-α polypeptide and one mutant ER-α polypeptide (i.e., a heterodimer). In some embodiments, a compound of Formula (A), (B), (C) or (D), or a pharmaceutically acceptable salt, or N-oxide thereof, lowers the cellular concentration of a mutant ER-α having two mutant ER-α polypeptides (i.e., a homodimer). In some embodiments, a compound of Formula (A), (B), (C) or (D), or a pharmaceutically acceptable salt, or N-oxide thereof, lowers the cellular concentration of a mutant ER-α in a cell that expresses both a wild-type and mutant ER-α (i.e., heterogeneous expression). In some embodiments, a compound of Formula (A), (B), (C) or (D), or a pharmaceutically acceptable salt, or N-oxide thereof, lowers the cellular concentration of a wild-type ER-α in a cell that expresses both a wild-type and mutant ER. In some embodiments, a compound of Formula (A), (B), (C) or (D), or a pharmaceutically acceptable salt, or N-oxide thereof, lowers the cellular concentration of a mutant ER-α in a cell that expresses only mutant ER-α (i.e., homogeneous expression). In some embodiments, a compound of Formula (A), (B), (C) or (D), or a pharmaceutically acceptable salt, or N-oxide thereof, lowers the cellular concentration an ER having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, a compound of Formula (A), (B), (C) or (D), or a pharmaceutically acceptable salt, or N-oxide thereof, lowers the cellular concentration an ER having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C.

The compounds of Formula (A), (B), (C) or (D), pharmaceutically acceptable salts, or N-oxides thereof, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, the compound of Formula (A), (B), (C) or (D) is an estrogen receptor antagonist. In some embodiments, compounds disclosed herein are selective estrogen receptor degrader compounds (SERDs). In some embodiments, the compound of Formula (A), (B), (C) or (D) is an estrogen receptor antagonist as well as an estrogen receptor degrader. In some embodiments, the compound of Formula (A), (B), (C) or (D) displays minimal or no estrogen receptor agonist activity. In some embodiments, in the context of treating cancers, the compound of Formula (A), (B), (C) or (D) offers improved therapeutic activity characterized by complete or longer-lasting tumor regression, a lower incidence or rate of development of resistance to treatment, and/or a reduction in tumor invasiveness. In some embodiments, compounds disclosed herein are estrogen receptor degraders that display full estrogen receptor antagonist activity with negligible or minimal estrogen receptor agonist activity. In some embodiments, the compound of Formula (A), (B), (C) or (D) are selective estrogen receptor modulators (SERMs) having tissue specific ER properties.

Diagnostic and Therapeutic Methods

Described herein, in certain embodiments, are methods for selecting patients for therapy with an estrogen receptor modulator. In some embodiments, the estrogen receptor modulator is a compound of Formula (A), (B), (C) or (D). In some embodiments, the methods comprise determining whether a patient has a mutation in the ESR1 gene. In some embodiments, the patient has an ER-mediated disease or condition. In some embodiments, the patient has cancer. In some embodiments, the patient has breast cancer. In some embodiments, the patient has an ER+ breast cancer. In some embodiments, the patient has a hormone resistant breast cancer. In some embodiments, the patient has a hormone resistant ER+ breast cancer. In some embodiments, the patient exhibits disease progression following hormonal therapy. In some embodiments, the patient exhibits disease progression following anti-estrogen therapy. In some embodiments, the breast cancer is not amenable to resection or radiation therapy with curative intent. In some embodiments, the breast cancer has progressed after at least 6 months of hormonal therapy for estrogen receptor positive breast cancer. In some embodiments, the breast cancer previously progressed in the presence of therapy with fulvestrant. In some embodiments, the breast cancer previously progressed in the presence of therapy with an aromatase inhibitor. In some embodiments, the breast cancer previously progressed in the presence of therapy with anastrazole, letrozole or exemestane.

In some embodiments, a method for selecting a patient having a hormone resistant estrogen receptor (ER) positive breast cancer for therapy with an estrogen receptor modulator of Formula (A), (B), (C) or (D) comprises: a) determining whether the patient has a mutation in the ESR1 gene; and b) selecting the patient for therapy if the patient has the mutation. In some embodiments, the estrogen receptor modulator of Formula (A), (B), (C) or (D) is a Selective Estrogen Receptor Degrader (SERD). In some embodiments, the mutation results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene. In some embodiments, the mutation is a translocation that results in an ER-YAP1 fusion polypeptide.

In some embodiments, the patient exhibits disease progression following hormonal therapy. In some embodiments, the patient exhibits disease progression following anti-estrogen therapy. In some embodiments, the breast cancer is not amenable to resection or radiation therapy with curative intent. In some embodiments, the breast cancer has progressed after at least 6 months of hormonal therapy for estrogen receptor positive breast cancer. In some embodiments, the breast cancer previously progressed in the presence of therapy with fulvestrant. In some embodiments, the breast cancer previously progressed in the presence of therapy with an aromatase inhibitor. In some embodiments, the breast cancer previously progressed in the presence of therapy with anastrazole, letrozole or exemestane.

In some embodiments, a method for determining whether the patient has a mutation in the ESR1 gene comprises testing a sample containing one or more tumor cells. In some embodiments, the sample is a tumor biopsy sample or a fluid sample (e.g. a blood or lymph sample). In some embodiments, the sample comprises one or more circulating tumor cells (CTCs) tumor cells. Accordingly, in some embodiments, the mutational status of ESR1 is assessed in a sample containing one or more tumor cells. In some embodiments, the mutational status of the ESR1 gene is assessed in a sample containing one or more CTCs. In some embodiments, a sample containing one or more circulating tumor cells is isolated from a patient. In some embodiments, the patient has breast cancer. In some embodiments, the patient has ER positive breast cancer. In some embodiments, the patient has metastatic breast cancer. In some embodiments, the patient has been previously treated with one or more anticancer agents. In some embodiments, the patient has been previously treated with one or more hormone therapies.

In some embodiments, the CTCs are assayed for the presence or absence of one or more ESR1 mutations. In some embodiments, the ESR1 mutations confer ligand-independent activity of the encoded ER polypeptide. In some embodiments, an ESR1 mutation that results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2 is determined. In some embodiments, an ESR1 mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C is determined. In some embodiments, a mutation that is a translocation that results in an ER-YAP1 fusion polypeptide is determined.

In some embodiments, the samples containing one or more tumor cells are assayed for the presence or absence of one or more additional gene mutations. In some embodiments, the samples containing one or more tumor cells are assayed for the presence or absence of one or more additional gene mutations selected from among mutations in a gene selected from among BRCA1, BRCA2, CDH1, STK11, TP53, PIK3CA, PTEN, EGFR (ERBB1), HER2 (ERBB2), AR, ATM, BARD1, BRIP1, CHEK2, DIRAS3, ERBB2, NBN, PALB2, RAD50, and RAD51.

In some embodiments, nucleic acid encoding the ER is isolated from the samples containing one or more tumor cells. In some embodiments, nucleic acid encoding the ER is isolated from the circulating tumor cells.

In some embodiments, the percentage of tumor cells having one or more mutations in the ESR1 gene in a sample is determined. In some embodiments, a therapeutic prognosis is determined based on the percentage of tumor cells having one or more mutations in the ESR1 gene.

In some embodiments, the percentage of CTCs having one or more mutations in the ESR1 gene is determined. In some embodiments, a therapeutic prognosis is determined based on the percentage of CTCs having one or more mutations in the ESR1 gene.

In some embodiments, the sample containing one or more tumor cells is cultured in vitro following isolation from the patient. In some embodiments, the sample containing one or more tumor cells is cultured in vitro prior to assaying for the presence or absence of one or more ESR1 mutations.

In some embodiments, the sample containing one or more circulating tumor cells (CTCs) is cultured in vitro following isolation from the patient. In some embodiments, the circulating tumor cells (CTCs) are cultured in vitro prior to assaying for the presence or absence of one or more ESR1 mutations.

In some embodiments, the ESR1 mutational status of a patient is monitored over time. In some embodiments, ESR1 mutational status of a patient is monitored over the course of a cancer treatment. In some embodiments, ESR1 mutational status of a patient is assessed one or more times over the course of a cancer treatment. In some embodiments, ESR1 mutational status of a patient is assessed every week, every 2 weeks, every 3 weeks, every 4 weeks, every month, every 2 months, every 3 months, every 4 months, every 5 months, every 6 months, every 7 months, every 8 months, every 9 months, every 10 months, every 11 months, every year, every 2 years, every 3 years, every 4 years, every 5 years, or longer time period.

Activities of the compounds provided herein can be assayed using standard methods well-known in the art, including, but not limited to in vitro assays, such as reporter assays, binding assays, and cell viability assays or in vivo assays, including xenograft tumor animal models.

In some embodiments, the tumor sample is from any tissue or fluid from an organism. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a tumor biopsy sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In particular embodiments, the sample is a serum sample. In some embodiments, the sample contains one or more circulating tumor cells (CTCs). In some embodiments, the sample contains one or more disseminated tumor cells (DTC, e.g. in a bone marrow aspirate sample).

Methods for the isolation of nucleic acids and proteins from cells contained in tissue and fluid samples are well-known in the art. In particular embodiments, the nucleic acid sample obtained from the subject is isolated from cells contained in a tumor biopsy from the subject. In particular embodiments, the nucleic acid sample obtained from the subject is isolated from cells in a bone marrow aspirate. In particular embodiments, the nucleic acid sample obtained from the subject is isolated from cells contained in a blood sample. In particular embodiments, the nucleic acid sample obtained from the subject is isolated from cells contained lymphatic fluid sample. In some embodiments, the cell is a circulating tumor cell (CTC).

In some embodiments, the samples are obtained from the subject by any suitable means of obtaining the sample using well-known and routine clinical methods. Procedures for obtaining fluid samples from a subject are well known. For example, procedures for drawing and processing whole blood and lymph are well-known and can be employed to obtain a sample for use in the methods provided. Typically, for collection of a blood sample, an anti-coagulation agent (e.g. EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the sample is a tissue biopsy and is obtained, for example, by needle biopsy, CT-guided needle biopsy, aspiration biopsy, endoscopic biopsy, bronchoscopic biopsy, bronchial lavage, incisional biopsy, excisional biopsy, punch biopsy, shave biopsy, skin biopsy, bone marrow biopsy, and the Loop Electrosurgical Excision Procedure (LEEP). Typically, a non-necrotic, sterile biopsy or specimen is obtained that is greater than 100 mg, but which can be smaller, such as less than 100 mg, 50 mg or less, 10 mg or less or 5 mg or less; or larger, such as more than 100 mg, 200 mg or more, or 500 mg or more, 1 gm or more, 2 gm or more, 3 gm or more, 4 gm or more or 5 gm or more. The sample size to be extracted for the assay depends on a number of factors including, but not limited to, the number of assays to be performed, the health of the tissue sample, the type of cancer, and the condition of the patient. In some embodiments, the tissue is placed in a sterile vessel, such as a sterile tube or culture plate, and is optionally immersed in an appropriate media. Typically, the cells are dissociated into cell suspensions by mechanical means and/or enzymatic treatment as is well known in the art. Typically, the cells are collected and then subjected to standard procedures for the isolation of nucleic acid for the assay.

In some embodiments, the samples are obtained from the subject at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly. In some embodiments, the collection of samples is performed at a predetermined time or at regular intervals relative to treatment with one or more anti-cancer agents. In some embodiments, the collection of samples is performed at a predetermined time or at regular intervals relative to treatment with a hormonal therapy. For example, a sample is collected at a predetermined time or at regular intervals prior to, during, or following treatment or between successive treatments. In particular examples, a sample is obtained from the subject prior to administration of an anti-cancer therapy and then again at regular intervals after treatment has been effected. In particular examples, a sample is obtained from the subject prior to administration of a hormonal therapy and then again at regular intervals after treatment has been effected.

The volume of a fluid sample can be any volume that is suitable for the detection of an ER mutant in the methods provided. In some examples, the volume for the fluid sample is dependent on the particular assay method used. For example, particular assay methods can require a larger or smaller fluid sample volumes depending on factors such as, but not limited to, the capacity of the device or method used and level of throughput of the assay method. In some examples a fluid sample is diluted in an appropriate medium prior to application of the assay method. In some examples, a fluid sample is obtained from a subject and a portion or aliquot of the sample is used in the assay method. The portion or aliquot can be diluted in an appropriate medium prior to application of the assay method.

In some embodiments, the sample is obtained from a subject that is a mammal. Exemplary mammalian subjects include, but are not limited to primates, such as humans, apes and monkeys; rodents, such as mice, rats, rabbits, and ferrets; ruminants, such as goats, cows, deer, and sheep; horses, pigs, dogs, cats, and other animals. In some embodiments, the sample is obtained from a patient. In some examples, the patient is a human patient.

In some embodiments, the nucleic acid sample obtained from the subject is a genomic nucleic acid sample. In some embodiments, the nucleic acid sample obtained from the subject is an RNA sample. In some embodiments, mRNA is isolated from the total RNA in an RNA sample. In some embodiments, the RNA sample is reverse transcribed into cDNA. In some embodiments, the genomic nucleic acid sample is amplified by a nucleic acid amplification method. In some embodiments, the nucleic acid amplification method is polymerase chain reaction (PCR). In some embodiments, the genomic nucleic acid sample is amplified using a set of nucleotide primers specific for the ER gene. In some embodiments, the set of nucleotide primers flank the nucleic acid sequence encoding mutant amino acid position of the ER polypeptide. In some embodiments, the amplification product is a nucleic acid encoding the mutant amino acid position of the ER polypeptide. In some embodiments, a sequence specific primer is conjugated to a detectable molecule, such as a fluorescent label, a bioluminescent label, a chemiluminescent label, a radiolabel, an enzyme label, a detectable substrate, or a peptide or molecule that binds to a second detectable molecule.

In some embodiments, the sample is a plasma or serum sample containing circulating tumor DNA (ctDNA), RNA (ctRNA) or microRNA (see e.g. Chan et al. (2007) *Br J Cancer* 96(5):681-5). In some embodiments, the nucleic acid is isolated from the sample prior to detection.

Detection Methods

In some embodiments, assaying comprises sequencing the nucleic acid sample. In some embodiments, the nucleic acid encoding ER in a nucleic acid sample is first amplified by a method such as polymerase chain reaction (PCR) using sequence specific primers, and the amplified PCR fragment is then sequenced. Exemplary sequencing methods for use in the methods provide herein are well known in the art and include, but are not limited to, dideoxy or chain termination methods, Maxam-Gilbert sequencing, massively parallel signature sequencing (or MPSS), polony sequencing, pyrosequencing, Illumina dye sequencing, SOLiD (or sequencing by ligation) sequencing, ion semiconductor sequencing, DNA nanoball sequencing, heliscope sequencing, and single molecule real time (SMRT) sequencing.

In some embodiments, the DNA encoding the mutant ER-α is assessed by BEAMing (beads, amplification, emulsion, magnetic) PCR sequencing method (see, e.g. Li et al. (2006) *Nat Methods* 3(2):95-7; Li et al. (2006) *Nat Methods* 3(7):551-9; and Diehl et al. (2008) *Nat Med.* 14(9): 985-990). BEAMing is a technique in which individual DNA molecules are attached to magnetic beads in water-in-oil emulsions and then subjected to compartmentalized PCR amplification. The mutational status of DNA bound to beads is then determined by hybridization to fluorescent allele-specific probes for mutant or wild-type ER. Flow cytometry is then used to quantify the level of mutant DNA present in the plasma or serum (see e.g. Higgins et al. (2012) *Clin Cancer Res* 18: 3462-3469).

In some embodiments, the DNA encoding the mutant ER-α is assessed by clonal amplification of nucleic acid sample. In some embodiments, the DNA encoding the mutant ER-α is assessed by digital polymerase chain reaction. In some embodiments, the DNA encoding the mutant ER-α is assessed by droplet digital polymerase chain reaction.

In some embodiments, assaying a sample for detecting the presence of DNA encoding the mutant ER-α comprises detection of the mutation with a sequence specific oligonucleotide probe that is specific for nucleic acid that encodes the mutant ER-α but not the wild-type ER. In some embodiments, assaying comprises (a) contacting a sample with a mutant ER-α nucleic acid sequence specific oligonucleotide probe, whereby if the mutant nucleic acid sequence is present in the sample, a probe-DNA complex is formed, and (b) detecting the probe-DNA complex. In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule.

In some embodiments, single nucleotide changes are detectable by PCR using PCR-based cleaved amplified polymorphic sequences (CAPS) markers which create restriction sites in the mutant sequences (Michaels et al (1998) *Plant J.* 14(3):381-5) or sequence specific hairpin probes attached to detectable moieties, such as, but not limited to, a fluorophore (Mhlanga and Malmberg (2001) *Methods* 25:463-471). In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule.

In some embodiments, assaying a sample for detecting the presence of DNA encoding the mutant ER-α is performed using an oligonucleotide array (see e.g. Hastia et al. (1999) *J Med Genet.* 36(10):730-6). In some embodiments, the sample containing nucleic acid from the subject is hybridized directly to the chip. In some embodiments, the sample containing nucleic acid from the subject is amplified using an amplification method, such as, but not limited to polymerase chain reaction (PCR), and the amplified nucleic acid is hybridized to the chip. In some embodiments, the oligonucleotide array is contained on a microchip. In some embodiments, single nucleotide changes are detectable using microchips.

In some embodiments, assaying a sample comprises detection of the mutation with an antibody specific for the mutant ER-α polypeptide. In some embodiments, the method of detecting a mutant ER-α polypeptide comprises obtaining a sample from a subject, wherein the sample comprises an ER polypeptide and testing the sample for the presence of a mutant ER-α polypeptide by contacting the sample with an antibody that is specific for binding to the mutant ER-α polypeptide, and does not bind or bind with decreased affinity for the wild-type ER-α polypeptide, wherein the presence of the mutant ER-α polypeptide creates an antibody-mutant ER-α polypeptide complex. In some embodiments, the method further comprises detecting the antibody-mutant ER-α polypeptide complex. In some embodiments, the method further comprises detecting the antibody-mutant ER-α polypeptide complex with a detection reagent. In some embodiments, the mutant ER-α specific antibody is conjugated to a detectable molecule, such as a fluorescent label, a bioluminescent label, a chemiluminescent label, a radiolabel, an enzyme label, a detectable substrate, or a peptide or molecule that binds to a second detectable protein (e.g. a secondary antibody). In some embodiments, binding of the mutant ER-α specific antibody is detected by assaying for the detectable molecule. In some embodiments, binding of the mutant ER-α specific antibody is detected by using a secondary (e.g. anti-IgG) antibody. In some embodiments, the sample is a tumor biopsy sample, a bone marrow aspirate, a blood sample, a serum sample, or a lymph sample.

Estrogen Receptor Modulator In Vitro Activity

The cytotoxic or cytostatic activity of combinations of estrogen receptor modulator (ERM) compounds, including but not limited to those in Tables 1-4, is measured by: establishing a proliferating mammalian tumor cell line in a cell culture medium, adding a test compound, culturing the cells for a period from about 6 hours to about 5 days; and measuring cell viability (Example 7). Cell-based in vitro assays were used to measure viability, i.e. proliferation ($IC_{50}$), cytotoxicity ($EC_{50}$), and induction of apoptosis (caspase activation).

The in vitro potency of ERM compounds is measured by the cell proliferation assay of Example 7; the CellTiter-Glo® Luminescent Cell Viability Assay, commercially available from Promega Corp., Madison, Wis. This homogeneous assay method is based on the recombinant expression of Coleoptera luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The anti-proliferative effects of combinations of ERM compounds were measured by the CellTiter-Glo® Assay (Example 7) against tumor cell lines. $EC_{50}$ values are established for the tested compounds and combinations. The range of in vitro cell potency activities may be about 100 nM to about 10 µM.

Estrogen Receptor Modulator In Vivo Tumor Xenograft Activity

The efficacy of ERM compounds and various chemotherapeutic agents was measured in vivo by implanting allografts or xenografts of cancer cells in rodents and treating the tumor-bearing animals with the drug and control (Vehicle) formulations. Results are dependent on the cell line, the presence or absence of certain mutations in the tumor cells, the sequence of administration of ERM compounds and chemotherapeutic agent, dosing regimen, and other factors. Subject mice were treated with drug(s) or control (Vehicle) and monitored over several weeks or more to measure the time to tumor doubling, log cell kill, and tumor inhibition (Example 8). FIGS. 1-13 show plots of antitumor volume change over time after treatment of tumorbearing mice treated with ERM compounds and various chemotherapeutic agents according to the protocol of Example 8.

Figure 2:
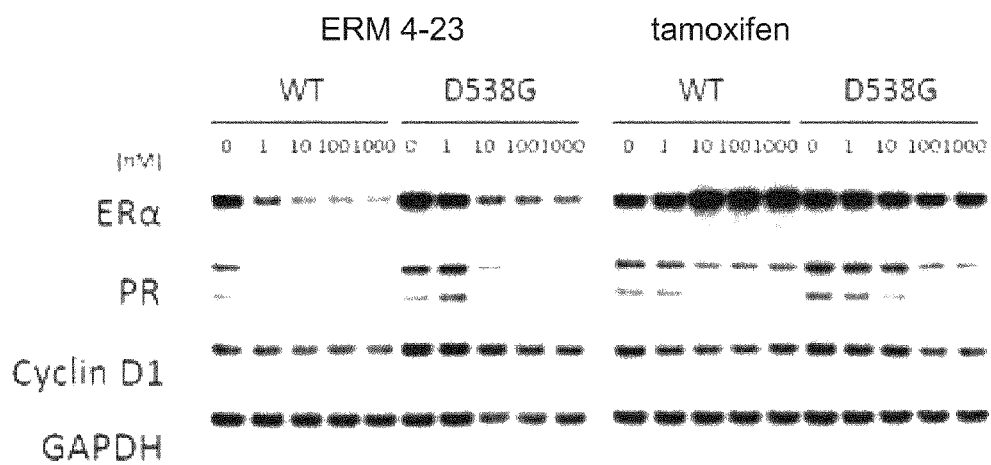

FIGS. 1 and 2 show ERα degradation assay in MCF7 inducibly expressing WT and mutant ERα in the absence of E2. Cells were treated with increasing doses of fulvestrant (FIG. 1) for 24 hr in the estrogen-depleted medium containing 100 ng/ml Dox. Mutant ERa degradation was observed with estrogen receptor modulator (ERM) 1-3 from Table 1 (FIG. 1) and ERM 4-23 (FIG. 2), but not tamoxifen (FIG. 2). Functional output is evident by the PR and cyclin D1 levels.

Figure 3:
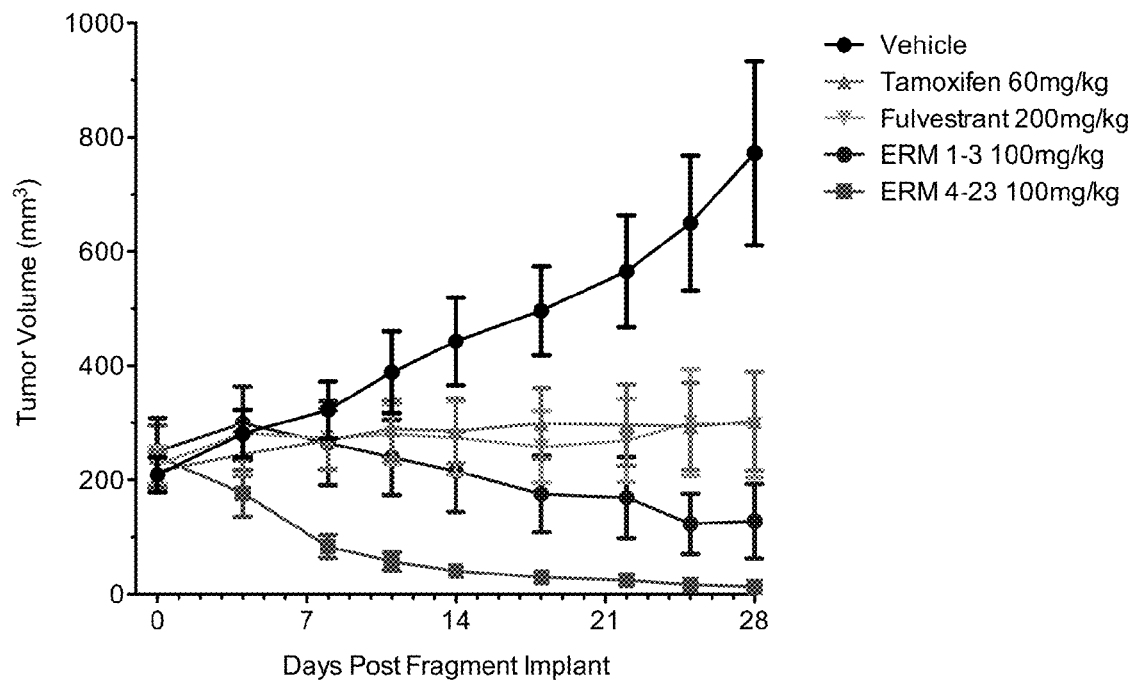
FIG. 3 shows the fitted tumor volume change over 28 days in cohorts of 7 immunocompromised mice bearing MCF-7 EF1:Y537S ESR1-mutant (Y537S) mouse, dosed once daily PO (oral) administration with Vehicle, fulvestrant at high dose, 200 mg/kg; AUC about 20-30× above clinical exposure, and estrogen receptor modulator (ERM) 1-3 from Table 1 at 100 mg/kg/day and ERM 4-23 from Table 4 at 100 mg/kg/day.

FIG. 3 shows the fitted tumor volume change over 28 days in cohorts of 7 immunocompromised mice bearing MCF-7 EF1:Y537S ESR1-mutant (Y537S) mouse, dosed once daily PO (oral) administration with Vehicle, fulvestrant at high dose, 200 mg/kg; AUC about 20-30× above clinical exposure, and estrogen receptor modulator (ERM) 1-3 from Table 1 at 100 mg/kg/day and ERM 4-23 from Table 4 at 100 mg/kg/day. The engineered MCF7 mutant cells express protein 4-5× above endogenouse wild-type (WT) MCF7 cells. Fulvestrant does not show robust in vivo efficacy even at 30× above clinical exposure, and in the absence of E2.

Figure 4:
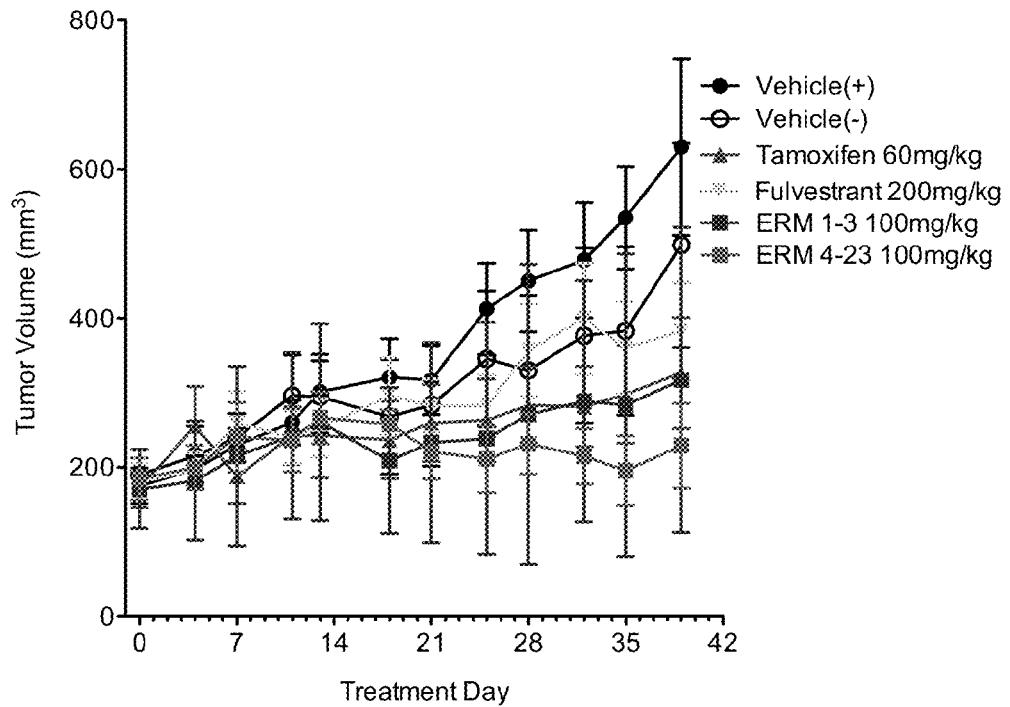
FIG. 4 shows the fitted tumor volume change over 40 days in cohorts of 5 immunocompromised mice bearing HCl-005 breast tumor (BC PDX model in NOD.SCID OVX) xenografts harboring ESR1 L536P mutant, ER+, PR+, HER2+, dosed once daily by PO (oral) administration with Vehicle (+), Vehicle (−), tamoxifen at 60 mg/kg/day, fulvestrant at 200 mg/kg (QD 3×/wk), ERM 1-3 at 100 mg/kg/day, and ERM 4-23 at 100 mg/kg/day. Vehicle (+) is solvent/buffer with ethynyl estradiol (0.1 mg/kg). Vehicle (−) is solvent/buffer without ethynyl estradiol.

FIG. 4 shows the fitted tumor volume change over 40 days in cohorts of 5 immunocompromised mice bearing HCl-005 breast tumor (BC PDX model in NOD.SCID OVX) xenografts harboring ESR1 L536P mutant, ER+, PR+, HER2+, dosed once daily by PO (oral) administration with Vehicle (+E2), Vehicle (−E2), tamoxifen at 60 mg/kg/day, fulvestrant at 200 mg/kg (QD 3×/wk), ERM 1-3 at 100 mg/kg/day, and ERM 4-23 at 100 mg/kg/day. ERM 4-23 has greater efficacy than ERM 1-3 in this ESR1 L536P mutant model.

Figure 5:
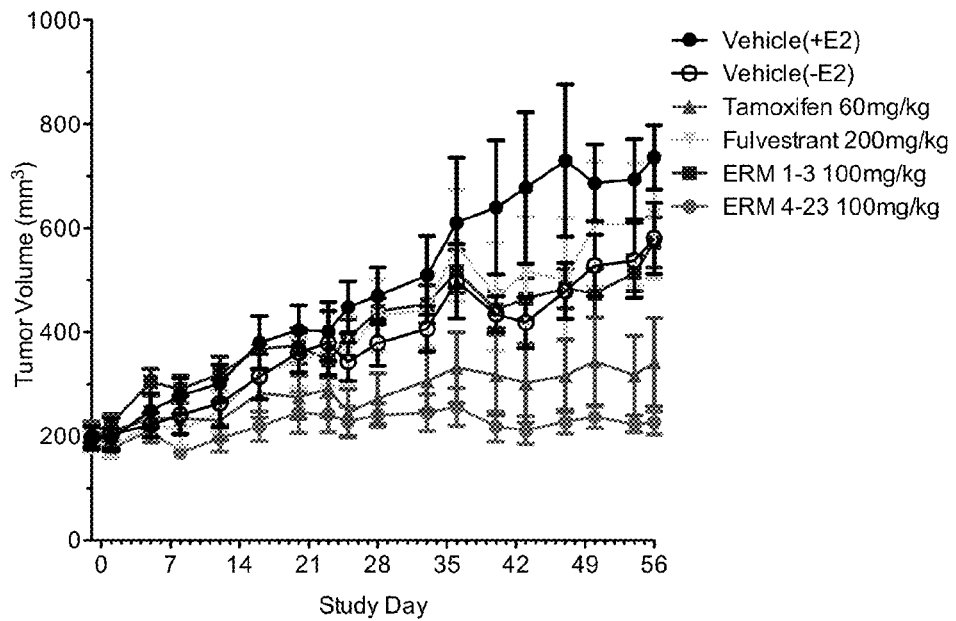
FIG. 5 shows the fitted tumor volume change over 56 days with Fold Over Start in cohorts of 7 immunocompromised mice bearing HCl-005 breast tumor (BC PDX model in NOD.SCID OVX) xenografts harboring ESR1 L536P mutant, ER+, PR+, HER2+, dosed once daily PO (oral) administration with Vehicle (+E2), Vehicle (−E2), tamoxifen at 60 mg/kg/day, fulvestrant at 200 mg/kg (QD 3×/wk), ERM 1-3 at 100 mg/kg/day, and ERM 4-23 at 100 mg/kg/day. Vehicle (+E2) is solvent/buffer with ethynyl estradiol (0.1 mg/kg). Vehicle (−E2) is solvent/buffer without ethynyl estradiol.

FIG. 5 shows the fitted tumor volume change over 56 days with Fold Over Start in cohorts of 7 immunocompromised mice bearing HCl-005 breast tumor (BC PDX model in NOD.SCID OVX) xenografts harboring ESR1 L536P mutant, ER+, PR+, HER2+, dosed once daily PO (oral) administration with Vehicle (+E2), Vehicle (−E2), tamoxifen at 60 mg/kg/day, fulvestrant at 200 mg/kg (QD 3×/wk), ERM 1-3 at 100 mg/kg/day, and ERM 4-23 at 100 mg/kg/day.

Figure 6:
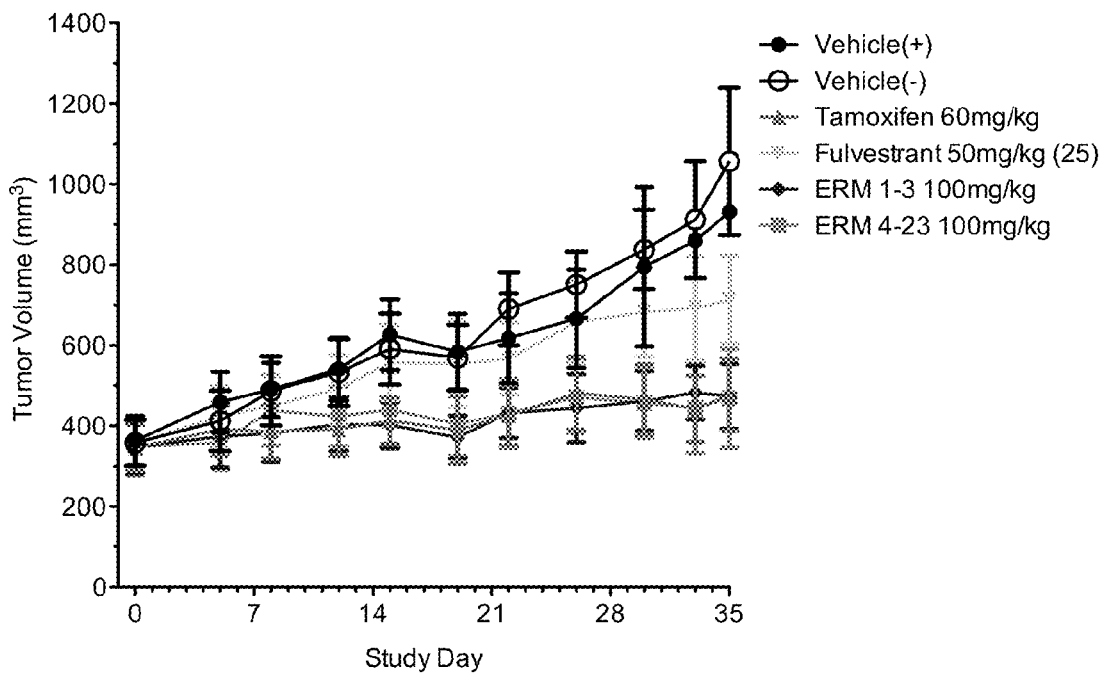
FIG. 6 shows the fitted tumor volume change over 35 days in cohorts of 7-8 immunocompromised mice bearing WHIM 20 Y537S ESR1-mutant (Y537S), PIK3CA mutant (E542K) breast tumor (BC PDX model in NOD.SCID OVX) xenografts, dosed once daily PO (oral) administration with Vehicle (+E2), Vehicle (−E2), tamoxifen citrate at 60 mg/kg/day, fulvestrant at 50 mg/kg, ERM 1-3 at 100 mg/kg/day, and ERM 4-23 at 100 mg/kg/day.

FIG. 6 shows the fitted tumor volume change over 35 days in cohorts of 7-8 immunocompromised mice bearing WHIM 20 Y537S ESR1-mutant (Y537S), PIK3CA mutant (E542K) breast tumor (BC PDX model in NOD.SCID OVX) xenografts, dosed once daily PO (oral) administration with Vehicle (+E2), Vehicle (−E2), tamoxifen citrate at 60 mg/kg/day, fulvestrant at 50 mg/kg, ERM 1-3 at 100 mg/kg/day, and ERM 4-23 at 100 mg/kg/day.

Figure 7:
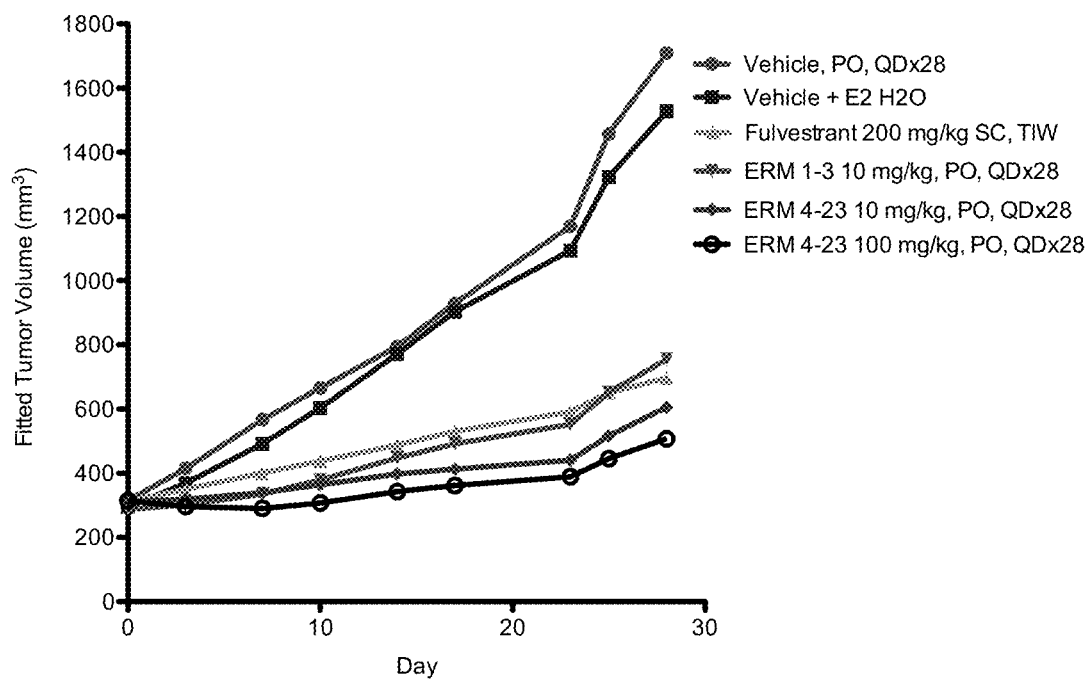
FIG. 7 shows the fitted tumor volume change over 28 days in cohorts of 7 immunocompromised mice bearing WHIM 20 Y537S ESR1-mutant (Y537S), PIK3CA mutant (E542K) breast tumor (BC PDX model in NSG OVX) xenografts, dosed daily by PO (oral) administration with Vehicle (+E2), Vehicle (−E2), fulvestrant at 200 mg/kg subcutaneous three times per week, ERM 1-3 at 10 mg/kg/day, and ERM 4-23 at 10 and 100 mg/kg/day.

FIG. 7 shows the fitted tumor volume change over 28 days in cohorts of 7 immunocompromised mice bearing WHIM 20 Y537S ESR1-mutant (Y537S), PIK3CA mutant (E542K) breast tumor (BC PDX model in NSG OVX) xenografts, dosed daily by PO (oral) administration with Vehicle (+E2), Vehicle (−E2), fulvestrant at 200 mg/kg subcutaneous three times per week, ERM 1-3 at 10 mg/kg/day, and ERM 4-23 at 10 and 100 mg/kg/day.

Figure 8:
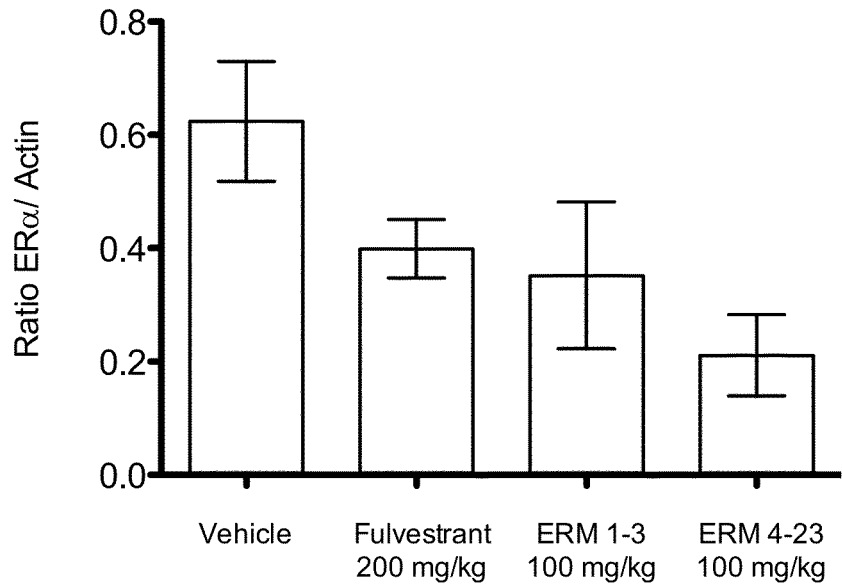
FIGS. 8 and 9 show bar plots of the ratio of ERα (alpha) to actin protein levels (FIG. 8) and the ratio of PR-A to actin protein levels (FIG. 9) in immunocompromised mice bearing WHIM 20 Y537S ESR1-mutant (Y537S), PIK3CA mutant (E542K) breast tumor, patient derived (BC PDX model) xenograft model dosed once daily for 4 days by 100 microliter (μl) PO (oral) administration with Vehicle, fulvestrant at 200 mg/kg, ERM 1-3 at 100 mg/kg, and ERM 4-23 at 100 mg/kg.
Figure 9:
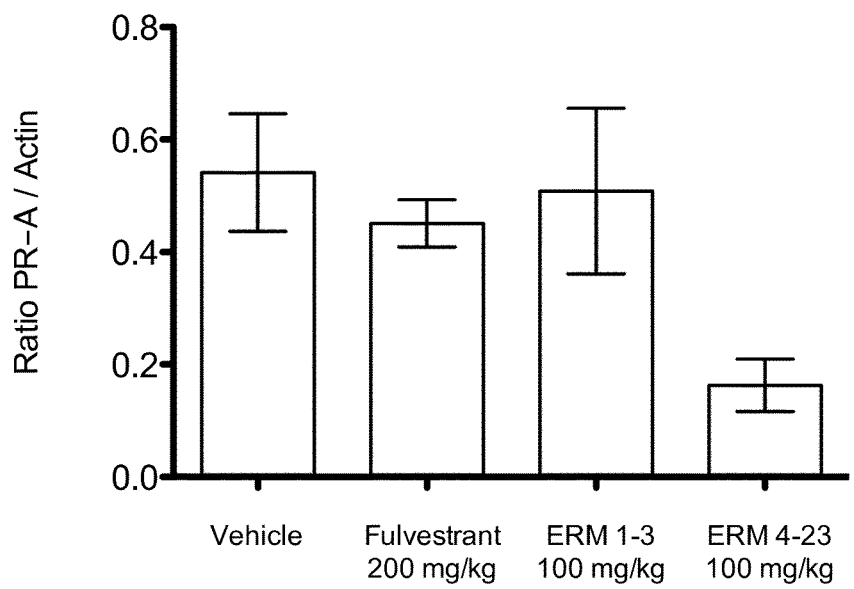

FIGS. 8 and 9 show bar plots of the ratio of ERα (alpha) to actin protein levels (FIG. 8) and the ratio of PR-A to actin protein levels (FIG. 9) in immunocompromised mice bearing WHIM 20 Y537S ESR1-mutant (Y537S), PIK3CA mutant (E542K) breast tumor, patient derived (BC PDX model) xenograft model dosed once daily for 4 days by 100 microliter (µl) PO (oral) administration with Vehicle, fulvestrant at 200 mg/kg, ERM 1-3 at 100 mg/kg, and ERM 4-23 at 100 mg/kg.

ERM 1-3 and ERM 4-23 demonstrated a range of antitumor activity from tumor regressions to tumor growth delay in ER mutant breast cancer xenograft models. Moreover, ERM 1-3 and ERM 4-23 were efficacious in models in which primary or metastatic tumors from patients were engrafted in immunocompromised mice (also referred to as patient derived xenograft models). Pharmacodynamic activity of ERM 1-3 and ERM 4-23 was observed in a patientderived xenograft model based on decreased ER protein levels and reduction in progesterone receptor levels: an ER target gene. Additionally, in one model ERM 1-3 and ERM 4-23 was more efficacious than standard-of-care drugs (fulvestrant or tamoxifen) and in other models a trend towards improved efficacy was observed.

Treatment of ER-Related Diseases or Conditions

In some embodiments, provided are methods of treatment of a patient having one or more mutations in the ESR1 gene. In some embodiments, treatment comprises administration of a compound of Formula (A), (B), (C) or (D) to a patient having one or more mutations in the ESR1 gene. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene. In some embodiments, the mutation is a translocation that results in an ER-YAP1 fusion polypeptide. In some embodiments, the patient has cancer. In some embodiments, the patient has a solid tumor. In some embodiments, the cancer is a breast cancer, an ovarian cancer, an endometrial cancer, uterine cancer, cervical cancer a prostate cancer, a liver cancer, a lung cancer or a bladder cancer. In some embodiments, the cancer is a breast cancer. In some embodiments, the cancer is an estrogen positive breast cancer. In some embodiments, the cancer is HER2 positive breast cancer. In some embodiments, the cancer is HER2 negative breast cancer. In some embodiments, the cancer is a metastatic cancer. In some embodiments, the cancer is a metastatic breast cancer.

In some embodiments, the cancer is a hormone dependent cancer. In some embodiments, the cancer is an estrogen receptor dependent cancer. In some embodiments, the cancer is an estrogen receptor positive cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors-resistant. In some embodiments, anti-hormonal treatment includes treatment with anastrazole, letrozole or exemestane.

In some embodiments, the patient treated with a compound of Formula (A), (B), (C) or (D) is a woman with disease progression following anti-estrogen therapy. In some embodiments, the patient treated with a compound of Formula (A), (B), (C) or (D) is a woman with disease progression following therapy with an aromatase inhibitor. In some embodiments, the patient treated with a compound of Formula (A), (B), (C) or (D) is a woman with disease progression following therapy with anastrazole, letrozole or exemestane.

In some embodiments, the patient treated with a compound of Formula (A), (B), (C) or (D) is a postmenopausal woman. In some embodiments, the patient treated with a compound of Formula (A), (B), (C) or (D) is a postmenopausal woman with disease progression following anti-estrogen therapy. In some embodiments, the patient treated with a compound of Formula (A), (B), (C) or (D) is a postmenopausal woman with disease progression following therapy with an aromatase inhibitor. In some embodiments, the patient treated with a compound of Formula (A), (B), (C) or (D) is a postmenopausal woman with disease progression following therapy with anastrazole, letrozole or exemestane.

In some embodiments, the patient treated with a compound of Formula (A), (B), (C) or (D) is chemotherapy-naïve.

In some embodiments, the patient treated with a compound of Formula (A), (B), (C) or (D) is being treated for cancer with at least one anti-cancer agent. In one embodiment, the cancer is a hormone refractory cancer.

In some embodiments, the compound of Formula (A), (B), (C) or (D) is used in the treatment of an ER-related disease or condition in a patient having one or more ESR1 mutations. Exemplary ER-related diseases or conditions including, but not limited to, ER-α dysfunction associated with cancer (e.g. bone cancer, breast cancer, colorectal cancer, lung cancer, endometrial cancer, prostate cancer, ovarian and uterine cancer), endometriosis, uterine fibroids, leiomyoma (e.g. uterine leiomyoma), central nervous system (CNS) defects (e.g. alcoholism, migraine), cardiovascular system defects (e.g. aortic aneurysm, susceptibility to myocardial infarction, aortic valve sclerosis, cardiovascular disease, coronary artery disease, hypertension), hematological system defects (e.g. deep vein thrombosis), immune and inflammation diseases (e.g. Graves' Disease, arthritis, multiple sclerosis, cirrhosis), susceptibility to infection (e.g. hepatitis B, chronic liver disease), metabolic defects (e.g. bone density, cholestasis, hypospadias, obesity, osteoarthritis, osteopenia, osteoporosis), neurological defects (e g Alzheimer's disease, Parkinson's disease, migraine, vertigo), psychiatric defects (e.g. anorexia nervosa, attention deficit hyperactivity disorder (ADHD), dementia, major depressive disorder, psychosis) and reproductive defects (e.g. age of menarche, endometriosis, infertility).

Also provided herein are methods of reducing ER activation in a patient having one or more ESR1 mutation comprising administering to the mammal at least one compound having the structure of Formula (A), (B), (C) or (D), or a pharmaceutically acceptable salt, or N-oxide thereof. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

Routes of Administration

Suitable routes of administration of an estrogen receptor modulator compound as described herein include, but are not limited to, oral, parenteral (e.g., intravenous, subcutaneous, intramuscular), intranasal, buccal, topical, rectal, aerosol, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. In certain embodiments, an estrogen receptor modulator compound as described herein is administered in a systemic manner. In certain other embodiments an estrogen receptor modulator compound as described herein is administered in a local rather than systemic manner. In some embodiments, certain embodiments, an estrogen receptor modulator compound as described herein is administered orally.

Pharmaceutical Compositions/Formulations

In some embodiments, the estrogen receptor modulator compounds as described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

A pharmaceutical composition, as used herein, refers to a mixture of a compound of Formula (A), (B), (C) or (D), with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

The pharmaceutical compositions will include at least one compound of Formula (A), (B), (C) or (D), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like.

The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, enteric coated formulations, pulsatile release formulations, multiparticulate formulations, and mixed immediate and controlled release formulations.

In some embodiments, the compound of Formula (A), (B), (C) or (D), or a pharmaceutically acceptable salt thereof, is administered systemically.

In some embodiments, the compound of Formula (A), (B), (C) or (D), or a pharmaceutically acceptable salt thereof, is administered orally. All formulations for oral administration are in dosages suitable for such administration. In some embodiments, the solid dosage forms disclosed herein are in the form of a tablet, a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In still other embodiments, the pharmaceutical formulation is in the form of a suspension tablet, a fast-melt tablet, a bite-disintegration tablet, a rapid-disintegration tablet, an effervescent tablet, or a caplet. In other embodiments, pharmaceutical formulation is in the form of a capsule.

In some embodiments, the pharmaceutical solid oral dosage forms are formulated to provide a controlled release of the active compound. Controlled release profiles include, for example, sustained release, prolonged release, pulsatile release, and delayed release profiles.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

For buccal or sublingual administration, the compositions optionally take the form of tablets, lozenges, or gels formulated in a conventional manner.

In one aspect, a compound of Formula (A), (B), (C) or (D), or a pharmaceutically acceptable salt thereof, is formulated into a pharmaceutical composition suitable for intramuscular, subcutaneous, or intravenous injection. Parenteral injections involve either bolus injection and/or continuous infusion.

In some embodiments, the compound of Formula (A), (B), (C) or (D), or a pharmaceutically acceptable salt thereof, is administered intravenously. In some embodiments, the compound of Formula (A), (B), (C) or (D), or a pharmaceutically acceptable salt thereof, is administered subcutaneously.

In some embodiments, the compound of Formula (A), (B), (C) or (D), or a pharmaceutically acceptable salt thereof, is administered topically. In such embodiments, the compound of Formula (A), (B), (C) or (D), or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound of Formula (A), (B), (C) or (D), or a pharmaceutically acceptable salt thereof, is administered topically to the skin of mammal. In some embodiments, the compound of Formula (A), (B), (C) or (D), is prepared as a transdermal dosage form.

In another aspect is the use of a compound of Formula (A), (B), (C) or (D), or a pharmaceutically acceptable salt thereof, in the manufacture of a medicament for treating a disease, disorder or conditions in which the activity of estrogen receptors contributes to the pathology and/or symptoms of the disease or condition (e.g., a hormone-resistant cancer characterized by a mutation in the ESR1 gene). In one aspect, the disease or condition is any of the diseases or conditions specified herein.

A therapeutically effective amount of an estrogen receptor modulator, or a pharmaceutically acceptable salt thereof, can vary widely depending on the severity of the disease, the age and relative health of the subject, and other factors.

Dosing and Treatment Regimens

In one embodiment, the compound of Formula (A), (B), (C) or (D), or a pharmaceutically acceptable salt thereof, is used in the preparation of medicaments for the treatment of a patient having one or more ESR1 mutations, including diseases or conditions in a mammal that would benefit from a reduction of estrogen receptor activity (e.g., a hormone-resistant breast cancer characterized by a mutation in the ESR1 gene). Methods for treating any of the diseases or conditions described herein in a mammal in need of such treatment, involves administration of pharmaceutical compositions that include at least one compound of Formula (A), (B), (C) or (D), or a pharmaceutically acceptable salt, N-oxide, active metabolite, prodrug, or pharmaceutically acceptable solvate thereof, in therapeutically effective amounts to said patient.

Therapeutically effective amounts depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In any of the method of treatments described herein, the effective amount of the compound of Formula (A), (B), (C) or (D) is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In some situations the methods of treatment comprise single administration of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments wherein the patient's condition does not improve, upon the doctor's discretion the compound is administered chronically, that is, for an extended period of time.

In certain embodiments wherein a patient's status does improve, the dose of drug being administered is temporarily reduced or temporarily suspended for a certain length of time (i.e., a "drug holiday").

In some embodiments, doses employed for adult human treatment are typically in the range of 0.01 mg-5000 mg of a compound of Formula (A), (B), (C) or (D) per day. In one aspect, doses employed for adult human treatment are from about 1 mg to about 2000 mg of a compound of Formula (A), (B), (C) or (D) per day. In one embodiment, the desired dose is conveniently presented in a single dose or in divided doses administered simultaneously or at appropriate intervals, for example as two, three, four or more sub-doses per day. In one embodiment, the daily dosages appropriate for the compound of Formula (A), (B), (C) or (D), or a pharmaceutically acceptable salt thereof, described herein are from about 0.01 to about 50 mg/kg per body weight.

In some embodiments, an estrogen receptor modulator, or a pharmaceutically acceptable salt thereof, is administered orally to postmenopausal women.

In some embodiments, an estrogen receptor modulator of Formula (A), (B), (C) or (D), or a pharmaceutically acceptable salt thereof, is administered daily to the patient. In some embodiments, an estrogen receptor modulator of Formula (A), (B), (C) or (D), or a pharmaceutically acceptable salt thereof, is administered every other day to the patient. In some embodiments, an estrogen receptor modulator of Formula (A), (B), (C) or (D), or a pharmaceutically acceptable salt thereof, is administered daily, every other day, every third day, every fourth day, every fifth day, every sixth day, once a week, once every two weeks, once every three weeks, or once a month to the patient.

In some embodiments, an estrogen receptor modulator of Formula (A), (B), (C) or (D), or a pharmaceutically acceptable salt thereof, is administered orally to the patient on a continuous daily dosing schedule.

In some embodiments, about 5 mg per day to about 1000 mg per day of an estrogen receptor modulator of Formula (A), (B), (C) or (D), or a pharmaceutically acceptable salt thereof, is administered to the patient. In some embodiments, about 10 mg per day to about 100 mg per day of an estrogen receptor modulator of Formula (A), (B), (C) or (D), or a pharmaceutically acceptable salt thereof, is administered to the patient.

In some embodiments, about 10 mg per day, about 15 mg per day, about 20 mg per day, about 25 mg per day, about 30 mg per day, about 35 mg per day, about 35 mg per day, about 40 mg per day, about 45 mg per day, about 50 mg per day, about 55 mg per day, about 60 mg per day, about 65 mg per day, about 70 mg per day, about 75 mg per day, about 80 mg per day, about 85 mg per day, about 90 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, 850 mg per day, about 900 mg per day, about 950 mg per day, about 1000 mg per day of an estrogen receptor modulator of Formula (A), (B), (C) or (D), or a pharmaceutically acceptable salt thereof, is administered to the patient.

In some embodiments, about 600 mg per day of an estrogen receptor modulator of Formula (A), (B), (C) or (D), or a pharmaceutically acceptable salt thereof, is administered to the patient.

In some embodiments, about 1000 mg per day of an estrogen receptor modulator of Formula (A), (B), (C) or (D), or a pharmaceutically acceptable salt thereof, is administered to the patient.

In one embodiment, the desired daily dose is conveniently presented in a single dose or in divided doses administered simultaneously (or over a short period of time) or at appropriate intervals, for example as two, three, four or more sub-doses per day. In some embodiments, the desired daily dose is conveniently presented in divided doses that are administered simultaneously (or over a short period of time) once a day. In some embodiments, the desired daily dose is conveniently presented in divided doses that are administered in equal portions twice-a-day, three times a day, or more than three times a day.

In some embodiments, the desired daily amount of an estrogen receptor modulator of Formula (A), (B), (C) or (D), or a pharmaceutically acceptable salt thereof, that is administered to a patient is administered once a day.

In some embodiments, the daily amount of an estrogen receptor modulator of Formula (A), (B), (C) or (D), or a pharmaceutically acceptable salt thereof, that is administered to a patient is administered twice a day in evenly divided doses.

In some embodiments, the daily amount of an estrogen receptor modulator of Formula (A), (B), (C) or (D), or a pharmaceutically acceptable salt thereof, that is administered to a patient is administered three times a day in evenly divided doses.

In some embodiments, the daily amount of an estrogen receptor modulator of Formula (A), (B), (C) or (D), or a pharmaceutically acceptable salt thereof, that is administered to a patient is administered more than three times a day in evenly divided doses.

In certain embodiments wherein improvement in the status of the breast cancer in the patient is not observed, the daily dose of an estrogen receptor modulator of Formula (A), (B), (C) or (D), or a pharmaceutically acceptable salt thereof, is increased. In some embodiments, a once-a-day dosing schedule is changed to a twice-a-day dosing schedule. In some embodiments, a three times a day dosing schedule is employed to increase the amount of an estrogen receptor modulator, or a pharmaceutically acceptable salt thereof, that is administered.

In some embodiments, an estrogen receptor modulator of Formula (A), (B), (C) or (D), or a pharmaceutically acceptable salt thereof, is administered to a patient in the fasted state. In some embodiments, an estrogen receptor modulator of Formula (A), (B), (C) or (D), or a pharmaceutically acceptable salt thereof, is administered to a patient in the fed state.

In some embodiments, the amount of an estrogen receptor modulator of Formula (A), (B), (C) or (D), or a pharmaceutically acceptable salt thereof, that is given to a patient varies depending upon factors such as, but not limited to, condition and severity of the breast cancer, and the identity (e.g., weight) of the woman.

Figure 10:
FIG. 10 shows [$^{18}$F]FES-PET imaging of a breast cancer patient at baseline, pre-treatment (left) and following one month of continuous oral daily dosing with ERM 1-3 (ARN-810) at 600 mg/day (right) with the image collected at 23 hr post-dose. The patient was confirmed to harbor a soft tissue lesion with ESR1 D538G mutation.
Figure 10:
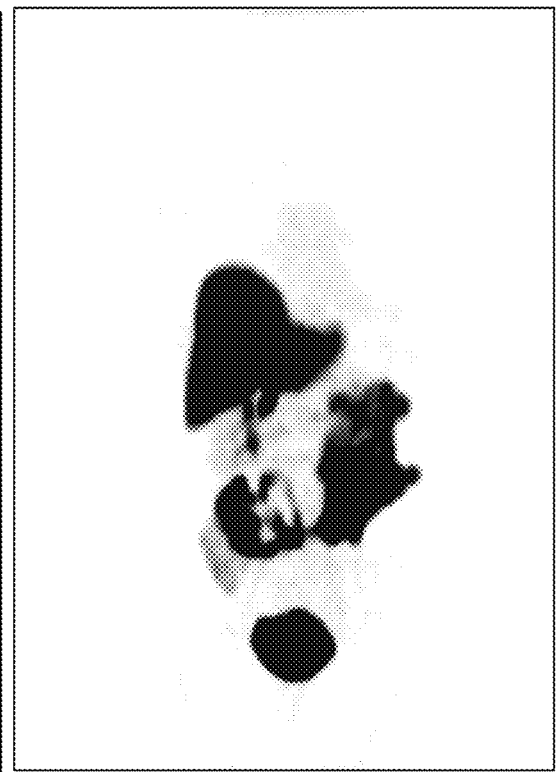

18F-Fluoroestradiol (FES) is a specific and selective radiotracer for the estrogen receptor that can aid clinical drug development by noninvasive monitoring for sufficient target engagement at well-tolerated doses of new therapeutics. Positron emission tomography (PET) with 18F-FES was used to validate estrogen receptor target engagement with ERM 1-3 in a multicenter, Phase I, dose-finding, safety and pharmacokinetic clinical trial in women with advanced or metastatic ER+ breast cancer. FIG. 10 shows [$^{18}$F]FES-PET (fluoroestradiol-positron emission tomography) imaging of a breast cancer patient at baseline, pre-treatment (left) and following one month of continuous oral daily dosing at 600 mg/day of a pharmaceutical formulation ERM 1-3 (ARN-810) (right) with the image collected at 23 hr post-dose. The patient was confirmed to harbor a soft tissue lesion with ESR1 D538G mutation. The patient status is a partial response. FES-PET/CT successfully demonstrates target engagement in clinical trials of ERM 1-3. Other patients in the clinical trial showed similar responses to treatment with the ERM 1-3 pharmaceutical formulation.

Combination Therapies

In some embodiments, the pharmaceutical composition for treatment of a patient having one or more ESR1 mutations further comprises one or more additional therapeutically active agents selected from: corticosteroids, anti-emetic agents, analgesics, anti-cancer agents, anti-inflammatories, kinase inhibitors, receptor inhibitors, antibodies, HSP90 inhibitors, histone deacetylase (HDAC) inhibitors, modulators of the immune system, PD-1 inhibitors, poly ADP-ribose polymerase (PARP) inhibitors, and aromatase inhibitors.

In certain instances, it is appropriate to administer at least one compound of Formula (A), (B), (C) or (D), or a pharmaceutically acceptable salt thereof, in combination with one or more other therapeutic agents. In certain embodiments, the pharmaceutical composition further comprises one or more anti-cancer agents.

In one specific embodiment, a compound of Formula (A), (B), (C) or (D), or a pharmaceutically acceptable salt thereof, is co-administered with a second therapeutic agent, wherein the compound of Formula (A), (B), (C) or (D), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is the additive effect of the two therapeutic agents or the patient may experience a synergistic benefit.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

In some embodiments, methods for treatment of estrogen receptor-dependent or estrogen receptor-mediated conditions or diseases, such as proliferative disorders, including cancer, comprises administration to a mammal a compound of Formula (A), (B), (C) or (D), or a pharmaceutically acceptable salt thereof, in combination with at least one additional therapeutic agent.

In some embodiments, a compound of Formula (A), (B), (C) or (D), or a pharmaceutically acceptable salt thereof, is administered in combination with hormone blocking therapy, chemotherapy, radiation therapy, surgery, a cancer vaccine, a biological therapy, or combinations thereof. In some embodiments, a compound of Formula (A), (B), (C) or (D), or a pharmaceutically acceptable salt thereof, is administered in combination with a peptide, a cytokine, a therapeutic virus, a therapeutic bacterium, gene therapy, siRNA, adoptive T-cell transfer, an antibody, a monoclonal antibody, or combinations thereof.

In some embodiments, a compound of Formula (A), (B), (C) or (D), or a pharmaceutically acceptable salt thereof, is administered in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a compound of Formula (A), (B), (C) or (D), or a pharmaceutically acceptable salt thereof, is administered in combination with an aromatase inhibitor. In some embodiments, the aromatase inhibitor is anastrozole, letrozole or exemestane.

In some embodiments, a compound of Formula (A), (B), (C) or (D), or a pharmaceutically acceptable salt thereof, is administered in combination with a CDK 4/6 inhibitor. In some embodiments, the CDK 4/6 inhibitor is LEE011 or LY283519.

In some embodiments, a compound of Formula (A), (B), (C) or (D), or a pharmaceutically acceptable salt thereof, is administered in combination with a phosphoinositide 3-kinase (PI3K)/mTOR pathway inhibitor. In some embodiments, the phosphoinositide 3-kinase (PI3K)/mTOR pathway inhibitor is everolimus, temsirolimus, BEZ235, BYL719, GDC0032, BKM120, BGT226, GDC0068, GDC-0980, GDC0941, INK128 (MLN0128), INK1117, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Ca1101, PWT33597, CU-906, or CUDC-907.

In some embodiments, a compound of Formula (A), (B), (C) or (D), or a pharmaceutically acceptable salt thereof, is administered in combination with a histone deacetylase inhibitor (HDAC). In some embodiments, the HDAC inhibitor is entinostat or mocetinostat.

In some embodiments, a compound of Formula (A), (B), (C) or (D), or a pharmaceutically acceptable salt thereof, is administered in combination with a HER-2 inhibitor. In some embodiments, the HER-2 inhibitor is trastuzumab, pertuzumab or TDM-1.

In some embodiments, a compound of Formula (A), (B), (C) or (D), or a pharmaceutically acceptable salt thereof, is administered in combination with an epidermal growth factor receptor (EGFR) inhibitor. In some embodiments, the EGFR inhibitor is lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, AP-26113 or CO-1686.

In some embodiments, a compound of Formula (A), (B), (C) or (D), or a pharmaceutically acceptable salt thereof, is administered in combination with an anti-angiogenesis agent. In some embodiments, the anti-angiogenesis agent is a VEGFR inhibitor. In some embodiments, the anti-angiogenesis agent inhibits multiple kinases (e.g., is a multi-kinase targeting agent). In some embodiments, the anti-angiogenesis agent is bevacizumab, ABR-215050 (tasquinimod), CHIR-258 (dovitinib), EXEL-7647, OSI-930, BIBF-1120, BAY-73-4506, BMS-582664 (brivanib), RO-4929097, JNJ-26483327, AZD-2171 (cediranib), sorafenib, aflibercept, enzastaurin, AG-013736 (axitinib), GSK-786034 (pazopanib), AP-23573, or sunitinib In some embodiments, a compound of Formula (A), (B), (C) or (D), or a pharmaceutically acceptable salt thereof, is administered in combination with anti-PD-1 agent. In some embodiments, the anti-PD-1 agent is MK-3475, Nivolumab, MPDL3280A, or MEDI4736.

In some embodiments, a compound of Formula (A), (B), (C) or (D), or a pharmaceutically acceptable salt thereof, is administered in combination with an AKT inhibitor. In some embodiments, the AKT inhibitor is GDC0068, MK-2206, AT7867, GSK2110183, GSK2141795, or GSK690693.

In some embodiments, a compound of Formula (A), (B), (C) or (D), or a pharmaceutically acceptable salt thereof, is administered in combination with doxorubicin, cyclophosphamide, capecitabine, vinorelbine, paclitaxel, docetaxel, or cisplatin.

In some embodiments, an additional therapeutic agent for use in combination with a compound of Formula (A), (B), (C) or (D), or a pharmaceutically acceptable salt thereof, include one or more of the following: abiraterone; abarelix; adriamycin; actinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; GDC0032; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and $I^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

In some embodiments, a compound of Formula (A), (B), (C) or (D), or a pharmaceutically acceptable salt thereof, is used in combination with anti-emetic agents to treat nausea or emesis, which result from the use of a compound of Formula (A), (B), (C) or (D), anti-cancer agent(s) and/or radiation therapy.

In some embodiments, a compound of Formula (A), (B), (C) or (D), or a pharmaceutically acceptable salt thereof, is used in combination with an agent useful in the treatment of anemia or neutropenia.

In some embodiments, a compound of Formula (A), (B), (C) or (D), or a pharmaceutically acceptable salt thereof, is administered with corticosteroids.

In some embodiments, a compound of Formula (A), (B), (C) or (D), or a pharmaceutically acceptable salt thereof, is co-administered with analgesics.

In some embodiments, a compound of Formula (A), (B), (C) or (D), or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix. The term "radiotherapy" or "ionizing radiation" include all forms of radiation, including but not limited to α, β, and γ radiation and ultraviolet light.

In some embodiments, a compound of Formula (A), (B), (C) or (D), or a pharmaceutically acceptable salt thereof, is used in the treatment of breast cancer in combination with at least one additional treatment option for the breast cancer. In some embodiments, the additional treatment option comprises breast cancer surgery. In some embodiments, breast cancer surgery comprises lumpectomy, mastectomy, sentinel node biopsy, or axillary node dissection. In some embodiments, the additional treatment option comprises radiation therapy. In some embodiments, radiation comprises external beam radiation or brachytherapy. In some embodiments, the additional treatment option comprises hormone therapy (i.e. hormone blocking therapy). In some embodiments, hormone therapy comprises the use of a selective estrogen receptor modulator (e.g. tamoxifen), aromatase inhibitor, or fulvestrant. In some embodiments, the additional treatment option comprises surgery to remove the ovaries or medications to stop the ovaries from making estrogen. In some embodiments, the additional treatment option comprises the use of trastuzumab, lapatinib, or bevacizumab. In some embodiments, the additional treatment option comprises the use of bone-building drugs to prevent breast cancer recurrence (e.g. zoledronic acid (Reclast, Zometa)).

Kits/Articles of Manufacture

For use in the diagnostic and therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

In some embodiments, the kits provided herein are for use in detecting nucleic acid encoding a mutant ER-α polypeptide in a subject or for detecting a mutant ER-α polypeptide in a subject (i.e. a diagnostic kit). In some embodiments the kits are employed for selecting patients for treatment with an estrogen receptor modulator compound of Formula (A), (B), (C) or (D), for identifying subjects as resistant or likely to become resistant to hormone therapy, for monitoring the development of resistance to hormone therapy, or combinations thereof. The kits provided herein contain one or more reagents for the detection of the nucleic acid encoding a mutant ER-α polypeptide, for the detection of mutant ER-α polypeptides, for detection of ER activity in cells from the subject, or combinations thereof. Exemplary reagents include but are not limited to, buffers, PCR reagents, antibodies, substrates for enzymatic staining, chromagens or other materials, such as slides, containers, microtiter plates, and optionally, instructions for performing the methods. Those of skill in the art will recognize many other possible containers and plates and reagents that can be used for contacting the various materials. Kits also can contain control samples, such as for example, nucleic acids or proteins, such as for example a mutant ER-α polypeptide provided herein or nucleic acids encoding a mutant ER-α polypeptide provided herein. In some embodiments, kits contain one or more set of oligonucleotide primers for detection of endogenous ER gene expression.

In some embodiments, the container(s) can comprise one or more estrogen receptor modulator compounds of Formula (A), (B), (C) or (D), optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Articles of manufacture, which include packaging material, an estrogen receptor modulator compound of Formula (A), (B), (C) or (D) within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for reducing, diminishing or eliminating the effects of activated estrogen receptors, or for the treatment, prevention or amelioration of one or more symptoms of a disease or condition that would benefit from a reduction or elimination of estrogen receptor activity, are provided.

EXAMPLES

These examples are provided for illustrative purposes only and not to limit the scope of the claims provided herein.

Example 1

MCF-7 3×ERE Luciferase Transcriptional Reporter Assay

In this example, the maximal relative IC50 for inhibition of constitutive transcriptional activity of selected mutant Estrogen Receptors and stimulated wild-type Estrogen Receptor activity was assessed for the ER modulators Estradiol, 4-OH Tamoxifen, Fulvestrant, and a panel of compounds using an 3×ERE-Luciferase reporter in MCF7 breast cancer cells. Under the conditions utilized in this assay, wild-type and all mutant Estrogen Receptors display measurable constitutive, sequence dependent and estradiol independent, basal activity that can be modulated by ER ligands. Therefore, all data presented is relative to the wild-type Estrogen Receptor in the absence of estradiol.

MCF7 cells were maintained in RPMI 1640 supplemented with 10% FCS. Transcriptional assays were performed by seeding 100 µL cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 150 ng 3×ERE-TK-Luc (reporter vector), 30 ng CMVpRL (normalization vector), and 300 ng pCDNA ERα (or ERα mutant). Transfected cells were incubated overnight then treated with ligand. The compounds were serially diluted and 50 µL of compound plus RPMI 1640 supplemented with charcoal stripped serum was added to the cells. Following 24 hour incubation the medium was removed and the cells were lysed in 40 µL of lysis buffer (25 mM Tris Phosphate, 2 mM CDTA, 10% Glycerol, 0.5% Triton X-100, 2 mM DTT). Firefly luciferase activity was measured immediately following the addition of 40 µL luciferase buffer (20 mM tricine, 0.1 mM EDTA, 1.07 mM $(MgCO_3)_4Mg(OH)_2.5H_2O$, 2.67 mM $MgSO_4$, 33.3 mM DTT, 270 µM Coenzyme A, 470 µM luciferin, 530 µM ATP). *Renilla* luciferase was measured following the addition of 40 µL colelenterazine buffer (1.1 M NaCl, 2.2 mM $Na_2EDTA$, 0.22 M $KxPO_4$ (pH 5.1), 0.44 mg/mL BSA, 1.3 mM $NaN_3$, 1.43 µM coelenterazine, final pH adjusted to 5.0). The maximal relative agonist activity of each compound was derived from the point on the dose response curve representing maximum response (bottom of the dose response curves) for each mutant receptor graphed as follows: RLU sample/RLU wtER-α DMSO×100=relative activity. The relative IC50 for each compound is determined as follows: IC50 ER-α mutant/IC50 wt ER-α.

Illustrative transcriptional data for representative compounds disclosed herein is presented in the Table 5:

TABLE 5

| Compound | IC50 (nM) | | | | | |
|---|---|---|---|---|---|---|
| | WT | L536R | Y537C | Y537N | Y537S | D538G |
| 4-OH tamoxifen | ++ | ++ | ++ | ++ | ++ | ++ |
| fulvestrant | +++ | ++ | +++ | +++ | ++ | ++ |
| 1-3 | +++ | ++ | ++ | ++ | + | ++ |
| 1-7 | ++ | ++ | ++ | ++ | + | ++ |
| 1-8 | ++ | ++ | ++ | ++ | + | ++ |
| 1-9 | ++ | ++ | ++ | + | + | + |
| 1-10 | ++ | ++ | ++ | ++ | + | ++ |
| 2-1 | +++ | ++ | ++ | ++ | + | ++ |
| 3-2 | ++ | ++ | ++ | + | + | + |
| 4-1 | +++ | ++ | ++ | ++ | ++ | ++ |
| 4-4 | +++ | +++ | +++ | ++ | ++ | ++ |
| 4-7 | ++ | ++ | ++ | ++ | ++ | ++ |
| 4-10 | ++ | ++ | ++ | ++ | + | + |
| 4-14 | ++ | ++ | ++ | ++ | + | ++ |
| 4-17 | ++ | ++ | ++ | ++ | + | ++ |
| 4-20 | ++ | ++ | ++ | ++ | + | ++ |
| 4-23 | ++ | ++ | ++ | ++ | ++ | ++ |
| 4-25 | ++ | + | ++ | + | + | + |
| 4-28 | ++ | + | ++ | + | + | + |
| 4-31 | ++ | ++ | ++ | ++ | ++ | ++ |
| 4-34 | ++ | ++ | ++ | ++ | ++ | ++ |
| 4-37 | ++ | + | + | + | + | + |
| 4-40 | + | + | + | + | + | + |
| 4-44 | ++ | ++ | ++ | ++ | + | ++ |

:'+': >10 nM; '++': 1-10 nM; '+++': <1 nM

Example 2

Clinical Trial of ERM Compound 1-3 in Postmenopausal Women with Locally Advanced or Metastatic ER+ Breast Cancer and Locally Confirmed ESR1 Mutation This is an open label clinical trial evaluating the efficacy and safety of ERM Compound 1-3, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in post-menopausal women with locally advanced or metastatic ER+ (HER2−) breast cancer who have a confirmed ESR1 mutation.

Objectives: To evaluate the pharmacokinetics (PK), safety and tolerability and assess preliminary evidence of antitumor activity of ERM Compound 1-3, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in post-menopausal women with locally advanced or metastatic ER+ (HER2−) breast cancer and a confirmed ESR1 mutation. Additional objectives include: perform exploratory evaluation of biomarkers of pharmacodynamic (PD) response with [$^{18}$F]-fluoroestradiol (FES) positron emitting tomography (PET) [FES PET]; perform exploratory evaluation of ER target genes expression; perform exploratory evaluation of mechanisms of resistance to (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, following single and multiple dose treatments (e.g. $C_{max}, T_{max}$, AUC, $T_{1/2}$).

Trial Design: Women in this study will be given the recommended phase 2 dose of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, or assigned to escalating doses of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, with a starting dose of about 400 mg per day of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, followed by dose escalation by approximately 200 mg increments thereafter. Patients should have measurable disease progression following prior treatment with an aromatase inhibitor, and confirmed ESR1 mutation(s).

All patients will be treated until disease progression, unacceptable toxicity, or patient withdrawal of consent.
Patient Selection
Inclusion Criteria:
1. Histologically or cytologically proven diagnosis of adenocarcinoma of the breast with evidence of either locally recurrent disease not amenable to resection or radiation therapy with curative intent, or metastatic disease, both progressing after at least 6 months of hormonal therapy for ER+ breast cancer 2. ER-positive tumor (staining in ≥1% cells by immunohistochemistry [IHC] as per laboratory testing)

3. HER2-negative breast cancer as per local laboratory testing (IHC result of 0 or +1 for cellular membrane protein expression or a FISH result showing HER2/CEP17 ratio <1.8 or an average of fewer than 4 copies of HER2 gene per nucleus for systems without an internal control probe)

4. Evaluable disease as per RECIST v1.1 further defined as follows:

Measurable disease, or evaluable bone disease, i.e., bone lesions that are lytic or mixed (lytic+sclerotic) in the absence of measurable lesion. Note: previously irradiated lesions are deemed measurable only if progression is documented at the site after completion of radiation. Patients with non-measurable, non-evaluable lesion (such as pleural effusion) would not be eligible for the dose expansion portion of the trial 5. ESR1 mutations as per laboratory testing. Disease progression following treatment with an aromatase inhibitor.

6. At least 2 months must have elapsed from the use of tamoxifen

7. At least 2 weeks must have elapsed from the use of any other anti-cancer hormonal therapy 8. At least 3 weeks must have elapsed from the use of any chemotherapy 9. Females, 18 years of age or older 10. Postmenopausal status defined as:

Prior bilateral surgical oophorectomy

Age ≥56 years: natural amenorrhea with ≥1 year since last menses

Age <56 years with amenorrhea ≥1 year since last menses and serum estradiol levels (<20 pg/mL) and FSH levels (>40 mIU/mL) in the postmenopausal range Age <56 years who had hysterectomy with one or both ovaries left in place, or with tamoxifen-induced amenorrhea together with a tamoxifen discontinuation of ≥1 year and serum estradiol levels (<20 pg/mL) and FSH levels (>40 mIU/mL) in the postmenopausal range 11. Eastern Cooperative Oncology Group (ECOG) Performance status <2 (for Cohort A) or ≤1 (for Cohorts B1 and B2)

12. Resolution of all acute toxic effects of prior therapy or surgical procedures to baseline or Grade ≤1 (except alopecia or other toxicities not considered to be a safety risk for the patient)

13. Adequate organ function as defined by the following criteria:

Absolute neutrophil count (ANC)≥1500/μL

Platelets≥100,000/μL

Serum aspartate transaminase (AST) and serum alanine transaminase (ALT)≤3× upper limit of normal (ULN), or AST and ALT ≤5×ULN if liver function abnormalities are due to underlying malignancy Total serum bilirubin ≤1.5×ULN regardless of liver involvement secondary to tumor. Inclusion of patients with increased serum indirect bilirubin (≤3×ULN) due to Gilbert's syndrome is permitted Serum creatinine≤1.5×ULN QTc≤460 msec 14. Signed and dated informed consent document indicating that the subject (or legally acceptable representative) has been informed of all the pertinent aspects of the trial prior to enrollment 15. Willingness and ability to comply with scheduled visits, treatment plan, laboratory tests, and other trial procedures Exclusion Criteria:

1. Untreated or symptomatic CNS metastases. Note: Patients with treated and asymptomatic CNS metastases that are radiographically stable within 12 weeks prior to enrollment will be allowed, provided long-term use of corticosteroids have been discontinued within 4 weeks prior to enrollment 2. Endometrial disorders 3. More than 1 prior chemotherapy in the advanced/metastatic setting.

4. Current treatment with any systemic anti-cancer therapies for advanced disease or any systemic experimental treatment on another clinical trial 5. Diagnosis of any secondary malignancy within 2 years prior to enrollment, except for adequately treated basal cell or squamous cell skin cancer, or carcinoma in situ 6. Any of the following within 12 months prior to enrollment: myocardial infarction, severe/unstable angina, ongoing cardiac dysrhythmias of Grade ≥2, atrial fibrillation of any grade, coronary/peripheral artery bypass graft, symptomatic congestive heart failure, or cerebrovascular accident including transient ischemic attack 7. Active inflammatory bowel disease or chronic diarrhea, short bowel syndrome, or upper gastrointestinal surgery including gastric resection 8. Known human immunodeficiency virus infection 9. Major surgery or radiation therapy within 4 weeks prior to enrollment 10. Other severe acute or chronic medical or psychiatric condition or laboratory abnormality that may increase the risk associated with study participation or investigational product administration or may interfere with the interpretation of study results and, in the judgment of the Investigator, would make the subject inappropriate for entry into this study Tumor Assessments: Disease assessments will be performed. Imaging studies will include a CT scan of the chest, abdomen, and pelvis, plus a bone scan. Radiographic confirmation of objective tumor response or disease progression will be based on RECIST v1.1 (Eisenhauer, 2009). For new bone lesions detected on bone scans, a second imaging modality (e.g., CT or MRI) will be required to confirm progression.

The same method of assessment and the same technique should be used at Screening and during follow up. Intravenous (IV) contrast is required when not medically contraindicated. Patients who have a contraindication to IV contrast may have MRI exams of the abdomen and pelvis performed in lieu of CTs and a non-contrast CT of the chest. Tumor evaluation by positron emission tomography (PET) scan or by ultrasound may not substitute for CT.

Correlative Studies

Pharmacodynamics with $^{18}$FES-PET Target Engagement: Imaging with [18F]-fluoroestradiol (FES) positron emitting tomography (PET) will be performed to quantify ER expression in the tumor and to assess for pharmacodynamic response to therapy with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof. While FES uptake can vary between patients, in general, the FES uptake is fairly consistent across lesions at a given time point, and the average uptake provides a reasonable summary of ER expression for an individual patient. Factors that can affect the standardized uptake value (SUV), such as sex hormone-binding globulin (SHBG), will be adjusted as per standard protocol (Peterson, 2011). In addition, a washout period for patients previously treated with tamoxifen (at least 2 months) or fulvestrant (at least 6 months) may be required due to the long half-life of each drug and their potential to interfere with FES uptake. FES-PET studies will be performed as hybrid PET/CT imaging for attenuation correction and lesion localization.

Core Biopsies: Pre- and post-treatment tumor biopsies (soft tissue or visceral lesions) will be collected to evaluate:
Tumor Histology; tumor vs. stroma, vs fibrotic tissue
ERα and PR protein levels by immunohistochemistry or immunofluorescence
Proliferative Index (Ki67)
ER target gene modulation Examples of ER target genes that may be monitored include, but are not limited to: AGR2, AREG, C3, CCND1, CXCL12, ERBB2, GREB1, IL6, IRS1, PDZK1, PGR, SEMA3B, TFF1, TFF2, TFF3, TOP2A, WISP2.

Circulating Tumor DNA (ctDNA): In all patients during dose escalation and dose expansion, additional blood samples will be collected at Screening, on treatment and at the time of study discontinuation for analysis of circulating tumor DNA (ctDNA).

Recent preclinical and clinical data suggest that mutations in ER-α and phosphatidylinositol-4,5-bisphosphate 3-kinase, catalytic subunit alpha (PIK3CA) are associated with endocrine resistant breast cancer. To gain insights into potential causal relationships between the clinical activity of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, and resistance mechanisms, mutational status of both of these genes will be monitored in ctDNA isolated from plasma using advanced DNA analysis techniques such as the sensitive, emulsion PCR-based BEAMing (Beads, Emulsions, Amplification, and Magnetics) method (Dressman, 2003) or next generation sequencing.

Example 3

Activity of ERM Compound 1-3 (ARN-810) on Clinically Relevant ESR1 Mutations

The purpose of this study was to assess the efficacy of ERM 1-3, (E)-3-(4-((E)-2-(2-chloro-4-fluorophenyl)-1-(1H-indazol-5-yl)but-1-en-1-yl)phenyl)acrylic acid from Table 1 on clinically relevant estrogen receptor mutations that are proposed to confer resistance to anti-hormonal therapies such as aromatase inhibitors. Potency and efficacy of ERM 1-3 were measured in vitro in ER dependent transcriptional reporter assays and viability assays of MCF-7 cells stably expressing ER-α mutants. ERM 1-3 activity was compared to the clinically relevant ER-α targeting breast cancer therapeutics 4-hydroxytamoxifen (an active metabolite of tamoxifen) and fulvestrant. In cell-based transcriptional reporter assays, ERM 1-3 inhibited the activity of all the ER-α mutations (E380Q, L536R, L536P, Y537C, Y537N, Y537S and D538G) tested with nanomolar potency, and efficacy approached or was greater than that observed with the wild-type receptor. In MCF-7 cells stably expressing ER-α mutants, ERM 1-3 reduced the number of viable cells by 44%-78% (compared to DMSO control in 5 day proliferation assays), depending on the mutation and assay format. In both reporter and proliferation assays, ERM 1-3 displayed 0.8 to 210-fold reduced potency across the panel of ESR1 mutations compared to wild-type ER-α. However, in contrast to the transcriptional reporter assays, in the viability assays ERM 1-3 generally displayed reduced efficacy compared to cells stably expressing wild-type ER-α.

Compounds and Formulations:

ERM 1-3 was prepared as described in WO 2012/037410, Example 36 and WO 2012/037411, Example 50. The drug substance samples had >95% purity (Purity assessment: nuclear magnetic resonance/liquid chromatography-mass spectrometry) and were off-white powders. The sodium or N-methyl-D-glucamine salt form of the molecule was utilized. ARN-810 was supplied as a 10 mM stock solution dissolved in DMSO that was stored at −20° C.

Fulvestrant (neutral form) was purchased from Waterstone Technology (WS10032) and re-suspended in anhydrous DMSO at a final concentration of 10 mM, then dispensed in aliquots and stored at −80° C.

4-Hydroxytamoxifen was purchased from Sigma Aldrich, was re-suspended in anhydrous DMSO at a final concentration of 10 mM, then dispensed in aliquots and stored at −80° C.

MCF-7 cells can be obtained from ATCC (ATCC® HTB-22™). The cells were expanded and stored in liquid nitrogen after one passage in culture. A vial of frozen cells were thawed and put into culture every two months, and then split twice weekly. Thawed cells were in culture for two weeks to allow for recovery from the freezing process prior to use in any assay. The cells used in the assays detailed in this report have undergone between 5 and 22 passages from initial thaw.

Cell Culture Growth Media
Corning™ Cellgro™ RPMI 1640 (Corning, Catalog No. 15-040)
Corning™ Cellgro™ RPMI 1640 without Phenol Red (Corning, Catalog No. 17-105)
Thermo Scientific™ HyClone™ Fetal Bovine Serum (U.S.), Characterized—(FBS) (Thermo Scientific Catalog No. SH3007103)
Thermo Scientific™ HyClone™ Fetal Bovine Serum (U.S.), Charcoal/Dextran Treated—(Thermo Scientific, Catalog No. SH3006803)
Other Reagents
CellTiter-Glo® Reagent (Promega, Catalog No. G7572)
Assay Plate, 384 Well, With Lid, Flat Bottom, Low Flange, Tissue Culture Treated, Sterile, White Polystyrene. (Corning, Catalog No. 3570)
Dimethyl Sulfoxide, anhydrous (Sigma Aldrich, Catalog No. 276855-100 mL)
Matrix 12 channel electronic pipettes, 0.5-12.5 µL, 2-125 µL, and Matrix 8 channel electronic pipette, 15-1250 µL
96-well TC-treated sterile polystyrene plates (Corning Inc., Catalog Nos. 3903, 3904 or 3917)
Lipofectin (Invitrogen, Catalog No. 18292037)
D-Luciferin, Potassium Salt (Gold Biotechnology, Catalog No. LUCK-500)
Perkin Elmer EnVision 2103™ Multilabel Reader
Molecular Devices Analyst™ GT Multimode Reader
Reichert BrightLine® Improved Neubauer Hemacytometer (Hausser Scientific, Catalog No. 1490)
Statistical Analysis: Curve Fits and $IC_{50}$ and $E_{max}$ values were generated with GraphPad Prism® Software using a log (inhibitor) vs. response variable slope (four parameters) curve fit, using GraphPad Prism Version 6.01 and Microsoft Office Excel (2010)

Example 4

ER-α Transcriptional Reporter Assay

MCF-7 cells were maintained in RPMI 1640 supplemented with 10% FCS. Transcriptional assays were performed by seeding 100 µL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 180 ng 3×ERE-TK-Luc (reporter vector), 30 ng pRL-CMV (normalization vector), and 270 ng pCDNA ER-α (or ER-α mutation). Transfected cells were incubated overnight then treated with ligand. For ER agonist assays, the compounds were serially diluted and 50 µL of compound plus RPMI 1640 supplemented with charcoal stripped serum was added to the cells.

For ER antagonist assays, the compounds were serially diluted and 50 µL of compound plus 3 nM 17β-estradiol in RPMI 1640 supplemented with charcoal stripped serum was added to the cells. Following 24 hour incubation the medium was removed and the cells were lysed in 40 µL of lysis buffer (25 mM Tris Phosphate, 2 mM CDTA, 10% Glycerol, 0.5% Triton X-100, 2 mM DTT).

Firefly luciferase activity was measured immediately following the addition of 40 µL luciferase buffer (20 mM tricine, 0.1 mM EDTA, 1.07 mM $(MgCO_3)_4$ $Mg(OH)_2.5H_2O$, 2.67 mM $MgSO_4$, 33.3 mM DTT, 270 µM Coenzyme A, 470 µM luciferin, 530 µM ATP). Renilla luciferase was measured following the addition of 40 µL coelenterazine buffer (1.1 M NaCl, 2.2 mM $Na_2EDTA$, 0.22 M $KxPO_4$ (pH 5.1), 0.44 mg/mL BSA, 1.3 mM $NaN_3$, 1.43 µM coelenterazine, final pH adjusted to 5.0). The maximal relative agonist activity of each compound was derived from the bottom of the dose response curves for each mutant receptor graphed as follows: RLU sample/RLU wt ER-α DMSO=relative activity.

MCF-7 Mutant ER-α Stable Cell Line Generation: MCF-7 cells stably expressing wild-type or ER-α mutants were generated by subcloning ESR1 wild-type and mutant cDNAs containing an amino terminal hemagglutinin tag into pCDH-EF1-MCS-(PGK-Puro) (referred to as EF1 HA-ER-α) and pCDH-UbC-MCS-EF1-Hygro (referred to as UbC HA-ER-α) (System Biosciences). The resulting plasmids, in addition to an empty vector negative control, were subsequently cotransfected into HEK293T cells with the pPACKH1 packaging plasmid mix (System Biosciences) according to the manufacturer's protocol. Four days post transfection lentiviral particles were purified from the cell medium, tiered and stored at −80° C. MCF-7 cells were transduced with the purified viral particles and stable cell lines were selected by growth in RPMI containing 10% FBS plus 1 µG/mL puromycin or 200 µG/mL hygromycin for pCDH-EF1-MCS-(PGK-Puro) and pCDH-UbC-MCS-EF1-Hygro, respectively. Following selection, expression of wild-type and mutant ER-α was confirmed by western blot using the 6E2 mouse monoclonal HA antibody (Cell Signaling).

MCF-7 Stable Cell Line Viability: MCF-7 cells were enumerated with a hemacytometer adjusted to a concentration of 40,000 cells per mL in Phenol Free RPMI containing 10% CSS with NEAA and Sodium Pyruvate. 16 microliters of the cell suspension was added to each well of a 384 well tissue culture treated white clear bottom polystyrene plate (Corning) using a Matrix 16 channel electronic pipette. The cells were incubated overnight to allow the cells to adhere. The following day, 16 microliters of Phenol Free RPMI containing 10% CSS with NEAA and Sodium Pyruvate was added to the wells of one plate, followed by 16 µL of CellTiter-Glo (Promega, Madison Wis.) luminescent cell viability reagent using a Matrix 16 channel electronic pipette. Following a 20 minute incubation at room temperature, luminescence was measured on a Perkin Elmer Envision 2103 Multilabel Reader with the luminescence measurement height set at 6.5 mm and a maximum integration time of 1 second. The "average" of the relative luminescence units (RLUs) of the wells are considered to be the baseline value at time=zero. In addition, a 10 point, 1:5 serial dilution in DMSO (Sigma-Aldrich) was performed using Matrix 12 channel electronic pipette, including DMSO only as positive control. 4 µL of each dilution was then added to 196 µL of RPMI containing 10% CSS with NEAA and Sodium Pyruvate. 16 µL of medium containing compound was added to the cells at a final concentration ranging from 10 µM to 5 pM. Compound dilution in media and subsequent addition to cells were carried out using Matrix 12 channel electronic pipettes. After 5 day compound exposure, 16 µL of CellTiter-Glo (Promega, Madison Wis.) luminescent cell viability reagent was added to the cells using a Matrix 16 channel electronic pipette. CellTiter-Glo added to 32 µL of medium without cells was used to obtain a background value. Luminescence was measured on a Perkin Elmer Envision 2103 Multilabel Reader with the luminescence measurement height set at 0 mm and a maximum integration time of 0.1 second. The relative luminescence units (RLUs) of each well were measured, and relative proliferation (fold) of each sample was determined as follows: (RLU sample−RLU background)/(RLU at T=0)=relative proliferation Example 5

Compound 1-3 (ARN-810) and ER Transcriptional Reporter Assays

Compound 1-3 (ARN-810), 4-hydroxytamoxifen and fulvestrant effects on the transcriptional activity of clinically relevant ESR1 mutations (E380Q, L536R, L536P, Y537C, Y537N, Y537S and D538G) were evaluated in MCF-7 breast cancer cells transiently expressing wild-type ER-α or ER-α mutants. MCF-7 cells were transiently transfected with an ER responsive transcriptional reporter plus wild-type or mutant ER-α expression plasmids, and treated with ARN-810, 4-hydroxytamoxifen or fulvestrant ranging from 0.1 pM to 10 µM or 17β-estradiol ranging from 0.1 pM to 1 µM. To assess potential agonist activity of the compounds, the cells were treated in the absence of estradiol. Antagonist assays were run in the presence of 1 nM estradiol. As seen in Table 6, in the absence of estradiol, all of the clinical mutations analyzed demonstrate detectable ligand-independent activity that is inhibited to levels approaching wild-type by ARN-810, 4-hydroxytamoxifen and fulvestrant. All antagonists retain nanomolar potency on the mutations tested (Table 7). However, with few exceptions (4-hydroxytamoxifen activity on E380Q and L536P), in agonist mode, all antagonists demonstrate a modest reduction (1.1 to 61 fold) in potency on the mutant receptors in comparison to wild-type ER-α, with a maximum of 61 fold observed for ARN-810 on the Y537S mutation. Similar effects on efficacy were observed when a subset of the ESR1 mutations (L536R, Y537C, Y537N, Y537S and D538G) was analyzed in antagonist mode transcriptional assays. However, in the presence of estradiol the potency shift observed with ARN-810 was less pronounced. Specifically, on the clinically relevant mutations ARN-810 $IC_{50}$ was changed 0.8 to 1.7 fold and the maximal efficacy approached that observed on the wild-type receptor (Tables 8 and 9).

TABLE 6

ARN-810 Inhibits Transcriptional Activity of Clinically Relevant ER-α Mutations (Agonist Mode, −E2)

| | | | Efficacy ($E_{max}$) | | | |
|---|---|---|---|---|---|---|
| Receptor | n | Vehicle | 17β-Estradiol | 4-Hydroxytamoxifen | Fulvestrant | ARN-810 |
| Wild-type | 7 | 1.00 | 3.08 ± 1.21 | 0.24 ± 0.10 (76%) | 0.15 ± 0.09 (85%) | 0.14 ± 0.09 (86%) |
| E380Q | 1 | 2.15 | 3.20 | 0.53 (75%) | 0.38 (82%) | 0.36 (83%) |
| L536R | 7 | 1.47 ± 0.51 | 2.64 ± 0.64 | 0.33 ± 0.13 (78%) | 0.32 ± 0.12 (78%) | 0.29 ± 0.12 (80%) |
| L536P | 1 | 3.12 | 4.95 | 0.44 (86%) | 0.42 (87%) | 0.38 (88%) |
| Y537C | 7 | 3.2 ± 0.32 | 2.94 ± 2.12 | 0.42 ± 0.11 (87%) | 0.28 ± 0.10 (91%) | 0.31 ± 0.15 (90%) |
| Y537N | 7 | 4.06 ± 1.39 | 3.70 ± 1.54 | 0.38 ± 0.14 (91%) | 0.30 ± 0.18 (93%) | 0.37 ± 0.17 (91%) |
| Y537S | 7 | 7.54 ± 1.95 | 1.95 ± 2.01 | 0.41 ± 0.27 (95%) | 0.34 ± 0.13 (96%) | 0.24 ± 0.54 (97%) |
| D538G | 7 | 4.31 ± 1.22 | 2.82 ± 2.32 | 0.27 ± 0.20 (94%) | 0.24 ± 0.14 (94%) | 0.28 ± 0.20 (94%) |

$E_{max}$ is the maximal stimulated activity relative to vehicle treated wild-type ER-α.
Percent inhibition compared to vehicle is also presented (%).
Data is the average and standard deviation derived from n independent experiments.

TABLE 7

ARN-810 is a Transcriptional Antagonist of Clinically Relevant ER-α Mutations (Agonist Mode, −E2)

| | | Potency ($EC_{50}$; nM) | | | |
|---|---|---|---|---|---|
| Receptor | n | 17β-Estradiol | 4-Hydroxytamoxifen | Fulvestrant | ARN-810 |
| Wild-type | 7 | 0.13 ± 0.09 | 2.16 ± 3.44 | 0.38 ± 0.47 | 0.84 ± 0.61 |
| E380Q | 1 | 0.33 | 0.49 | 0.72 | 3.92 |
| L536R | 7 | 0.62 ± 1.07 | 4.06 ± 4.32 | 1.72 ± 1.39 | 2.91 ± 1.58 |
| L536P | 1 | 0.24 | 0.48 | 1.20 | 8.47 |
| Y537C | 7 | >100 | 2.99 ± 3.45 | 0.55 ± 0.38 | 4.31 ± 3.05 |
| Y537N | 7 | 20.23 ± 40.95 | 3.15 ± 2.76 | 0.60 ± 0.47 | 6.21 ± 3.83 |
| Y537S | 7 | >100 | 5.81 ± 2.95 | 2.00 ± 1.07 | 51.25 ± 62.26 |
| D538G | 7 | >100 | 3.10 ± 2.38 | 2.07 ± 1.40 | 6.90 ± 4.57 |

Data is the average and standard deviation derived from n independent experiments.

TABLE 8

ARN-810 Antagonizes Transcriptional Activity of Clinically Relevant ER-α Mutations (Antagonist Mode, +E2)

| | | | Efficacy ($E_{max}$) | | | |
|---|---|---|---|---|---|---|
| Receptor | n | Vehicle | 17β-Estradiol | 4-Hydroxytamoxifen | Fulvestrant | ARN-810 |
| Wild-type | 3 | 2.25 ± 0.55 | 1.10 ± 1.17 | 0.04 ± 0.07 (98%) | 0.06 ± 0.08 (97%) | 0.72 ± 0.42 (68%) |
| L536R | 3 | 2.61 ± 0.96 | 1.60 ± 1.43 | 0.26 ± 0.08 (90%) | 0.30 ± 0.11 (89%) | 0.18 ± 0.14 (93%) |
| Y537C | 3 | 3.13 ± 0.76 | 0.52 ± 0.91 | 0.31 ± 0.22 (90%) | 0.16 ± 0.12 (95%) | 0.39 ± 0.26 (88%) |
| Y537N | 3 | 3.94 ± 2.24 | 1.56 ± 1.27 | 0.31 ± 0.32 (92%) | 0.20 ± 0.20 (95%) | 0.26 ± 0.34 (93%) |
| Y537S | 3 | 5.79 ± 1.85 | 1.35 ± 1.37 | 0.22 ± 0.23 (96%) | 0.37 ± 0.30 (94%) | 0.01 ± 0.02 (100%) |
| D538G | 3 | 5.31 ± 1.88 | 0.86 ± 1.50 | 0.12 ± 0.22 (98%) | 0.10 ± 0.17 (98%) | 0.03 ± 0.05 (99%) |

$E_{max}$ is the maximal stimulated activity relative to vehicle treated wild-type ER-α.
Percent inhibition compared to vehicle is also presented (%).
Data is the average and standard deviation derived from n independent experiments.

TABLE 9

ARN-810 is a Transcriptional Antagonist of Clinically Relevant ER-α Mutations (Antagonist Mode, +E2)

| | | Potency ($EC_{50}$; nM) | | | |
|---|---|---|---|---|---|
| Receptor | n | 17β-Estradiol | 4-Hydroxytamoxifen | Fulvestrant | ARN-810 |
| Wild-type | 3 | 1.10 ± 1.17 | 9.04 ± 7.59 | 1.51 ± 0.70 | 32.91 ± 37.88 |
| L536R | 3 | 1.60 ± 1.43 | 13.87 ± 3.68 | 13.4 ± 9.95 | 35.55 ± 26.84 |
| Y537C | 3 | 0.52 ± 0.91 | 9.92 ± 1.35 | 2.16 ± 093 | 29.91 ± 38.89 |

TABLE 9-continued

ARN-810 is a Transcriptional Antagonist of Clinically Relevant ER-α Mutations (Antagonist Mode, +E2)

| Receptor | n | Potency (EC$_{50}$; nM) | | | |
|---|---|---|---|---|---|
| | | 17β-Estradiol | 4-Hydroxytamoxifen | Fulvestrant | ARN-810 |
| Y537N | 3 | 1.56 ± 1.27 | 4.55 ± 2.90 | 2.90 ± 2.56 | 36.76 ± 54.81 |
| Y537S | 3 | 1.35 ± 1.37 | 102.69 ± 151.87 | 5.30 ± 2.14 | 27.26 ± 6.05 |
| D538G | 3 | 0.86 ± 1.50 | 9.26 ± 1.58 | 4.64 ± 2.44 | 57.57 ± 76.26 |

Data is the average and standard deviation derived from n independent experiments.

Viability Assays: To assess the ability of ARN-810 to antagonize the ligand-independent proliferative activity of the constitutively active ER-α mutations identified in patients, MCF-7 cell lines that stably express wild-type, E380Q, L536P, L536R, Y537N, Y537S, Y537C and D538G amino-terminal hemagglutinin-tagged ER-α (HA-ER-α) were generated. Because ER-α overexpression can induce ligand-independent growth and also can saturate the ligand mediated degradation pathway independent stable cell lines were created for each receptor utilizing the UbC and EF1 promoter to drive ER-α expression (Li S, et al. Cell Rep (2013); 4(6): 1116-1130; Wardell S E, et al. Biochem Pharmacol (2011); 82(2): 122-130). The UbC promoter is reported by the manufacturer (System Biosciences) to express low to moderate RNA levels while the EF1 promoter expresses high levels (System Biosciences). As determined by quantitative Western blot analysis, the UbC based cell lines express HA-ER-α protein at levels less than 10% of endogenous ER-α. On the other hand, the EF1 promoter based lines express HA-ER-α and the mutants at 2- to 6-fold higher levels than the endogenous protein.

Consistent with their activity in the transcriptional reporter assay, expression of the clinically identified ER-α mutants in MCF-7 cells by either the UbC or EF1 promoter conferred the ability of the cells to proliferate in the absence of 17β-estradiol (Tables 10 and 14). However, the high level of wild-type ER-α expression (approximately 2-3 fold more than endogenous protein levels) attained using the EF1 promoter was also sufficient to promote ligand independent growth.

In the UbC promoter based cell lines, compound 1-3 (ARN-810), 4-hydroxytamoxifen and fulvestrant antagonized proliferation of cell lines stably expressing wild-type, E380Q, L536P, L536R, Y537N, Y537S, Y537C and D538G HA-ER-α in both agonist and antagonist modes (Tables 10 and 12). The fulvestrant and ARN-810 demonstrate similar efficacy (ranging from 47% to 67% and 71% to 78% inhibition for the agonist and antagonist mode, respectively) while 4-hydroxytamoxifen displayed reduced efficacy on all the mutations tested. In agonist and antagonist mode all three antagonists displayed high picomolar to low nanomolar IC$_{50}$ against the UbC HA-ER-α mutant cell lines (Tables 11 and 13). In agonist mode, the UbC wild-type HA-ER-α cell line did not proliferate sufficiently to derive an accurate IC$_{50}$, however, in antagonist mode all antagonists display a modest reduction in potency compared to wild-type ER-α (1.3- to 5.4-fold, Table 13).

In the EF1-derived lines, in agonist mode all antagonists demonstrate reduced potency on the mutant receptors compared to wild-type (8- to 140-fold, 2- to 47-fold and 2- to 210-fold for 4-hydroxytamoxifen, fulvestrant and ARN-810, respectively). Additionally, ARN-810 displayed reduced efficacy on the Y537 mutants compared to both fulvestrant and 4-hydroxytamoxifen (Tables 15 and 16). Similar observations of antagonist efficacy and potency were observed when the proliferation assays were performed in antagonist mode (Tables 16 and 17). However, in the presence of 17β-estradiol, the difference in antagonist potency between the wild-type and the mutant HA-ER-α bearing cell lines was less pronounced than observed in the EF-1 agonist assay (15-fold maximum).

TABLE 10

ARN-810 Reduces Viable Cell Number of MCF-7 Cells Stably Expressing Clinically Relevant ER-α Mutants after 5-Day Incubation (UbC HA-ER-α; Agonist Mode; −E2)

| Receptor | Efficacy (E$_{max}$) | | | | |
|---|---|---|---|---|---|
| | Vehicle | 17β-Estradiol | 4-Hydroxytamoxifen | Fulvestrant | ARN-810 |
| None[1] | 1.76 ± 0.26 | 4.12 ± 0.88 | 1.42 ± 0.43 (19%) | 1.27 ± 0.24 (28%) | 1.23 ± 0.88 (30%) |
| Wild-type | 1.85 ± 0.46 | 4.43 ± 0.88 | 1.58 ± 0.16 (14%) | 1.17 ± 0.13 (37%) | 1.17 ± 0.17 (37%) |
| E380Q | 4.27 ± 0.87 | 7.36 ± 1.07 | 2.40 ± 0.39 (44%) | 1.70 ± 0.30 (60%) | 1.74 ± 0.24 (59%) |
| L536P | 3.16 ± 0.36 | 5.06 ± 0.76 | 2.06 ± 0.19 (35%) | 1.66 ± 0.11 (47%) | 1.58 ± 0.16 (50%) |
| L536R | 3.82 ± 0.78 | 5.72 ± 0.74 | 2.26 ± 0.36 (41%) | 1.71 ± 0.22 (55%) | 1.73 ± 0.22 (55%) |
| Y537N | 4.31 ± 0.83 | 5.67 ± 1.06 | 2.34 ± 0.29 46%) | 1.61 ± 0.15 (63%) | 1.67 ± 0.15 (61%) |
| Y537S | 5.16 ± 0.60 | 6.57 ± 0.89 | 2.76 ± 0.03 (47%) | 1.88 ± 0.13 (64%) | 1.91 ± 0.13 (63%) |
| Y537C | 4.88 ± 0.17 | 6.72 ± 0.46 | 2.63 ± 0.19 (46%) | 1.77 ± 0.11 (64%) | 1.86 ± 0.11 (62%) |
| D538G | 5.64 ± 1.35 | 7.21 ± 1.69 | 2.71 ± 0.43 (52%) | 1.91 ± 0.28 (66%) | 1.84 ± 0.25 (67%) |

MCF-7 cells were used as the negative control.
E$_{max}$ is the maximal stimulated proliferative response at Day 5 relative to Day 0.
Percent inhibition compared to vehicle is also presented (%).
Data is the average and standard deviation derived from 4 independent experiments.

TABLE 11

ARN-810 Is a Potent Proliferative Antagonist of MCF-7 Cells Stably
Expressing Clinically Relevant ER-α Mutants (UbC HA-ER-α; Agonist Mode; −E2)

| Receptor | Potency ($EC_{50}$; nM) | | | |
|---|---|---|---|---|
| | 17β-Estradiol | 4-Hydroxytamoxifen | Fulvestrant | ARN-810 |
| None[1] | 0.279 ± 0.518 | 262.7 ± 524.8 | 0.050 ± 0.017 | 0.603 ± 0.740 |
| Wild-type | 0.101 ± 0.160 | 0.626 ± 0.528 | 0.080 ± 0.042 | 0.580 ± 0.386 |
| E380Q | 0.013 ± 0.011 | 1.594 ± 0.681 | 0.248 ± 0.094 | 1.298 ± 0.232 |
| L536P | 0.212 ± 0.401 | 0.821 ± 0.726 | 0.298 ± 0.132 | 0.713 ± 0.487 |
| L536R | 0.008 ± 0.006 | 1.056 ± 0.714 | 0.257 ± 0.090 | 0.926 ± 0.428 |
| Y537N | 0.126 ± 0.233 | 1.585 ± 0.955 | 0.355 ± 0.163 | 2.223 ± 0.550 |
| Y537S | 0.010 ± 0.006 | 14.57 ± 10.95 | 1.057 ± 0.263 | 12.874 ± 4.681 |
| Y537C | 0.019 ± 0.010 | 1.475 ± 0.278 | 0.388 ± 0.106 | 1.728 ± 0.409 |
| D538G | 0.022 ± 0.015 | 3.446 ± 0.821 | 0.999 ± 0.358 | 4.062 ± 0.794 |

MCF-7 cells were used as the negative control.
Data is the average and standard deviation derived from 4 independent experiments.

TABLE 12

ARN-810 Reduces Viable Cell Number of MCF-7 Cells Stably Expressing
Clinically Relevant ER-α Mutants after 5-Day Incubation (UbC HA-ER-α;
Antagonist Mode; +E2)

| Receptor | Efficacy ($E_{max}$) | | | | |
|---|---|---|---|---|---|
| | Vehicle | 17β-Estradiol | 4-Hydroxytamoxifen | Fulvestrant | ARN-810 |
| None[1] | 3.20 ± 0.16 | 3.95 ± 0.67 | 1.34 ± 0.07 (58%) | 1.15 ± 0.01 (64%) | 0.97 ± 0.01 (70%) |
| Wild-type | 4.91 ± 1.32 | 5.12 ± 1.52 | 1.57 ± 0.08 (68%) | 1.23 ± 0.09 (75%) | 1.16 ± 0.03 (76%) |
| E380Q | 7.12 ± 1.82 | 7.69 ± 1.94 | 2.40 ± 0.46 (66%) | 1.70 ± 0.32 (76%) | 1.72 ± 0.38 (76%) |
| L536P | 5.93 ± 0.95 | 5.66 ± 0.52 | 2.31 ± 0.27 (61%) | 1.73 ± 0.08 (71%) | 1.69 ± 0.10 (72%) |
| L536R | 5.93 ± 0.68 | 5.92 ± 0.67 | 2.34 ± 0.18 (61%) | 1.71 ± 0.16 (71%) | 1.71 ± 0.10 (71%) |
| Y537N | 6.53 ± 0.89 | 6.49 ± 0.97 | 2.27 ± 0.07 (65%) | 1.49 ± 0.00 (77%) | 1.56 ± 0.04 (76%) |
| Y537S | 6.52 ± 1.61 | 6.29 ± 1.03 | 2.56 ± 0.05 (61%) | 1.65 ± 0.12 (75%) | 1.70 ± 0.05 (74%) |
| Y537C | 7.02 ± 0.98 | 7.43 ± 1.84 | 2.45 ± 0.27 (65%) | 1.67 ± 0.19 (76%) | 1.60 ± 0.16 (77%) |
| D538G | 7.00 ± 2.02 | 6.71 ± 1.88 | 2.47 ± 0.37 (65%) | 1.68 ± 0.27 (76%) | 1.53 ± 0.14 (78%) |

MCF-7 cells were used as the negative control.
$E_{max}$ is the maximal stimulated proliferative response at Day 5 relative to Day 0. Percent inhibition compared to vehicle is also presented (%).
Data is the average and standard deviation derived from 2 independent experiments.

TABLE 13

ARN-810 Is a Potent Proliferative Antagonist of MCF-7 Cells Stably
Expressing Clinically Relevant ER-α Mutants (UbC HA-ER-α;
Antagonist Mode; +E2)

| Receptor | Potency ($EC_{50}$; nM) | | |
|---|---|---|---|
| | 4-Hydroxytamoxifen | Fulvestrant | ARN-810 |
| None[1] | 2.474 ± 1.778 | 0.327 ± 0.324 | 4.845 ± 4.422 |
| Wild-type | 2.950 ± 2.507 | 0.516 ± 0.479 | 5.505 ± 6.276 |
| E380Q | 4.924 ± 0.671 | 1.144 ± 0.028 | 8.379 ± 3.311 |
| L536P | 2.128 ± 4.678 | 2.587 ± 2.577 | 7.372 ± 3.929 |
| L536R | 6.090 ± 4.424 | 2.296 ± 1.807 | 6.957 ± 3.758 |
| Y537N | 5.031 ± 0.765 | 1.774 ± 0.387 | 9.498 ± 3.610 |
| Y537S | 10.992 ± 3.703 | 2.355 ± 0.005 | 15.070 ± 2.121 |
| Y537C | 4.558 ± 0.917 | 1.901 ± 0.535 | 9.334 ± 4.464 |
| D538G | 6.966 ± 1.662 | 2.810 ± 0.336 | 10.765 ± 0.375 |

MCF-7 cells were used as the negative control.
Data is the average and standard deviation derived from 2 independent experiments.

TABLE 14

ARN-810 Reduces Viable Cell Number of MCF-7 Cells Stably Expressing
Clinically Relevant ER-α Mutants after 5-Day Incubation (EF1 HA-ER-α; Agonist Mode; −E2)

| Receptor | Efficacy ($E_{max}$) | | | | |
|---|---|---|---|---|---|
| | Vehicle | 17β-Estradiol | 4-Hydroxytamoxifen | Fulvestrant | ARN-810 |
| None[1] | 2.23 ± 0.20 | 4.37 ± 0.71 | 1.49 ± 0.06 (33%) | 1.09 ± 0.16 (51%) | 1.03 ± 0.14 (54%) |
| Wild-type | 5.72 ± 0.97 | 7.35 ± 1.28 | 3.99 ± 0.38 (30%) | 2.12 ± 0.23 (63%) | 2.97 ± 0.50 (48%) |
| E380Q | 6.58 ± 0.72 | 6.23 ± 0.84 | 5.17 ± 0.26 (21%) | 2.50 ± 0.03 (62%) | 3.35 ± 0.07 (49%) |
| L536P | 8.21 ± 0.20 | 8.49 ± 0.94 | 3.47 ± 0.03 (58%) | 3.58 ± 0.10 (56%) | 3.54 ± 0.45 (57%) |

TABLE 14-continued

ARN-810 Reduces Viable Cell Number of MCF-7 Cells Stably Expressing
Clinically Relevant ER-α Mutants after 5-Day Incubation (EF1 HA-ER-α; Agonist Mode; −E2)

| | Efficacy ($E_{max}$) | | | | |
|---|---|---|---|---|---|
| Receptor | Vehicle | 17β-Estradiol | 4-Hydroxytamoxifen | Fulvestrant | ARN-810 |
| L536R | 6.81 ± 1.09 | 6.93 ± 1.50 | 3.91 ± 0.04 (43%) | 3.95 ± 0.36 (42%) | 3.61 ± 0.24 (47%) |
| Y537N | 5.99 ± 0.82 | 5.52 ± 0.43 | 2.43 ± 0.13 (60%) | 0.52 ± 0.09 (91%) | 3.11 ± 0.28 (48%) |
| Y537S | 6.62 ± 0.57 | 6.31 ± 0.36 | 1.59 ± 0.21 (76%) | 0.29 ± 0.01 (96%) | 3.17 ± 0.76 (52%) |
| Y537C | 7.16 ± 0.64 | 8.20 ± 0.49 | 3.81 ± 0.03 (47%) | 2.02 ± 0.08 (72%) | 2.95 ± 0.06 (59%) |
| D538G | 8.81 ± 3.61 | 8.78 ± 3.09 | 2.17 ± 0.67 (75%) | 1.15 ± 0.28 (87%) | 2.22 ± 0.37 (75%) |

MCF-7 cells transduced with an empty EF1 lentiviral vector were used as the negative control.
$E_{max}$ is the maximal stimulated proliferative response at Day 5 relative to Day 0. Percent inhibition compared to vehicle is also presented (%).
Data is the average and standard deviation derived from 2 independent experiments.

TABLE 15

ARN-810 Is a Proliferative Antagonist of MCF-7 Cells Stably Expressing
Clinically Relevant ER-α Mutants (EF1 HA-ER-α; Agonist Mode; −E2)

| | Potency ($EC_{50}$; nM) | | | |
|---|---|---|---|---|
| Receptor | 17β-Estradiol | 4-Hydroxytamoxifen | Fulvestrant | ARN-810 |
| None[1] | 0.020 ± 0.001 | 0.531 ± 0.381 | 0.178 ± 0.129 | 0.828 ± 0.347 |
| Wild-type | 0.518 ± 0.699 | 0.186 ± 0.040 | 0.895 ± 0.173 | 2.839 ± 1.362 |
| E380Q | ND | 26.010 ± 9.122 | 4.355 ± 3.226 | 18.550 ± 7.113 |
| L536P | ND | 4.391 ± 0.723 | 4.511 ± 0.313 | 18.185 ± 3.288 |
| L536R | ND | 7.138 ± 6.636 | 6.288 ± 1.126 | 10.402 ± 6.517 |
| Y537N | ND | 6.041 ± 1.358 | 9.259 ± 2.392 | 97.330 ± 46.85 |
| Y537S | ND | 6.292 ± 3.612 | 42.455 ± 8.436 | 597.000 ± 130.673 |
| Y537C | ND | 1.552 ± 1.228 | 1.483 ± 0.625 | 6.374 ± 0.654 |
| D538G | ND | 18.117 ± 13.736 | 28.395 ± 22.465 | 38.930 ± 5.501 |

MCF-7 cells transduced with an empty EF1 lentiviral vector were used as the negative control.
Data is the average and standard deviation derived from 2 independent experiments.
ND = Not determined.

TABLE 16

ARN-810 Reduces Viable Cell Number of MCF-7 Cells Stably Expressing
Clinically Relevant ER-α Mutants after 5-Day Incubation (EF1 HA-ER-α;
Antagonist Mode; +E2)

| | Efficacy ($E_{max}$) | | | | |
|---|---|---|---|---|---|
| Receptor | Vehicle | 17β-Estradiol | 4-Hydroxytamoxifen | Fulvestrant | ARN-810 |
| None[1] | 3.98 ± 0.36 | 4.24 ± 0.90 | 1.60 ± 0.08 (60%) | 1.04 ± 0.15 (74%) | 1.01 ± 0.12 (75%) |
| Wild-type | 6.75 ± 1.55 | 6.67 ± 1.25 | 4.05 ± 0.36 (40%) | 2.04 ± 0.10 (70%) | 2.78 ± 0.26 (59%) |
| E380Q | 6.23 ± 0.13 | 5.75 ± 0.17 | 5.03 ± 0.85 (19%) | 2.21 ± 0.12 (65%) | 3.00 ± 0.18 (52%) |
| L536P | 9.05 ± 1.12 | 9.07 ± 0.12 | 3.64 ± 0.26 (60%) | 3.65 ± 0.56 (60%) | 3.74 ± 0.53 (59%) |
| L536R | 6.84 ± 1.52 | 6.83 ± 1.36 | 3.65 ± 0.29 (47%) | 3.53 ± 0.28 (48%) | 3.77 ± 0.48 (45%) |
| Y537N | 5.56 ± 0.31 | 5.93 ± 0.15 | 2.39 ± 0.24 (57%) | 0.56 ± 0.02 (90%) | 3.10 ± 0.34 (44%) |
| Y537S | 6.52 ± 0.32 | 6.23 ± 0.25 | 1.43 ± 0.22 (78%) | 0.27 ± 0.10 (96%) | 3.15 ± 0.40 (52%) |
| Y537C | 7.75 ± 0.56 | 8.18 ± 0.53 | 3.76 ± 0.38 (52%) | 1.95 ± 0.01 (75%) | 2.96 ± 0.10 (62%) |
| D538G | 9.20 ± 3.89 | 8.99 ± 3.39 | 2.15 ± 0.74 (77%) | 1.12 ± 0.27 (88%) | 2.22 ± 0.31 (76%) |

MCF-7 cells transduced with an empty EF1 lentiviral vector were used as the negative control.
$E_{max}$ is the maximal stimulated proliferative response at Day 5 relative to Day 0. Percent inhibition compared to vehicle is also presented (%).
Data is the average and standard deviation derived from 2 independent experiments.

TABLE 17

ARN-810 Is a Proliferative Antagonist of MCF-7 Cells Stably Expressing
Clinically Relevant ER-α Mutants (EF1 HA-ER-α;
Antagonist Mode; +E2)

| | Potency (EC$_{50}$; nM) | | |
|---|---|---|---|
| Receptor | 4-Hydroxytamoxifen | Fulvestrant | ARN-810 |
| None[1] | 2.324 ± 0.599 | 1.442 ± 0.156 | 9.270 ± 3.932 |
| Wild-type | 5.158 ± 0.137 | 3.974 ± 0.955 | 28.010 ± 10.324 |
| E380Q | 65.390 ± 24.438 | 10.271 ± 2.615 | 76.230 ± 21.496 |
| L536P | 9.223 ± 0.546 | 16.425 ± 8.210 | 41.885 ± 8.252 |
| L536R | 19.044 ± 18.196 | 35.040 ± 2.772 | 15.570 ± 6.901 |
| Y537N | 5.252 ± 2.840 | 12.351 ± 3.521 | 124.995 ± 35.504 |
| Y537S | 8.083 ± 2.881 | 49.640 ± 18.597 | 433.400 ± 79.479 |
| Y537C | 3.341 ± 0.525 | 3.248 ± 0.431 | 22.745 ± 0.643 |
| D538G | 21.267 ± 16.862 | 29.840 ± 19.502 | 41.640 ± 8.061 |

MCF-7 cells transduced with an empty EF1 lentiviral vector were used as the negative control.
Data is the average and standard deviation derived from 2 independent experiments.

CONCLUSIONS: Compound 1-3 (ARN-810) inhibits the activity of the clinically relevant ESR1 mutations, E380Q, L536R, L536P, Y537C, Y537N, Y537S and D538G, in cell-based transcriptional reporter and cell viability assays. ARN-810 inhibited the transcriptional activity of all the ESR1 mutations in ER-dependent transcriptional reporter assays to levels approaching that observed with the wild-type receptor. In MCF-7 cells stably expressing the ER-α mutants at low levels via the UBC promoter, ARN-810 reduced the number of viable cells by 47%-78% compared to DMSO controls. Although ARN-810 displays nanomolar potency in this assay, ARN-810 demonstrated 1.3- to 2.7-fold reduced potency on mutant ER-α compared to wild-type. Conversely, when the ER-α mutants are overexpressed via the EF1 promoter, ARN-810 exhibits a 0.6- to 210-fold reduction in potency compared to the wild-type receptor, and reduced maximum efficacy ($E_{max}$) response compared to that of 4-hydroxytamoxifen and fulvestrant.

Example 6

Activity of ERM Compound 4-23 on Clinically Relevant ESR1 Mutations

The purpose of this study was to assess the efficacy of ERM 4-23, (S)-2-(4-(2-(3-(fluoromethyl)azetidin-1-yl)ethoxy)phenyl)-3-(3-hydroxyphenyl)-4-methyl-2H-chromen-6-ol, Table 4, on clinically relevant estrogen receptor mutations that are proposed to confer resistance to anti-hormonal therapies such as aromatase inhibitors. Potency and efficacy of ERM 4-23 were measured in vitro in ER dependent transcriptional reporter assays and viability assays of MCF-7 cells stably expressing ER-α mutants. ERM 4-23 activity was compared to the clinically relevant ER-α targeting breast cancer therapeutics 4-hydroxytamoxifen (an active metabolite of tamoxifen) and fulvestrant. In cell-based transcriptional reporter assays, ERM 4-23 inhibited the activity of all the ER-α mutations (E380Q, L536R, L536P, Y537C, Y537N, Y537S and D538G) tested with nanomolar potency, and efficacy approached that observed with the wild-type receptor. Similarly, in MCF-7 cells stably expressing ER-α mutants, ERM 4-23 reduced the number of viable cells by 49%-90% (compared to DMSO control), depending on the mutation and assay format. However, in both assays, ERM 4-23 displayed 0.7 to 23-fold reduced potency across the panel of ESR1 mutations compared to wild-type ER-α.

As in Example 3, the purpose of this study was to determine the activity of ERM 4-23 on clinically relevant ER-α mutations. ERM 4-23 activity was monitored in ER-α transcriptional reporter and cellular viability of MCF-7 cells stably expressing wild-type or mutant ER-α (alpha).

ERM 4-23 was prepared as described in WO 2014/025138. The hydrochloride salt form of the molecule was utilized. The drug substance samples had >95% purity (Purity assessment: nuclear magnetic resonance/liquid chromatography-mass spectrometry) and was an off-white powder. ERM 4-23 was dissolved in dimethyl sulfoxide (DMSO) as a 10 mM stock solution and stored at −20° C. Other Compounds and Formulations were employed as described in Example 3.

ERM Compound 4-23, 4-hydroxytamoxifen, and fulvestrant effects on the transcriptional activity of clinically relevant ESR1 mutations (E380Q, L536R, L536P, Y537C, Y537N, Y537S and D538G) were evaluated in MCF-7 breast cancer cells transiently expressing wild-type ER-α or ER-α mutants as in Example 5. MCF-7 cells were transiently transfected with an ER responsive transcriptional reporter plus wild-type or mutant ER-α expression plasmids, and treated with ERM 4-23, 4-hydroxytamoxifen or fulvestrant ranging from 0.1 pM to 10 μM or 17β-estradiol ranging from 0.1 pM to 1 μM. To assess potential agonist activity of the compounds, the cells were treated in the absence of estradiol. Antagonist assays were run in the presence of 1 nM estradiol. As seen in Table 18, in the absence of estradiol, all of the clinical mutations analyzed demonstrate detectable ligand-independent activity that is inhibited to levels approaching wild-type by ERM 4-23, 4-hydroxytamoxifen and fulvestrant. All antagonists retain nanomolar potency on the mutations tested (Table 19). However, with few exceptions (4-hydroxytamoxifen activity on E380Q and L536P), in agonist mode, all antagonists demonstrate a modest reduction (1.1 to 5.9 fold) in potency on the mutant receptors in comparison to wild-type ER-α, with a maximum of 5.9 fold observed for ERM 4-23 on the Y537S mutation. Similar effects on efficacy and potency were observed when a subset of the ESR1 mutations (L536R, Y537C, Y537N, Y537S and D538G) was analyzed in antagonist mode transcriptional assays. Specifically, on the clinically relevant mutations ERM 4-23 IC$_{50}$ increased 2.2 to 10.2 fold but maximal efficacy approached that observed on the wild-type receptor (Tables 20 and 21).

TABLE 18

ERM 4-23 Inhibits Transcriptional Activity of Clinically Relevant ER-α
Mutations (Agonist Mode, −E2)

| | | | Efficacy ($E_{max}$) | | | |
|---|---|---|---|---|---|---|
| Receptor | n | Vehicle | 17β-Estradiol | 4-Hydroxytamoxifen | Fulvestrant | ERM 4-23 |
| Wild-type | 7 | 1.00 | 3.08 ± 1.21 | 0.24 ± 0.10 (76%) | 0.15 ± 0.09 (85%) | 0.14 ± 0.10 (86%) |
| E380Q | 1 | 2.15 | 3.20 | 0.53 (75%) | 0.38 (82%) | 0.57 (73%) |

TABLE 18-continued

ERM 4-23 Inhibits Transcriptional Activity of Clinically Relevant ER-α Mutations (Agonist Mode, −E2)

| | | | Efficacy ($E_{max}$) | | | |
|---|---|---|---|---|---|---|
| Receptor | n | Vehicle | 17β-Estradiol | 4-Hydroxytamoxifen | Fulvestrant | ERM 4-23 |
| L536R | 7 | 1.47 ± 0.51 | 2.64 ± 0.64 | 0.33 ± 0.13 (78%) | 0.32 ± 0.12 (78%) | 0.29 ± 0.22 (80%) |
| L536P | 1 | 3.12 | 4.95 | 0.44 (86%) | 0.42 (87%) | 1.01 (68%) |
| Y537C | 7 | 3.2 ± 0.32 | 2.94 ± 2.12 | 0.42 ± 0.11 (87%) | 0.28 ± 0.10 (91%) | 0.35 ± 0.27 (89%) |
| Y537N | 7 | 4.06 ± 1.39 | 3.70 ± 1.54 | 0.38 ± 0.14 (91%) | 0.30 ± 0.18 (93%) | 0.32 ± 0.27 (92%) |
| Y537S | 7 | 7.54 ± 1.95 | 1.95 ± 2.01 | 0.41 ± 0.27 (95%) | 0.34 ± 0.13 (96%) | 0.19 ± 0.19 (98%) |
| D538G | 7 | 4.31 ± 1.22 | 2.82 ± 2.32 | 0.27 ± 0.20 (94%) | 0.24 ± 0.14 (94%) | 0.18 ± 0.23 (96%) |

$E_{max}$ is the maximal stimulated activity relative to vehicle treated wild-type ER-α.
Percent inhibition compared to vehicle is also presented (%).
Data is the average and standard deviation derived from n independent experiments.

TABLE 19

ERM 4-23 is a Potent Transcriptional Inhibitor of Activity of Clinically Relevant ER-α Mutations (Agonist Mode, −E2)

| | | | Potency ($EC_{50}$; nM) | | |
|---|---|---|---|---|---|
| Receptor | N | 17β-Estradiol | 4-Hydroxytamoxifen | Fulvestrant | ERM 4-23 |
| Wild-type | 7 | 0.13 ± 0.09 | 2.16 ± 3.44 | 0.38 ± 0.47 | 0.99 ± 1.31 |
| E380Q | 1 | 0.33 | 0.49 | 0.72 | 1.12 |
| L536R | 7 | 0.62 ± 1.07 | 4.06 ± 4.32 | 1.72 ± 1.39 | 4.69 ± 7.44 |
| L536P | 1 | 0.24 | 0.48 | 1.20 | 2.86 |
| Y537C | 7 | >100 | 2.99 ± 3.45 | 0.55 ± 0.38 | 1.34 ± 1.47 |
| Y537N | 7 | 20.23 ± 40.95 | 3.15 ± 2.76 | 0.60 ± 0.47 | 2.31 ± 2.50 |
| Y537S | 7 | >100 | 5.81 ± 2.95 | 2.00 ± 1.07 | 5.81 ± 6.29 |
| D538G | 7 | >100 | 3.10 ± 2.38 | 2.07 ± 1.40 | 5.31 ± 5.65 |

Data is the average and standard deviation derived from n independent experiments.

TABLE 20

ERM 4-23 Antagonizes Transcriptional Activity of Clinically Relevant ER-α Mutations (Antagonist Mode, +E2)

| | | | Efficacy ($E_{max}$) | | | |
|---|---|---|---|---|---|---|
| Receptor | n | Vehicle | 17β-Estradiol | 4-Hydroxytamoxifen | Fulvestrant | ERM 4-23 |
| Wild-type | 3 | 2.25 ± 0.55 | 1.10 ± 1.17 | 0.04 ± 0.07 (98%) | 0.06 ± 0.08 (97%) | 0.08 ± 0.07 (96%) |
| L536R | 3 | 2.61 ± 0.96 | 1.60 ± 1.43 | 0.26 ± 0.08 (90%) | 0.30 ± 0.11 (89%) | 0.15 ± 0.07 (94%) |
| Y537C | 3 | 3.13 ± 0.76 | 0.52 ± 0.91 | 0.31 ± 0.22 (90%) | 0.16 ± 0.12 (95%) | 0.16 ± 0.09 (95%) |
| Y537N | 3 | 3.94 ± 2.24 | 1.56 ± 1.27 | 0.31 ± 0.32 (92%) | 0.20 ± 0.20 (95%) | 0.16 ± 0.08 (96%) |
| Y537S | 3 | 5.79 ± 1.85 | 1.35 ± 1.37 | 0.22 ± 0.23 (96%) | 0.37 ± 0.30 (94%) | 0.26 ± 0.38 (96%) |
| D538G | 3 | 5.31 ± 1.88 | 0.86 ± 1.50 | 0.12 ± 0.22 (98%) | 0.10 ± 0.17 (98%) | 0.26 ± 0.24 (95%) |

$E_{max}$ is the maximal stimulated activity relative to vehicle treated wild-type ER-α.
Percent inhibition compared to vehicle is also presented (%).
Data is the average and standard deviation derived from n independent experiments.

TABLE 21

ERM 4-23 is a Potent Transcriptional Antagonist Activity of Clinically Relevant ER-α Mutations (Antagonist Mode, +E2)

| | | | Potency ($EC_{50}$; nM) | | |
|---|---|---|---|---|---|
| Receptor | n | 17β-Estradiol | 4-Hydroxytamoxifen | Fulvestrant | ERM 4-23 |
| Wild-type | 3 | 1.10 ± 1.17 | 9.04 ± 7.59 | 1.51 ± 0.70 | 2.55 ± 2.50 |
| L536R | 3 | 1.60 ± 1.43 | 13.87 ± 3.68 | 13.4 ± 9.95 | 21.06 ± 12.06 |
| Y537C | 3 | 0.52 ± 0.91 | 9.92 ± 1.35 | 2.16 ± 093 | 5.60 ± 3.39 |
| Y537N | 3 | 1.56 ± 1.27 | 4.55 ± 2.90 | 2.90 ± 2.56 | 8.40 ± 8.14 |
| Y537S | 3 | 1.35 ± 1.37 | 102.69 ± 151.87 | 5.30 ± 2.14 | 8.31 ± 6.47 |
| D538G | 3 | 0.86 ± 1.50 | 9.26 ± 1.58 | 4.64 ± 2.44 | 25.91 ± 35.97 |

Data is the average and standard deviation derived from n independent experiments.

Viability Assays: To assess the ability of ERM 4-23 to antagonize the ligand-independent proliferative activity of the constitutively active ER-α mutations identified in patients, MCF-7 cell lines that stably express wild-type, E380Q, L536P, L536R, Y537N, Y537S, Y537C and D38G amino-terminal hemaglutinin-tagged ER-α (HA-ER-α) were generated. Because ER-α overexpression can induce ligand-independent growth and also can saturate the ligand mediated degradation pathway independent stable cell lines were created for each receptor utilizing the UbC and EF1 promoter to drive ER-α expression. The UbC promoter is reported by manufacturer (System Biosciences) to express low to moderate RNA levels while the EF1 promoter expresses high levels (System Biosciences). As determined by quantitative Western blot analysis, the UbC based cell lines express HA-ER-α protein at levels less than 10% of endogenous ER-α. On the other hand, the EF1 promoter based lines express HA-ER-α and the mutants at 2- to 6-fold higher levels than the endogenous protein.

Consistent with their activity in the transcriptional reporter assay, expression of the clinically identified ER-α mutants in MCF-7 cells by either the UbC or EF1 promoter conferred the ability of the cells to proliferate in the absence of 17β-estradiol (Tables 22 and 26 5). However, the high level of wild-type ER-α expression (approximately 2-3 fold more than endogenous protein levels) attained using the EF1 promoter is also sufficient to promote ligand independent growth. In agonist mode, ERM 4-23, 4-hydroxytamoxifen and fulvestrant antagonized proliferation of MCF-7 cell lines stably expressing wild-type, E380Q, L536P, L536R, Y537N, Y537S, Y537C and D538G HA-ER-α via either promoter (Tables 22 and 26). The fulvestrant and ERM 4-23 demonstrate similar efficacy (ranging from 47% to 66% and 42% to 96% inhibition for the UbC and EF1-derived lines, respectively) while 4-hydroxytamoxifen displayed reduced efficacy on all the mutations tested. In agonist mode all three antagonists displayed high picomolar to low nanomolar IC50 against the UbC HA-ER-α mutant cell lines and low nanomolar potency in the EF1-derived lines (Tables 23 and 27). The UbC wild-type HA-ER-α cell line did not proliferate sufficiently in absence of E2 to derive an accurate IC50, however, in the EF1-derived lines all antagonists demonstrate reduced potency on the mutant receptors compared to wild-type (8- to 140-fold, 2- to 47-fold and 0.7- to 24-fold for 4-hydroxytamoxifen, fulvestrant and ERM 4-23, respectively). Similar observations of antagonist efficacy and potency were observed when the proliferation assays were performed in antagonist mode (Tables 24, 25, 28, 29). However, in the presence of 17β-estradiol, the difference in antagonist potency between the wild-type and the mutant HA-ER-α bearing cell lines was less pronounced than observed in the EF-1 agonist assay (13-fold maximum).

TABLE 22

ERM 4-23 Reduces Viable Cell Number of MCF-7 Cells Stably Expressing Clinically Relevant ER-α Mutants after 5-Day Incubation (UbC HA-ER-α; Agonist Mode; −E2)

| | Efficacy ($E_{max}$) | | | | |
| --- | --- | --- | --- | --- | --- |
| Receptor | Vehicle | 17β-Estradiol | 4-Hydroxytamoxifen | Fulvestrant | ERM 4-23 |
| None | 1.76 ± 0.26 | 4.12 ± 0.88 | 1.42 ± 0.43 (19%) | 1.27 ± 0.24 (28%) | 1.20 ± 0.27 (31%) |
| Wild-type | 1.85 ± 0.46 | 4.43 ± 0.88 | 1.58 ± 0.16 (14%) | 1.17 ± 0.13 (37%) | 1.13 ± 0.13 (39%) |
| E380Q | 4.27 ± 0.87 | 7.36 ± 1.07 | 2.40 ± 0.39 (44%) | 1.70 ± 0.30 (60%) | 1.78 ± 0.28 (58%) |
| L536P | 3.16 ± 0.36 | 5.06 ± 0.76 | 2.06 ± 0.19 (35%) | 1.66 ± 0.11 (47%) | 1.62 ± 0.13 (49%) |
| L536R | 3.82 ± 0.78 | 5.72 ± 0.74 | 2.26 ± 0.36 (41%) | 1.71 ± 0.22 (55%) | 1.80 ± 0.26 (53%) |
| Y537N | 4.31 ± 0.83 | 5.67 ± 1.06 | 2.34 ± 0.29 (46%) | 1.61 ± 0.15 (63%) | 1.63 ± 0.17 (62%) |
| Y537S | 5.16 ± 0.60 | 6.57 ± 0.89 | 2.76 ± 0.03 (47%) | 1.88 ± 0.13 (64%) | 1.85 ± 0.24 (64%) |
| Y537C | 4.88 ± 0.17 | 6.72 ± 0.46 | 2.63 ± 0.19 (46%) | 1.77 ± 0.11 (64%) | 1.82 ± 0.17 (63%) |
| D538G | 5.64 ± 1.35 | 7.21 ± 1.69 | 2.71 ± 0.43 (52%) | 1.91 ± 0.28 (66%) | 1.97 ± 0.30 (65%) |

MCF-7 cells were used as the negative control.
$E_{max}$ is the maximal stimulated proliferative response at Day 5 relative to Day 0. Percent inhibition compared to vehicle is also presented (%).
Data is the average and standard deviation derived from 4 independent experiments.

TABLE 23

ERM 4-23 Is a Potent Proliferative Antagonist of MCF-7 Cells Stably Expressing Clinically Relevant ER-α Mutants (UbC HA-ER-α; Agonist Mode; −E2)

| | Potency ($EC_{50}$; nM) | | | |
| --- | --- | --- | --- | --- |
| Receptor | 17β-Estradiol | 4-Hydroxytamoxifen | Fulvestrant | ERM 4-23 |
| None | 0.279 ± 0.518 | 262.7 ± 524.8 | 0.050 ± 0.017 | 0.227 ± 0.210 |
| Wild-type | 0.101 ± 0.160 | 0.626 ± 0.528 | 0.080 ± 0.042 | 4.037 ± 8.009 |
| E380Q | 0.013 ± 0.011 | 1.594 ± 0.681 | 0.248 ± 0.094 | 0.208 ± 0.141 |
| L536P | 0.212 ± 0.401 | 0.821 ± 0.726 | 0.298 ± 0.132 | 0.231 ± 0.104 |
| L536R | 0.008 ± 0.006 | 1.056 ± 0.714 | 0.257 ± 0.090 | 0.334 ± 0.270 |
| Y537N | 0.126 ± 0.233 | 1.585 ± 0.955 | 0.355 ± 0.163 | 0.446 ± 0.219 |
| Y537S | 0.010 ± 0.006 | 14.57 ± 10.95 | 1.057 ± 0.263 | 1.942 ± 0.937 |
| Y537C | 0.019 ± 0.010 | 1.475 ± 0.278 | 0.388 ± 0.106 | 0.319 ± 0.205 |
| D538G | 0.022 ± 0.015 | 3.446 ± 0.821 | 0.999 ± 0.358 | 1.385 ± 0.701 |

MCF-7 cells were used as the negative control.
Data is the average and standard deviation derived from 4 independent experiments.

TABLE 24

ERM 4-23 Reduces Viable Cell Number of MCF-7 Cells Stably Expressing Clinically Relevant ER-α Mutants after 5-Day Incubation (UbC HA-ER-α; Antagonist Mode; +E2)

| Receptor | Efficacy ($E_{max}$) | | | | |
|---|---|---|---|---|---|
| | Vehicle | 17β-Estradiol | 4-Hydroxytamoxifen | Fulvestrant | ERM 4-23 |
| None | 3.20 ± 0.16 | 3.95 ± 0.67 | 1.34 ± 0.07 (58%) | 1.15 ± 0.01 (64%) | 1.08 ± 0.04 (66%) |
| Wild-type | 4.91 ± 1.32 | 5.12 ± 1.52 | 1.57 ± 0.08 (68%) | 1.23 ± 0.09 (75%) | 1.20 ± 0.10 (76%) |
| E380Q | 7.12 ± 1.82 | 7.69 ± 1.94 | 2.40 ± 0.46 (66%) | 1.70 ± 0.32 (76%) | 1.61 ± 0.34 (77%) |
| L536P | 5.93 ± 0.95 | 5.66 ± 0.52 | 2.31 ± 0.27 (61%) | 1.73 ± 0.08 (71%) | 1.87 ± 0.27 (69%) |
| L536R | 5.93 ± 0.68 | 5.92 ± 0.67 | 2.34 ± 0.18 (61%) | 1.71 ± 0.16 (71%) | 1.73 ± 0.31 (71%) |
| Y537N | 6.53 ± 0.89 | 6.49 ± 0.97 | 2.27 ± 0.07 (65%) | 1.49 ± 0.00 (77%) | 1.70 ± 0.03 (74%) |
| Y537S | 6.52 ± 1.61 | 6.29 ± 1.03 | 2.56 ± 0.05 (61%) | 1.65 ± 0.12 (75%) | 1.73 ± 0.26 (73%) |
| Y537C | 7.02 ± 0.98 | 7.43 ± 1.84 | 2.45 ± 0.27 (65%) | 1.67 ± 0.19 (76%) | 1.85 ± 0.10 (74%) |
| D538G | 7.00 ± 2.02 | 6.71 ± 1.88 | 2.47 ± 0.37 (65%) | 1.68 ± 0.27 (76%) | 1.68 ± 0.22 (76%) |

MCF-7 cells were used as the negative control.
$E_{max}$ is the maximal stimulated proliferative response at Day 5 relative to Day 0. Percent inhibition compared to vehicle is also presented (%).
Data is the average and standard deviation derived from 2 independent experiments.

TABLE 25

ERM 4-23 is a Potent Proliferative Antagonist of MCF-7 Cells Stably Expressing Clinically Relevant ER-α Mutants (UbC HA-ER-α; Antagonist Mode; +E2)

| Receptor | Potency ($EC_{50}$; nM) | | |
|---|---|---|---|
| | 4-Hydroxytamoxifen | Fulvestrant | ERM 4-23 |
| None | 2.474 ± 1.778 | 0.327 ± 0.324 | 0.378 ± 0.216 |
| Wild-type | 2.950 ± 2.507 | 0.516 ± 0.479 | 0.599 ± 0.300 |
| E380Q | 4.924 ± 0.671 | 1.144 ± 0.028 | 1.025 ± 0.163 |
| L536P | 2.128 ± 4.678 | 2.587 ± 2.577 | 2.087 ± 0.425 |
| L536R | 6.090 ± 4.424 | 2.296 ± 1.807 | 2.578 ± 0.181 |
| Y537N | 5.031 ± 0.765 | 1.774 ± 0.387 | 2.638 ± 1.858 |
| Y537S | 10.992 ± 3.703 | 2.355 ± 0.005 | 5.460 ± 4.711 |
| Y537C | 4.558 ± 0.917 | 1.901 ± 0.535 | 1.477 ± 0.583 |
| D538G | 6.966 ± 1.662 | 2.810 ± 0.336 | 4.393 ± 4.114 |

MCF-7 cells were used as the negative control.
Data is the average and standard deviation derived from 2 independent experiments.

TABLE 26

ERM 4-23 Reduces Viable Cell Number of MCF-7 Cells Stably Expressing Clinically Relevant ER-α Mutants after 5-Day Incubation (EF1 HA-ER-α; Agonist Mode; −E2)

| Receptor | Efficacy ($E_{max}$) | | | | |
|---|---|---|---|---|---|
| | Vehicle | 17β-Estradiol | 4-Hydroxytamoxifen | Fulvestrant | ERM 4-23 |
| None | 2.23 ± 0.20 | 4.37 ± 0.71 | 1.49 ± 0.06 (33%) | 1.09 ± 0.16 (51%) | 1.06 ± 0.24 (52%) |
| Wild-type | 5.72 ± 0.97 | 7.35 ± 1.28 | 3.99 ± 0.38 (30%) | 2.12 ± 0.23 (63%) | 2.17 ± 0.03 (62%) |
| E380Q | 6.58 ± 0.72 | 6.23 ± 0.84 | 5.17 ± 0.26 (21%) | 2.50 ± 0.03 (62%) | 2.43 ± 0.02 (63%) |
| L536P | 8.21 ± 0.20 | 8.49 ± 0.94 | 3.47 ± 0.03 (58%) | 3.58 ± 0.10 (56%) | 3.11 ± 0.40 (62%) |
| L536R | 6.81 ± 1.09 | 6.93 ± 1.50 | 3.91 ± 0.04 (43%) | 3.95 ± 0.36 (42%) | 2.94 ± 0.34 (57%) |
| Y537N | 5.99 ± 0.82 | 5.52 ± 0.43 | 2.43 ± 0.13 (60%) | 0.52 ± 0.09 (91%) | 0.74 ± 0.01 (88%) |
| Y537S | 6.62 ± 0.57 | 6.31 ± 0.36 | 1.59 ± 0.21 (76%) | 0.29 ± 0.01 (96%) | 0.68 ± 0.13 (90%) |
| Y537C | 7.16 ± 0.64 | 8.20 ± 0.49 | 3.81 ± 0.03 (47%) | 2.02 ± 0.08 (72%) | 1.80 ± 0.05 (75%) |
| D538G | 8.81 ± 3.61 | 8.78 ± 3.09 | 2.17 ± 0.67 (75%) | 1.15 ± 0.28 (87%) | 1.07 ± 0.23 (88%) |

MCF-7 cells transduced with an empty EF1 lentiviral vector were used as the negative control.
$E_{max}$ is the maximal stimulated proliferative response at Day 5 relative to Day 0. Percent inhibition compared to vehicle is also presented (%).
Data is the average and standard deviation derived from 2 independent experiments.

TABLE 27

ERM 4-23 is a Potent Proliferative Antagonist of MCF-7 Cells Stably Expressing Clinically Relevant ER-α Mutants (EF1 HA-ER-α; Antagonist Mode; −E2)

| Receptor | Potency ($EC_{50}$; nM) | | | |
|---|---|---|---|---|
| | 17β-Estradiol | 4-Hydroxytamoxifen | Fulvestrant | ERM 4-23 |
| None | 0.020 ± 0.001 | 0.531 ± 0.381 | 0.178 ± 0.129 | 0.286 ± 0.294 |
| Wild-type | 0.518 ± 0.699 | 0.186 ± 0.040 | 0.895 ± 0.173 | 2.133 ± 2.062 |

TABLE 27-continued

ERM 4-23 is a Potent Proliferative Antagonist of MCF-7 Cells Stably
Expressing Clinically Relevant ER-α Mutants (EF1 HA-ER-α;
Antagonist Mode; −E2)

| Receptor | Potency (EC$_{50}$; nM) | | | |
|---|---|---|---|---|
| | 17β-Estradiol | 4-Hydroxytamoxifen | Fulvestrant | ERM 4-23 |
| E380Q | ND | 26.010 ± 9.122 | 4.355 ± 3.226 | 3.764 ± 3.107 |
| L536P | ND | 4.391 ± 0.723 | 4.511 ± 0.313 | 4.776 ± 4.672 |
| L536R | ND | 7.138 ± 6.636 | 6.288 ± 1.126 | 11.260 ± 9.221 |
| Y537N | ND | 6.041 ± 1.358 | 9.259 ± 2.392 | 15.993 ± 17.631 |
| Y537S | ND | 6.292 ± 3.612 | 42.455 ± 8.436 | 46.800 ± 44.123 |
| Y537C | ND | 1.552 ± 1.228 | 1.483 ± 0.625 | 1.443 ± 1.010 |
| D538G | ND | 18.117 ± 13.736 | 28.395 ± 22.465 | 50.598 ± 62.894 |

MCF-7 cells transduced with an empty EF1 lentiviral vector were used as the negative control.
Data is the average and standard deviation derived from 2 independent experiments.
ND = Not determined.

TABLE 28

ERM 4-23 Reduces Viable Cell Number of MCF-7 Cells Stably
Expressing Clinically Relevant ER-α Mutants after 5-Day Incubation (EF1 HA-
ER-α; Antagonist Mode; +E2)

| Receptor | Efficacy (E$_{max}$) | | | | |
|---|---|---|---|---|---|
| | Vehicle | 17β-Estradiol | 4-Hydroxytamoxifen | Fulvestrant | ERM 4-23 |
| None | 3.98 ± 0.36 | 4.24 ± 0.90 | 1.60 ± 0.08 (60%) | 1.04 ± 0.15 (74%) | 0.96 ± 0.12 (76%) |
| Wild-type | 6.75 ± 1.55 | 6.67 ± 1.25 | 4.05 ± 0.36 (40%) | 2.04 ± 0.10 (70%) | 2.17 ± 0.29 (68%) |
| E380Q | 6.23 ± 0.13 | 5.75 ± 0.17 | 5.03 ± 0.85 (19%) | 2.21 ± 0.12 (65%) | 2.39 ± 0.24 (62%) |
| L536P | 9.05 ± 1.12 | 9.07 ± 0.12 | 3.64 ± 0.26 (60%) | 3.65 ± 0.56 (60%) | 3.25 ± 0.07 (64%) |
| L536R | 6.84 ± 1.52 | 6.83 ± 1.36 | 3.65 ± 0.29 (47%) | 3.53 ± 0.28 (48%) | 2.76 ± 0.50 (60%) |
| Y537N | 5.56 ± 0.31 | 5.93 ± 0.15 | 2.39 ± 0.24 (57%) | 0.56 ± 0.02 (90%) | 0.70 ± 0.01 (87%) |
| Y537S | 6.52 ± 0.32 | 6.23 ± 0.25 | 1.43 ± 0.22 (78%) | 0.27 ± 0.10 (96%) | 0.68 ± 0.20 (90%) |
| Y537C | 7.75 ± 0.56 | 8.18 ± 0.53 | 3.76 ± 0.38 (52%) | 1.95 ± 0.01 (75%) | 1.76 ± 0.18 (77%) |
| D538G | 9.20 ± 3.89 | 8.99 ± 3.39 | 2.15 ± 0.74 (77%) | 1.12 ± 0.27 (88%) | 0.98 ± 0.46 (89%) |

MCF-7 cells transduced with an empty EF1 lentiviral vector were used as the negative control.
E$_{max}$ is the maximal stimulated proliferative response at Day 5 relative to Day 0. Percent inhibition compared to vehicle is also presented (%).
Data is the average and standard deviation derived from 2 independent experiments.

TABLE 29

ERM 4-23 is a Potent Proliferative Antagonist of MCF-7 Cells
Stably Expressing Clinically Relevant ER-α Mutants
(EF1 HA-ER-α; Antagonist Mode; +E2)

| Receptor | Potency (EC$_{50}$; nM) | | |
|---|---|---|---|
| | 4-Hydroxytamoxifen | Fulvestrant | ERM 4-23 |
| None | 2.324 ± 0.599 | 1.442 ± 0.156 | 2.813 ± 3.278 |
| Wild-type | 5.158 ± 0.137 | 3.974 ± 0.955 | 8.649 ± 10.538 |
| E380Q | 65.390 ± 24.438 | 10.271 ± 2.615 | 14.030 ± 15.401 |
| L536P | 9.223 ± 0.546 | 16.425 ± 8.210 | 15.110 ± 13.591 |
| L536R | 19.044 ± 18.196 | 35.040 ± 2.772 | 53.346 ± 65.781 |
| Y537N | 5.252 ± 2.840 | 12.351 ± 3.521 | 45.548 ± 51.707 |
| Y537S | 8.083 ± 2.881 | 49.640 ± 18.597 | 81.835 ± 92.723 |
| Y537C | 3.341 ± 0.525 | 3.248 ± 0.431 | 10.176 ± 12.960 |
| D538G | 21.267 ± 16.862 | 29.840 ± 19.502 | 96.745 ± 121.983 |

MCF-7 cells transduced with an empty EF1 lentiviral vector were used as the negative control.
Data is the average and standard deviation derived from 2 independent experiments.

CONCLUSIONS: ERM 4-23 inhibits the activity of the clinically relevant ESR1 mutations, E380Q, L536R, L536P, Y537C, Y537N, Y537S and D538G, in cell-based transcriptional reporter and cell viability assays. ERM 4-23 inhibited the transcriptional activity of all the ESR1 mutations in ER-dependent transcriptional reporter assays to levels approaching that observed with the wild-type receptor. In MCF-7 cells stably expressing ER-α mutations, ERM 4-23 reduced the number of viable cells by 49%-90% compared to DMSO controls. Although ERM 4-23 displays low nanomolar potency in these assays, ERM 4-23 demonstrated 0.7- to 24-fold reduced potency on mutant ER-α compared to wild-type. ERM 4-23 exhibits IC50 potency similar to 4-hydroxytamoxifen and fulvestrant, and maximum efficacy (E$_{max}$) response similar to that of fulvestrant.

Example 7

In Vitro Cell Proliferation Assay

Efficacy of estrogen receptor modulator compounds and chemotherapeutic compounds are measured by a cell proliferation assay employing the following protocol (Mendoza et al (2002) Cancer Res. 62:5485-5488).

The CellTiter-Glo® Luminescent Cell Viability Assay is a homogeneous method to determine the number of viable cells in culture based on quantitation of the ATP present, which signals the presence of metabolically active cells. The CellTiter-Glo® Assay is designed for use with multiwell plate formats, making it ideal for automated high-throughput screening (HTS), cell proliferation and cytotoxicity assays. The homogeneous assay procedure involves adding a single reagent (CellTiter-Glo® Reagent) directly to cells cultured in serum-supplemented medium. Cell washing, removal of medium or multiple pipetting steps are not required. The Cell Titer-Glo® Luminescent Cell Viability Assay, including reagents and protocol are commercially available (Promega Corp., Madison, Wis., Technical Bulletin TB288).

The assay assesses the ability of compounds to enter cells and inhibit cell proliferation. The assay principle is based on the determination of the number of viable cells present by quantitating the ATP present in a homogenous assay where addition of the Cell Titer-Glo® reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N (overnight) at 37° C., 5% $CO_2$.

Day 2—Add Drug to Cells, Compound Dilution, DMSO Plates (serial 1:2 for 9 points). Add 20 µl of compound at 10 mM in the 2nd column of 96 well plate. Perform serial 1:2 across the plate (10 µl+20 µl 100% DMSO) for a total of 9 points using Precision Media Plates 96-well conical bottom polypropylene plates from Nunc (cat.#249946) (1:50 dilution). Add 147 µl of Media into all wells. Transfer 3 µl of DMSO+compound from each well in the DMSO Plate to each corresponding well on Media Plate using Rapidplate® (Caliper, a Perkin-Elmer Co.). For 2 drug combination studies, transfer one drug 1.5 µl of DMSO+compound from each well in the DMSO Plate to each corresponding well on Media Plate using Rapidplate. Then, transfer another drug 1.5 µl to the medium plate.

Drug Addition to Cells, Cell Plate (1:10 dilution): Add 6 µl of media+compound directly to cells (54 µl of media on the cells already). Incubate 3 days at 37° C., 5% $CO_2$ in an incubator that will not be opened often.

Day 5—Develop Plates, Thaw Cell Titer Glo Buffer at room temperature: Remove Cell Plates from 37° C. and equilibrate to room temperature for about 30 minutes. Add Cell Titer-Glo® Buffer to Cell Titer-Glo® Substrate (bottle to bottle). Add 30 µl Cell Titer-Glo® Reagent (Promega cat.# G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate® robot (Zymark Corp., Hopkinton, Mass.). The diluted compounds were then added to quadruplicate wells in 384-well cell plates and incubated at 37° C. and 5% $CO_2$. After 4 days, relative numbers of viable cells were measured by luminescence using Cell Titer-Glo® (Promega) according to the manufacturer's instructions and read on a Wallac Multilabel Reader® (PerkinElmer, Foster City). EC50 values were calculated using Prism® 4.0 software (GraphPad, San Diego). Drugs in combination assays were dosed starting at $4 \times EC_{50}$ concentrations. If cases where the EC50 of the drug was >2.5 µM, the highest concentration used was 10 µM. Estrogen receptor modulator compounds and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see Table 3 for cell lines and tumor type) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo® Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.
9. Analyze using the Chou and Talalay combination method and Dose-Effect Analysis with CalcuSyn® software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer-Glo® reagent (Promega Inc., Madison, Wis.). DMSO treatment was used as control in all viability assays. $IC_{50}$ values were calculated using XL fit software (IDBS, Alameda, Calif.)

The cell lines were obtained from either ATCC (American Type Culture Collection, Manassas, Va.) or DSMZ (Deutsche Sammlung von Mikroorganismen and Zellkulturen GmbH, Braunschweig, DE). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 8

In Vivo Mouse Tumor Xenograft Efficacy

Mice: Female severe combined immunodeficiency mice (Fox Chase SCID®, C.B-17/IcrHsd, Harlan) or nude mice (Taconic Farms, Harlan) were 8 to 9 weeks old and had a BW range of 15.1 to 21.4 grams on Day 0 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-o'cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation: Xenografts were initiated with cancer cells. Cells were cultured in RPMI 1640 medium supplemented with 10% fetal bovine serum, 2 mM glutamine, 100 units/mL penicillin, 100 µg/mL streptomycin sulfate and 25 µg/mL gentamicin. The cells were harvested during exponential growth and resuspended in phosphate buffered saline (PBS) at a concentration of $5\times10^6$ or $10\times10^6$ cells/mL depending on the doubling time of the cell line. Tumor cells were implanted subcutaneously in the right flank, and tumor growth was monitored as the average size approached the target range of 100 to 150 mm3. Twenty-one days after tumor implantation, designated as Day 0 of the study, the mice were placed into four groups each consisting of ten mice with individual tumor volumes ranging from 75-172 mm3 and group mean tumor volumes from 120-121 mm3 (see Appendix A). Volume was calculated using the formula:

Tumor Volume $(mm^3)=(w^2\times l)/2$, where $w$=width and $l$=length in mm of a tumor.

Tumor weight may be estimated with the assumption that 1 mg is equivalent to 1 mm3 of tumor volume.

Therapeutic Agents: estrogen receptor modulator compounds and chemotherapeutic agents were typically prepared from dry powders, stored at room temperature, and protected from light. Drug doses were prepared weekly in 0.5% methylcellulose: 0.2% Tween 80 in deionized water ("Vehicle") and stored at 4° C. Doses of compounds were prepared on each day of dosing by diluting an aliquot of the stock with sterile saline (0.9% NaCl). All doses were formulated to deliver the stated mg/kg dosage in a volume of 0.2 mL per 20 grams of body weight (10 mL/kg).

Treatment: All doses were scaled to the body weights of the individual animals and were provided by the route indicated in each of the figures.

Endpoint: Tumor volume was measured in 2 dimensions (length and width), using Ultra Cal IV calipers (Model 54 10 111; Fred V. Fowler Company), as follows: tumor volume $(mm^3)=(length\times width)\times 0.5$ and analyzed using Excel version 11.2 (Microsoft Corporation). A linear mixed effect (LME) modeling approach was used to analyze the repeated measurement of tumor volumes from the same animals over time (Pinheiro J, et al. nlme: linear and nonlinear mixed effects models. R package version 3.1 92. 2009; Tan N, et al. Clin. Cancer Res. 2011; 17(6):1394-1404). This approach addresses both repeated measurements and modest dropouts due to any non-treatment-related death of animals before study end. Cubic regression splines were used to fit a nonlinear profile to the time courses of log 2 tumor volume at each dose level. These nonlinear profiles were then related to dose within the mixed model. Tumor growth inhibition as a percentage of vehicle control (% TGI) was calculated as the percentage of the area under the fitted curve (AUC) for the respective dose group per day in relation to the vehicle, using the following formula: % $TGI=100\times(1-AUC_{dose}/AUC_{veh})$. Using this formula, a TGI value of 100% indicates tumor stasis, a TGI value of >1% but <100% indicates tumor growth delay, and a TGI value of >100% indicates tumor regression. Partial response (PR) for an animal was defined as a tumor regression of >50% but <100% of the starting tumor volume. Complete response (CR) was defined as 100% tumor regression (i.e., no measurable tumor) on any day during the study.

Toxicity: Animals were weighed daily for the first five days of the study and twice weekly thereafter. Animal body weights were measured using an Adventurer Pro® AV812 scale (Ohaus Corporation). Percent weight change was calculated as follows: body weight change (%)= $[(weight_{day\ new}-weight_{day\ 0})/weight_{day\ 0}]\times 100$. The mice were observed frequently for overt signs of any adverse, treatment-related side effects, and clinical signs of toxicity were recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference. The examples and embodiments described herein are for illustrative purposes only and various modifications or changes suggested to persons skilled in the art are to be included within the spirit and purview of this application and scope of the appended claims.

What is claimed is:

1. A method for treating an ER-related disease or condition comprising administering an estrogen receptor modulator compound to a patient having a mutation in the ESR1 gene,
wherein the ER-related disease or condition is breast cancer;
the mutation in the ESR1 gene is an amino acid substitution in the ligand binding domain of the estrogen receptor selected from E380Q, L536R, L536P, Y537C, Y537N, Y537S and D538G of SEQ ID NO:2;
and the estrogen receptor modulator compound has the structure:

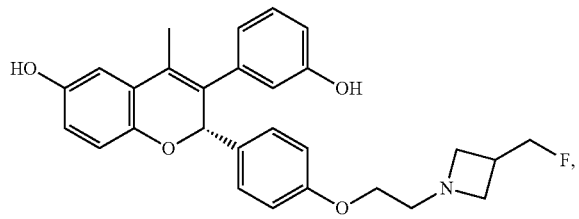 [SMILES: CC1=C(c2cccc(O)c2)[C@H](c2ccc(OCCN3CC(CF)C3)cc2)Oc2ccc(O)cc21]

or a pharmaceutically acceptable salt, or solvate thereof.

2. The method of claim 1 wherein the breast cancer is metastatic, hormone resistant, estrogen receptor positive, estrogen receptor negative, progesterone receptor negative, HER2 positive, or HER2 negative breast cancer.

3. The method of claim 2 wherein the breast cancer is resistant to treatment with an aromatase inhibitor.

4. The method of claim 3 wherein the aromatase inhibitor is anastrozole, letrozole, or exemestane.

5. The method of claim 1 wherein the breast cancer is Basal or Luminal subtype.

6. The method of claim 1 wherein the patient is a pre-menopausal or post-menopausal female patient.

7. The method of claim 1 wherein the patient has failed one or more anti-cancer therapies.

8. The method of claim 1 wherein the mutation in the ESR1 gene is a somatic mutation.

9. The method of claim 1 wherein the patient expresses a wild-type ER and a mutant ER.

10. The method of claim 1 wherein the patient expresses a homodimer of two mutant ER-α polypeptides.

11. The method of claim 1 wherein the patient expresses a homodimer of two wild-type ER-α polypeptides.

12. The method of claim 1 wherein the patient expresses a heterodimer of one wild-type ER-α polypeptide and one mutant ER-α polypeptide, or a heterodimer of one wild-type ER-β polypeptide and one mutant ER-α polypeptide.

13. The method of claim 12 wherein the patient has a tumor and a plurality of cells of the tumor express the mutant ER.

14. The method of claim 1 wherein the patient has received a chemotherapeutic agent, a biological therapy, a cancer vaccine, an angiogenesis inhibitor, hormone therapy, radiation therapy, surgery, or any combination thereof.

15. The method of claim 14 wherein the biological therapy is a peptide, a cytokine, an antibody, a therapeutic virus, a therapeutic bacterium, gene therapy, siRNA, adoptive T-cell transfer, or any combination thereof.

16. The method of claim 1 wherein the patient has received an aromatase inhibitor, a selective estrogen receptor modulator (SERM), a selective estrogen degrader (SERD), a PI3 kinase/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

17. The method of claim 1 wherein the patient has received fulvestrant, tamoxifen, anastrozole, letrozole, exemestane, goserelin, leuprolide, raloxifene, toremifene, megestrol acetate, bazedoxifene, or any combination thereof.

18. The method of claim 1 wherein the patient has received an anthracycline, a taxane, a platinum agent, an epothilone, or a nucleoside analog.

19. The method of claim 1 wherein the patient has received cisplatin, carboplatin, capecitabine, cyclophosphamide, docetaxel, doxorubicin, epirubicin, eribulin, fluorouracil, gemcitabine, ixabepilone, mitoxantrone, methotrexate, paclitaxel, pamidronate, vinorelbine, or any combination thereof.

20. The method of claim 1 wherein the patient has received pertuzumab, trastuzumab, lapatinib, everolimus, bevacizumab, temsirolimus, or any combination thereof.

21. The method of claim 1 wherein the ESR1 mutation results in a substitution, insertion or deletion of one or more amino acids in the ER polypeptide.

22. The method of claim 21 wherein the ESR1 mutation results in an amino acid substitution in the N-terminal domain, the DNA binding domain, the hinge region or the ligand binding domain of the estrogen receptor.

23. The method of claim 1 wherein the amino acid substitution is selected from among L536R, Y537N, Y537C, Y537S, and D538G.

24. The method of claim 1 wherein the patient is selected for treatment with the estrogen receptor modulator compound by the steps of:
a) detecting a mutation in the ESR1 gene in a sample comprising nucleic acid from the patient; and b) selecting the patient for treatment with the estrogen receptor modulator compound if the patient has the ESR1 mutation.

25. The method of claim 24 wherein the nucleic acid is RNA or DNA.

26. The method of claim 25 wherein the DNA is genomic DNA.

27. The method of claim 24 wherein the method further comprises isolating mRNA from the nucleic acid sample.

28. The method of claim 24 wherein the method further comprises amplifying a nucleic molecule comprising the mutation from the nucleic acid sample.

29. The method of claim 28 wherein amplification is by polymerase chain reaction (PCR) or digital PCR.

30. The method of claim 29 wherein PCR amplification comprises using a pair of oligonucleotide primers that flank the region comprising the mutation.

31. The method of claim 24 comprising contacting the nucleic acid with a sequence specific nucleic acid probe, wherein the sequence specific nucleic acid probe that binds to the nucleic acid having the mutation and does not bind to the wild-type nucleic acid.

32. The method of claim 24 wherein the sample comprises nucleic acid from one or more tumor cells.

33. The method of claim 32 wherein the tumor cell is taken from a tumor biopsy sample, a blood sample, a serum sample, a lymph sample, or a bone marrow aspirate.

34. The method of claim 33 wherein the tumor cell is a circulating tumor cell.

35. The method of claim 34 wherein the sample comprises circulating tumor DNA (ctDNA).

\* \* \* \* \*

SEQUENCE LISTING

```
<160> NUMBER OF SEQ ID NOS: 2

<210> SEQ ID NO 1
<211> LENGTH: 1788
<212> TYPE: DNA
<213> ORGANISM: Homo sapiens

<400> SEQUENCE: 1
atgaccatga ccctccacac caaagcatct gggatggccc tactgcatca gatccaaggg      60
aacgagctgg agcccctgaa ccgtccgcag ctcaagatcc ccctggagcg gcccctgggc     120
gaggtgtacc tggacagcag caagcccgcc gtgtacaact accccgaggg cgccgcctac    180
gagttcaacg ccgcggccgc cgccaacgcg caggtctacg gtcagaccgg cctcccctac     240
ggccccgggt ctgaggctgc ggcgttcggc tccaacggcc tgggggggttt ccccccactc    300 aacagcgtgt ctccgagccc gctgatgcta ctgcaccgc cgccgcagct gtcgccttc     360
```

```
ctgcagcccc acggccagca ggtgccctac tacctggaga cgagcccag cggctacacg      420 gtgcgcgagg ccggcccgcc ggcattctac aggccaaatt cagataatcg acgccagggt      480
ggcagagaaa gattggccag taccaatgac aagggaagta tggctatgga atctgccaag      540
gagactcgct actgtgcagt gtgcaatgac tatgcttcag gctaccatta tggagtctgg      600
tcctgtgagg gctgcaaggc cttcttcaag agaagtattc aaggacataa cgactatatg      660
tgtccagcca ccaaccagtg caccattgat aaaaacagga ggaagagctg ccaggcctgc      720
cggctccgta atgctacga agtgggaatg atgaaaggtg ggatacgaaa agaccgaaga      780
ggagggagaa tgttgaaaca caagcgccag agagatgatg ggagggcag gggtgaagtg      840 gggtctgctg gagacatgag agctgccaac ctttggccaa gcccgctcat gatcaaacgc      900
tctaagaaga acagcctggc cttgtccctg acggccgacc agatggtcag tgccttgttg      960
gatgctgagc ccccgatact ctattccgag tatgatccta ccagacccct cagtgaagct     1020
tcgatgatgg gcttactgac caacctggca gacaggagc tggttcacat gatcaactgg     1080
gcgaagaggg tgccaggctt gtgatttg accctccatg atcaggtcca ccttctagaa     1140
tgtgcctggc tagagatcct gatgattggt ctcgtctggc gctccatgga gcacccaggg     1200
aagctactgt ttgctcctaa cttgctcttg gacaggaacc agggaaaatg tgtagagggc     1260
atggtggaga tcttcgacat gctgctggct acatcatctc ggttccgcat gatgaatctg     1320
cagggagagg agtttgtgtg cctcaaatct attatttgc ttaattctgg agtgtacaca     1380
tttctgtcca gcaccctgaa gtctctggaa gagaaggacc atatccaccg agtcctggac     1440
aagatcacag acactttgat ccacctgatg gccaaggcag gcctgaccct gcagcagcag     1500
caccagcggc tggcccagct cctcctcatc ctctcccaca tcaggcacat gagtaacaaa     1560
ggcatggagc atctgtacag catgaagtgc aagaacgtgg tgcccctcta tgacctgctg     1620
ctggagatgc tggacgccca ccgcctacat gcgcccacta gccgtggagg ggcatccgtg     1680
gaggagacgg accaaagcca cttggccact gcgggctcta cttcatcgca ttccttgcaa     1740
aagtattaca tcacgggga ggcagagggt ttccctgcca cggtctga                  1788
```

<210> SEQ ID NO 2
<211> LENGTH: 595
<212> TYPE: PRT
<213> ORGANISM: Homo sapiens

<400> SEQUENCE: 2

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
```

```
            115                 120                 125
Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540
```

```
Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595
```